(12) United States Patent
Liebeschuetz et al.

(10) Patent No.: US 7,220,781 B2
(45) Date of Patent: May 22, 2007

(54) META-BENZAMIDINE DERIVATIVES AS SERINE PROTEASE INHIBITORS

(75) Inventors: John Walter Liebeschuetz, Bollington (GB); William Alexander Wylie, Carrickfergus (GB); Bohdan Waszkowycz, Wilmslow (GB); Christopher William Murray, Swavesey (GB); Andrew David Rimmer, Chorley (GB); Pauline Mary Welsh, Macclesfield (GB); Stuart Donald Jones, Prestbury (GB); Jonathan Michael Ernest Roscoe, Bude (GB); Stephen Clinton Young, Stockport (GB); Phillip John Morgan, Congleton (GB)

(73) Assignee: Tularik Limited, London (GB)

( * ) Notice: Subject to any disclaimer, the term of this patent is extended or adjusted under 35 U.S.C. 154(b) by 407 days.

(21) Appl. No.: 10/752,568

(22) Filed: Jan. 8, 2004

(65) Prior Publication Data

US 2004/0143018 A1 Jul. 22, 2004

Related U.S. Application Data

(63) Continuation of application No. 09/988,082, filed on Nov. 19, 2001, now Pat. No. 6,740,682, which is a continuation-in-part of application No. 09/485,678, filed as application No. PCT/GB98/02605 on Aug. 28, 1998, now abandoned, and a continuation-in-part of application No. PCT/GB00/02291, filed on Jun. 13, 2000.

(60) Provisional application No. 60/142,064, filed on Jul. 2, 1999.

(30) Foreign Application Priority Data

| Aug. 29, 1997 | (GB) | ................................ 9718392.5 |
| Feb. 13, 1998 | (GB) | ................................ 9803173.5 |
| Jun. 14, 1999 | (GB) | ................................ 9913823.2 |

(51) Int. Cl.
 *A01N 37/52* (2006.01)

(52) U.S. Cl. ...................... 514/637; 514/357; 514/538; 514/563; 514/617; 544/353; 544/365; 546/194; 546/280; 546/281; 560/35; 560/251; 562/440; 564/157; 564/161; 564/246

(58) Field of Classification Search ................ 514/357, 514/538, 563, 637, 617; 544/365, 353; 546/194, 280, 281; 560/35, 251; 562/440; 564/157, 161, 246
See application file for complete search history.

(56) References Cited

U.S. PATENT DOCUMENTS 6,080,767 A * 6/2000 Klein et al. .................. 514/357
6,498,165 B1 12/2002 Armstrong et al.
6,545,055 B1 4/2003 Zhu et al.
6,638,980 B1 * 10/2003 Su et al. .................. 514/620
6,916,957 B2 * 7/2005 Lively et al. ............... 564/157

FOREIGN PATENT DOCUMENTS

| EP | 0483667 A | 5/1992 |
| EP | 0540051 | 5/1993 |
| EP | 0588655 A | 3/1994 |
| EP | 0672658 A | 9/1995 |
| WO | WO 92/08709 A | 5/1992 |
| WO | WO 94/29336 A | 12/1994 |
| WO | WO 95/13274 A | 5/1995 |
| WO | WO 97/24118 | 7/1997 |
| WO | WO 97/24135 A | 7/1997 |
| WO | WO 97/36859 A | 10/1997 |
| WO | WO 00/71507 | 11/2000 |
| WO | WO 00/71508 | 11/2000 |
| WO | WO-00/71508 A2 * | 11/2000 |
| WO | WO 00/79453 | 11/2000 |

OTHER PUBLICATIONS

Ferroni et al. "Ethylesters of N-amidinobenzoyl amino acids . . . " CA 108:48724 (1987).*
Exhibit I, structure delineation for priority WO99/11658.*
Liebeschuetz et al. Preparation of meta-benzamidine . . . CA 130:237884 (1999).*
R. Ferroni et al; 1 Farmaco Ed Sci (1987)42(10)pp. 709-715. (Chemical Abstracts, vol. 108 No.7 Dec. 23, 1985 Columbus, Ohio, US; Abstract No. 48724q. XP00208333.

(Continued)

*Primary Examiner*—Celia Chang
(74) *Attorney, Agent, or Firm*—Martin A. Hay

(57) ABSTRACT

Compounds of formula I

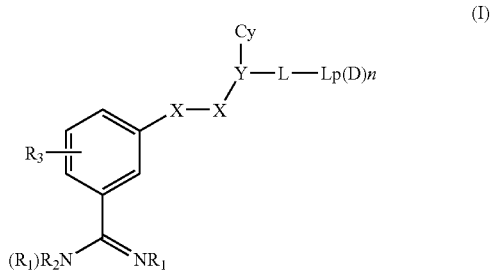

in which $R_1$, $R_2$, $R_3$, each X, L, Y, Cy, Lp, D and n have the meanings as set out in the specification, and corresponding compounds in which the unsubstituted or substituted amidine group is replaced with an unsubstituted or substituted aminomethyl group, are useful as serine protease inhibitors.

23 Claims, No Drawings

OTHER PUBLICATIONS

R. Ferroni et al; Il Farmaco Ed Sci (1985)40(10)pp. 717-729. (Chemical Abstracts, vol. 103, No. 25, Dec. 23, 1985 Columbus, Ohio, US; Abstract No. 209699z, XP002083330).

J. Sturzebecher et al; Thrombosis Research (1976)9(6)pp. 637-646.

Alig et al., "Low molecular weight, nonpeptide fibrinogen receptor antagonists" CA 118: 7363.

B. R. Baker et al; Journal of Medicinal Chemistry, vol. 12, No. 3, 1969, p. 408-414, Washington US. (Chemical Abstracts, vol. 71, No. 7 Aug. 18, 1969, Columbus, Ohio, US; Abstract No. 28982m,XP002083332).

H. Vieweg et al; Pharmazie, vol. 38, No. 12, 1983, p. 818-820 Berlin DE. (Chemical Abstracts, vol. 101, No. 1, Jul. 2, 1984, Columbus, Ohio, US; Abstract No. 6764c, XP002083333).

* cited by examiner

META-BENZAMIDINE DERIVATIVES AS SERINE PROTEASE INHIBITORS

This application is a continuation of application Ser. No. 09/988,082 filed on Nov. 19, 2001, now U.S. Pat. No. 6,740,682, which is a continuation-in-part of application Ser. No. 09/485,678 filed on Feb. 25, 2000, now abandoned which in turn is a 371 of PCT/GB98/02605 filed on Aug. 28, 1998 and is also a continuation-in-part of PCT/GB00/02291 filed on Jun. 13, 2000 which claims the benefit of provisional application No. 60/142,064 filed on Jul. 2, 1999.

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of α1 protease inhibitor deficiency with emphysema and cirrhosis and C1 esterase inhibitor deficiency with angioedema.

We have now found that certain novel amidine compounds are particularly effective as inhibitors of serine proteases, especially proteases with negatively charged P1 specificity pockets, and most especially the serine proteases thrombin, trypsin, urokinase and Factor Xa.

Thus viewed from one aspect we provide serine protease inhibitor compounds having an m-benzamidine group and a lipophilic group coupled to a cyclic group-attached carbon or nitrogen atom (hereinafter the alpha atom), the coupling of the m-benzamidine group to the alpha atom being by a linker group providing a two backbone atom linking chain, the backbone atoms being selected from C, N, O and S and at least one being C, optionally wherein one or both of the backbone atoms form part of a cyclic group and the coupling of the lipophilic group to the alpha atom being by a linker group capable of separating the alpha atom from the lipophilic group by a range of 2.3 to 6.5 Å in length.

In the compounds of the invention, the lipophilic group is itself optionally substituted by a hydrogen bond donor group. Where this is the case, the lipophilic group and its linker preferably are conformable to separate by from 7.5 to 15.0 Å the alpha atom and the hydrogen bond donor atom of the donor group.

Where distances from the alpha atom to the lipophilic group or to the hydrogen bond donor atom are mentioned, these relate to the distances between the centre of the alpha atom and the centre of the first atom of the lipophilic group or the centre of the hydrogen bond donor atom.

Such distances can be calculated from crystallographic data for any given compound from the bond lengths and bond angles for individual bonds along the length of the molecule between the alpha atom and the first atom of the lipophilic group or the hydrogen bond donor atom. Similarly such distances may be calculated with reasonable accuracy from the bond lengths and bond angles known to be typical of such individual bonds.

The linker between the alpha atom and the lipophilic group may itself be a lipophilic moiety, e.g. an alkylene chain. The nature of the linker may vary considerably—the primary requirement is that it be conformable to place part or all of the lipophilic group at a desired distance away from the alpha atom. The lipophilic group thus desirably is able to occupy at least part of a space 2.3 to 15.0 Å from the alpha atom. The length of the linker generally corresponds to 1 to 5 backbone atoms and may be a chain, branched chain or cyclic linker (e.g. a cyclic amide or an aromatic heterocycle). In one embodiment the alpha atom forms part of a cyclic group which also forms the linker to the lipophilic group.

Thus viewed from an alternative aspect the invention provides serine protease inhibitor compounds of formula I

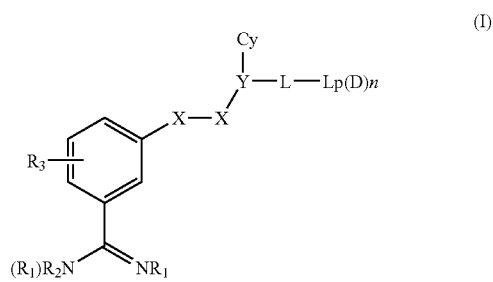

(where $R_1$ and $R_2$ each independently is hydrogen or hydroxyl, alkoxy, alkyl, aminoalkyl, hydroxyalkyl alkoxyalkyl, alkoxycarbonyl, acyloxymethoxycarbonyl or alkylamino optionally substituted by hydroxy, alkylamino, alkoxy, oxo, aryl or cycloalkyl;

each $R_3$ independently is $R_1$, $R_2$, amino, halo, cyano, nitro, thiol, alkylthio, alkylsulphonyl, alkylsulphenyl, alkylsulphonamido, alkylaminosulphonyl, aminosulphonyl, haloalkoxy and haloalkyl;

each X independently is a C, N, O or S atom or a CO, $CR_1$, $C(R_1)_2$ or $NR_1$ group, at least one X being C, CO, $CR_1$ or $C(R_1)_2$, with the proviso that if the benzamidine group is unsubstituted (i.e. no non-hydrogen $R_3$ group is present) and the X-X group is —$CH_2C(R_1)_2$— then $R_1$ is hydrogen or is attached to the alkylene carbon atom by a heteroatom;

L is an organic linker group containing 1 to 5 backbone atoms selected from C, N, O and S, or a branched alkyl or cyclic group;

Y (the α-atom) is a nitrogen atom or a $CR_1$ group or Y and L taken together form a cyclic group;

Cy is a saturated or unsaturated, mono or poly cyclic, homo or heterocyclic group, preferably containing 5 to 10 ring atoms and optionally substituted by groups $R_3$ or phenyl optionally substituted by $R_3$;

Lp is a lipophilic organic group, e.g. an alkyl, heterocyclic, alkenyl, alkaryl, cycloalkyl, polycycloalkyl, cycloalkenyl, aryl, aralkyl or haloalkyl group or a combination of two or more such groups optionally substituted by one or more of oxa, oxo, aza, thio, halo, amino, hydroxy or $R_3$ groups, preferably a group containing up to 25 carbon atoms;

D is a hydrogen bond donor group; and n is 0, 1 or 2);

or a physiologically tolerable salt thereof, e.g. a halide, phosphate or sulphate salt or a salt with ammonium or an organic amine such as ethylamine or meglumine.

In the compounds of the invention, where the alpha atom is carbon it preferably has the conformation that would result from construction from a D-α-aminoacid $NH_2$—$CR_1$(Cy)-COOH and a m-carboxyl benzamidine. Likewise the fourth substituent $R_1$ at an alpha carbon is preferably a methyl or hydroxymethyl group or hydrogen.

In compounds of formula (I) it is envisaged that the unsubstituted or substituted amidino group could be repalced by a substituted or unsubstituted aminomethyl group although an amidino derivative is preferred.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons; cyclic groups preferably have ring sizes of 3 to 8 atoms; and fused multicyclic groups preferably contain 8 to 16 ring atoms.

The linker group from the benzamidine group to the alpha atom is preferably selected from —CH=CH—, —CONH—, —$CONR_1$—, —NH—CO—, —NH—$CH_2$—, —$CH_2$—NH—, —$CH_2$O—, —$OCH_2$—, —COO—, —OC=O— and —$CH_2CH_2$—. Preferably, the X moiety nearest to the alpha atom is an NH or O atom, most preferably a NH group. The X moiety alpha to the phenyl] ring is preferably a carbon based group such as $CH_2$ or CO, preferably CO. Thus a particularly preferred linker X-X is —CONH—.

The linker group from the alpha atom to the lipophilic group is preferably CO, $CH_2NH$, $CONR_1(CH_2)_m$, $(CH_2)_mN(R_1)CO(CH_2)_m$, $(CH_2)_{m+2}$, $CO(CH_2)_m$, $(CH_2)_mCO$, $(CH_2)_mOC=O$, $(CH_2)_mO$ or $CH=CH(CH_2)_m$ (where each m is independently 0 or 1). The linker may be optionally branched, for example, to incorporate a polar functionality. In a preferred embodiment Y and L taken together form a cyclic group and the alpha atom is therefore a carbon atom. The cyclic group can be unsubstituted or substituted and can have a ring size of from 3 to 8 atoms. Preferably, the cyclic group is a cyclic amide, most preferably wherein the amide nitrogen of the cyclic amide group is bound to the lipophilic group.

The lipophilic group preferably comprises a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or alkenylene group all optionally substituted by one or more groups $R_3$, or a combination of at least two such groups linked by a spiro linkage or a single or double bond or by C=O, O, S, SO, $SO_2$, $CONR_1$, $NR_1$—CO—, $NR_1$ linkage. For example, representative lipophilic groups include a methyl-cyclohexyl, methylcyclohexylmethyl, methylphenylmethyl, phenylethyl, benzylpiperidinyl, benzoylpiperidinyl, bispiperidinyl or phenylpiperazinyl.

Most preferably, the lipophilic group is selected from

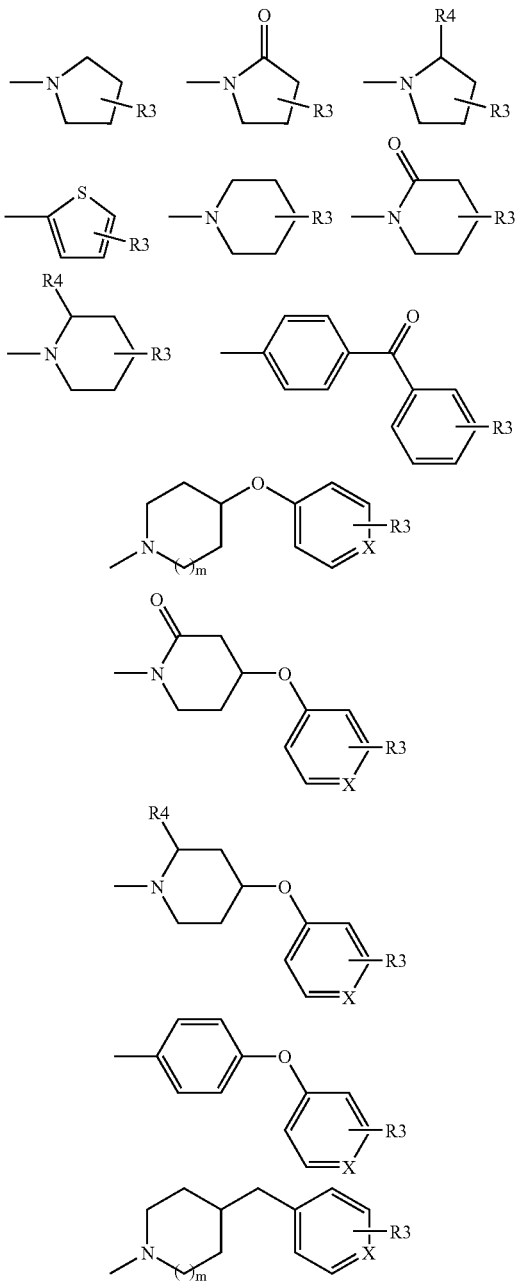

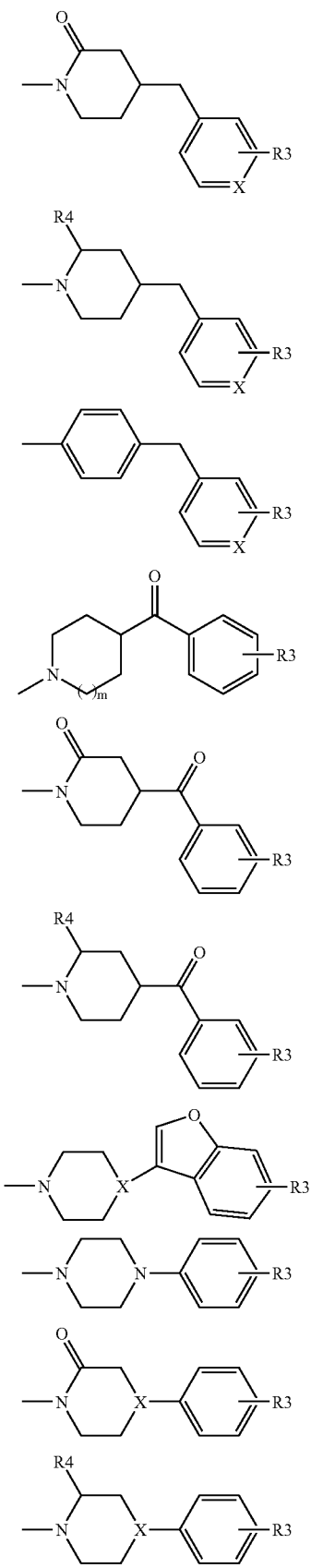
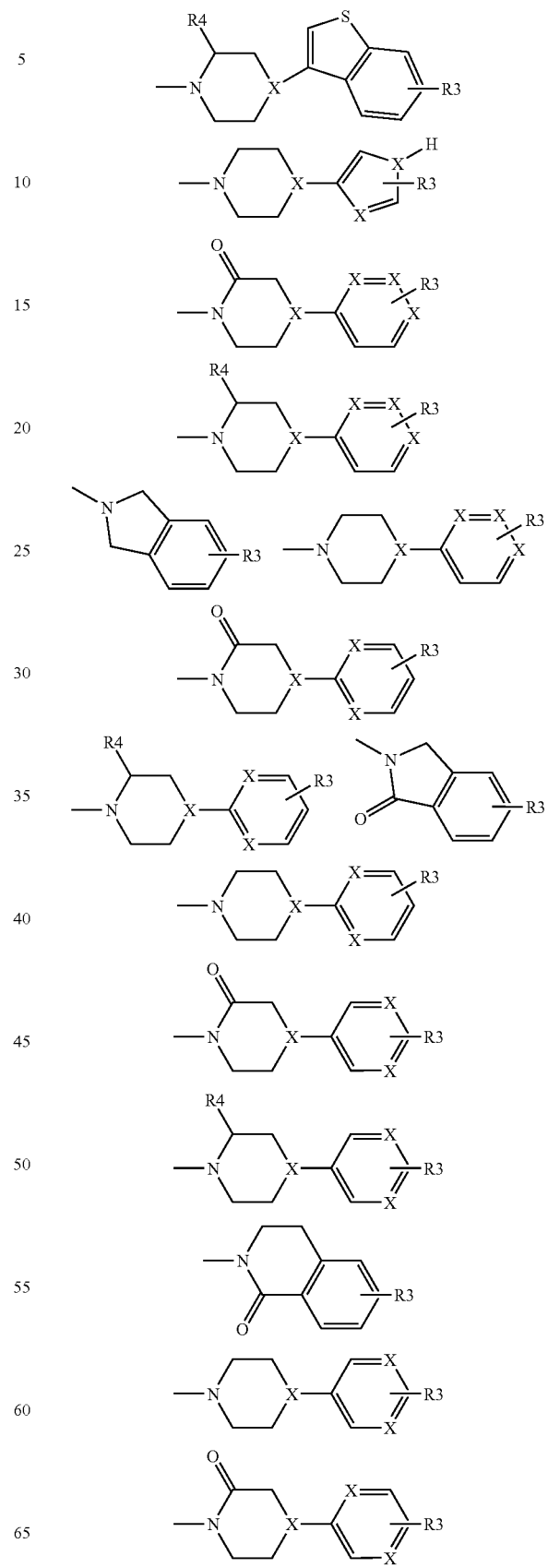

-continued
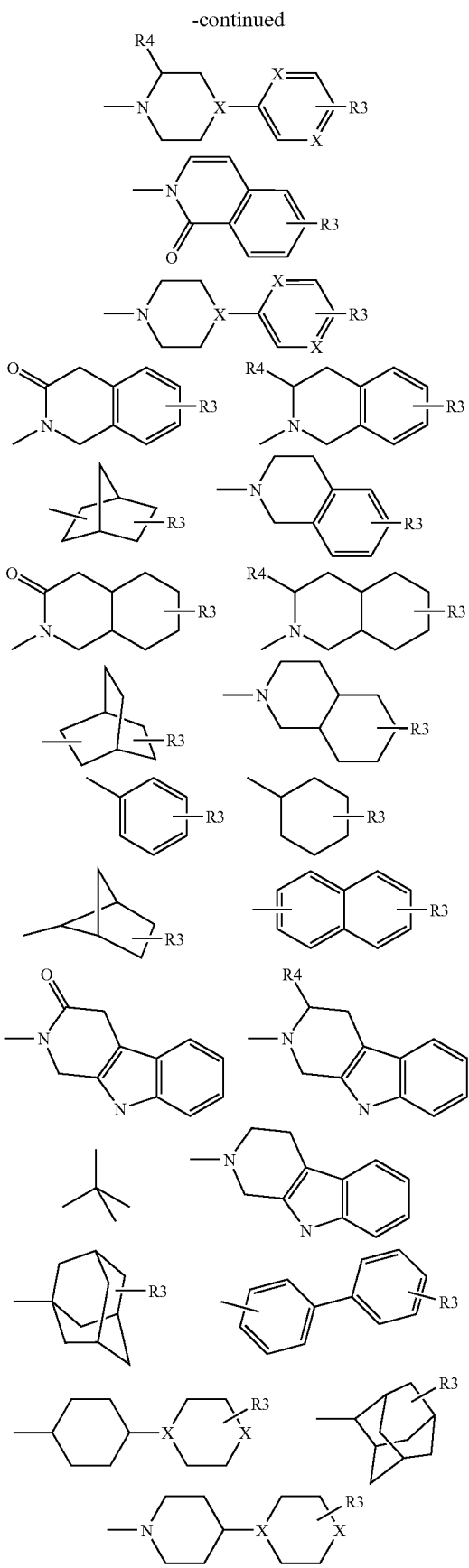
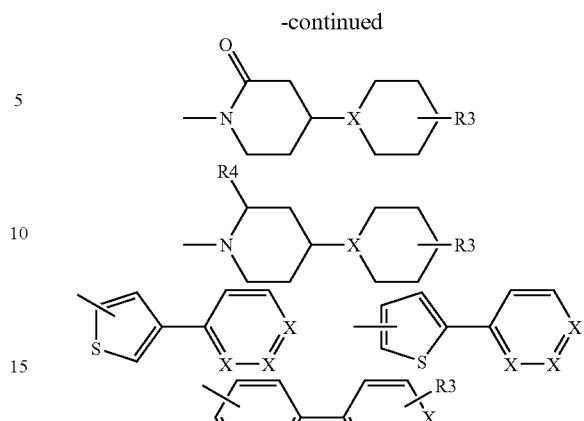
wherein $R_3$ is $R_1$, aryl or cycloalkyl;
m represents 0 or 1;
$R_4$ represents hydrogen, $(CH_2)_w COOH$, $(CH_2)_w CONH_2$, $(CH_2)_w CON\alpha\text{-AminoAcid}$;
w represents an integer from 0 to 4; and
X represents CH or N.
For example specific lipophilic groups include
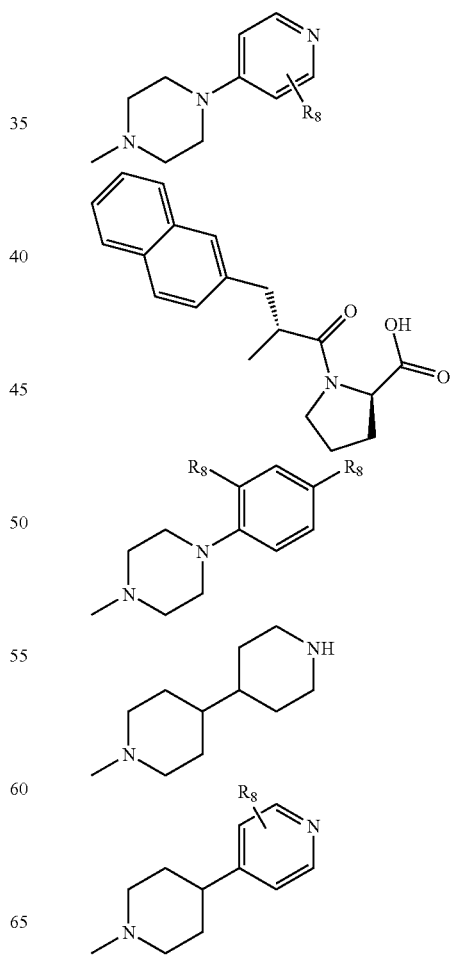

-continued

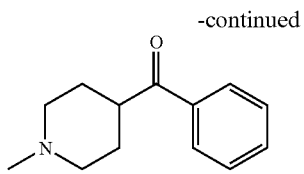

especially when $R_8$ represents H, OMe, F, $NO_2$, OH or Cl.

The hydrogen bond donor group which may be attached to the lipophilic group preferably has a nitrogen or oxygen atom as the donor atom and conveniently is a hydroxyl group, a primary, secondary or tertiary amine, or a primary or secondary imine group (as part of an amidine or guanidine) or a saturated or unsaturated heterocyclic group containing a ring nitrogen, preferably a group containing 5 to 7 ring atoms. Where the donor atom is a ring nitrogen, the remote portion of the heterocyclic ring may be part of the lipophilic group.

The cyclic group attached to the alpha carbon is preferably an optionally $R_3$ substituted phenyl or naphthyl group.

The benzamidino group is preferably an unsubstituted m-benzamidino group, or a substituted m-benzamidino group bearing metabolically labile groups such as acyloxymethoxycarbonyl, alkoxycarbonyl or hydroxy.

Accordingly, preferred compounds of the invention are of formula

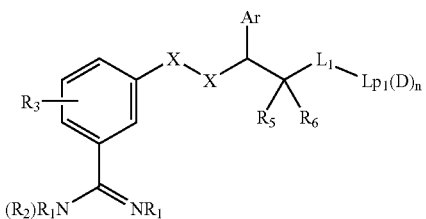

(wherein $R_1$, $R_2$ and $R_3$ are as hereinbefore defined, $R_1$ and $R_2$ preferably being hydrogen or one representing a metabolically labile group such as alkoxycarbonyl or hydroxy, $R_3$ preferably being hydrogen, OH or $NH_2$ and when other than hydrogen preferably being para to the amidine group);

$R_5$ and $R_6$ are hydrogen or taken together with the carbon atom to which they are attached represent a carbonyl group;

Ar is an unsubstituted or substituted aryl group, preferably phenyl;

X-X is —CONH—, —$CH_2CH_2$—, $CH_2O$—, —COO—, —$CH_2NH$—, —$OCH_2$— or —$NHCH_2$—;

$L_1$ is a valence bond or an organic linker group containing 1 to 4 backbone atoms selected from C, N and O;

$Lp_1$ is a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or is alkenylene group all optionally substituted by a group $R_3$, or a combination of at least two such groups linked by a spiro linkage or a single or double bond or by C=O, O, S, SO, $SO_2$, $CONR_1$, $NR_1$—CO—, $NR_1$ linkage. For example, representative lipophilic groups include a methyl-cyclohexyl, methylcyclohexylmethyl, bispiperidinyl, methylphenylmethyl, phenylethyl, benzylpiperidinyl, benzoylpiperidinyl or phenylpiperazinyl and those as hereinbefore described;

D is a hydrogen bond donor group;

and n is 0, 1 or 2).

In one embodiment, $L_1$ comprises the backbone of an alpha amino acid, the lipophilic group being the side chain of the amino acid. The carboxyl part of the alpha amino acid may be optionally coupled via an amide bond to an amino acid or to a primary or secondary cyclic or acyclic alkyl amine or diamine or via an ester bond to primary or secondary alcohols.

In a preferred embodiment, $L_1$ represents a valence bond and the lipophilic group is bound directly to the carbonyl alpha to the alpha atom via a nitrogen atom which forms part of the lipophilic group. Suitable lipophilic groups in this case therefore include piperidinyl, pyrrolidinyl and piperazinyl. In a preferred embodiment the piperidine or piperazinyl group is further substituted by a phenyl, benzyl, piperidine, pyridine or benzoyl group, optionally substituted on the phenyl ring by one or more $R_3$ groups.

In a further embodiment, the lipophilic group has attached a group of the formula —$COOR_1$ or —CON-aminoacid or ester derivative thereof.

In another embodiment the group binding the alpha carbon atom to the lipophilic group comprises a heterocyclic group. Accordingly, preferred compounds of the invention also include

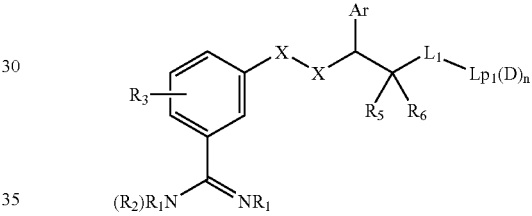

(wherein $R_1$, $R_2$ and $R_3$ are as hereinbefore defined $R_1$ and $R_2$ preferably being hydrogen or one representing a metabolically labile group such as alkoxycarbonyl or hydroxy, $R_3$ preferably being hydrogen, OH or $NH_2$ and when other than hydrogen preferably being para to the amidine group);

Ar is an unsubstituted or substituted aryl group, preferably phenyl;

X-X is —CONH—, —$CH_2CH_2$—, $CH_2O$—, —COO—, —$CH_2NH$—, —$OCH_2$— or —$NHCH_2$—;

m is 0, 1 or 2;

Het is a 5 or 6-membered heterocyclic group interrupted by 1, 2 or 3 heteroatoms selected from O, N and S optionally substituted by a group $R_3$;

$Lp_1$ is a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or alkenylene group all optionally substituted by a group $R_3$, or a combination of at least two such groups linked by a spiro linkage or a single or double bond or by C=O, O, S, SO, $SO_2$, $CONR_1$, $NR_1$—CO—, $NR_1$ linkage. For example, representative lipophilic groups include a methyl-cyclohexyl, methylcyclohexylmethyl, methylphenylmethyl, phenylethyl, benzylpiperidinyl, benzoylpiperidinyl, bispiperidinyl or phenylpiperazinyl;

D is a hydrogen bond donor group;

and n is 0, 1 or 2).

Where Het is a five membered ring, the two ring atoms at which it is connected are preferably separated by one ring atom. Where Het is a six-membered ring, the two ring atoms at which it is connected are preferably separated by one or two ring atoms. Representative heterocyclic groups include thiazole, oxazole, oxadiazole, triazole, thiadiazole or imidazole. Where the heterocyclic group is substituted by $R_3$ this is preferably a COOH or $COOR_1$ connected to the heterocycle via a valence bond or alkylene chain.

In a further embodiment, the lipophilic group has attached a group of the formula —$COOR_1$ or —CON-aminoacid or ester derivative thereof.

The compounds of the invention may be prepared by conventional chemical synthetic routes, e.g. by amide bond formation to couple the benzamidine function to the alpha atom and to couple the lipophilic function to the alpha atom. Where the alpha atom is a carbon, the cyclic group-alpha atom combination may conveniently derive from an alpha amino acid with the benzamidine deriving from a m-amidino-benzoic acid. Amide formation from such reagents (in which the amidine function may if desired be protected during some or all of the synthesis steps) yields a compound of formula II.

Bd-CONH—CH(Cy)-COOH      (II)

(where Cy is as defined above and Bd is an optionally protected m-benzamidine group).

The lipophilic group (and optionally simultaneously the hydrogen bond donor) may then conveniently be introduced by reaction of a compound of formula II (or another analogous carboxylic acid) optionally after transformation into an activated form, e.g. an acid chloride or active ester, with a lipophilic group carrying an amine, hydroxylamine, hydrazine or hydroxyl group, e.g. to produce compounds with linkages of —CO—$NR_1$—, —CO—$NR_1$—O—, —CO—$NR_1$—$NR_1$— and —CO—O— from the alpha atom (where it is a carbon) to the lipophilic group. Where Y and L taken together form a cyclic amide group the lipophilic group can be conveniently introduced by reacting the compound of formula (II) with a lipophilic group carrying a secondary amine with an active side chain. Cyclisation can be base induced via nucleophilic attack of the alpha atom on a leaving group on the active side chain. If necessary the amide linkage can be reduced using an appropriate reducing agent employing the necessary protection depending on whether concurrent reduction of the carboxylic acid moiety is also desired. Alternatively a compound of formula II or another analogous carboxylic acid may be transformed into an alcohol by reaction with isobutylchloroformate and reduction with sodium borohydride.

Such an alcohol, e.g. of formula III

Bd-CONH—CH(Cy)$CH_2$OH      (III), can be reacted to introduce the lipophilic group by reactions such as:

alkylation with an alkyl halide in the presence of a base;

reaction with diethyl azodicarboxylate/triphenylphosphine and a hydroxylated aryl compound;

by reaction with an activated carboxylic acid (e.g. an acid chloride) or with a carboxylic acid and diethylazodicarboxylate/triphenylphosphine;

by reaction with an isocyanate; and by treatment with methanesulphonyl chloride or trifluoromethanesulphonic anhydride and reaction with an amine, or with a thiol optionally followed by oxidation, e.g. with potassium metaperiodate or hydrogen peroxide.

In this way compounds with linkages of —$CH_2$—O—, —$CH_2$—O—CO—, —$CH_2$—O—CO—$NR_1$—, —$CH_2$—$NR_1$—, —$CH_2$—S—, —$CH_2$—SO— and —$CH_2$—$SO_2$— between the alpha carbon and the lipophilic group may be produced.

Alternatively the alcohol can be oxidized to form a corresponding aldehyde (e.g. by oxidation with manganese dioxide or DMSO/oxalyl chloride or DMSO/$SO_3$ or Dess-Martin reagent) which may be reacted to introduce the lipophilic group by reactions such as:

reaction with Wittig reagents or Horner-Emmons reagents, optionally followed by reduction of the resulting carbon:carbon double bond using $H_2$/Pd-carbon;

reaction with an organometallic, eg a Grignard reagent, optionally followed by reaction on the resulting hydroxyl group, such as oxidation (eg with $MnO_2$, DMSO/oxalyl chloride or Dess-Martin reagent), alkylation (eg with an alkyl halide in the presence of a base in a solvent such as DMF), arylation (eg with diethylazo dicarboxylate/triphenyl phosphine and a hydroxyaryl compound), ester formation (eg with an acid chloride or with a carboxylic acid and diethylazido dicarboxylate/triphenyl phosphine), or carbamate formation (eg with an isocyanate);

by reaction with an amine followed by reduction, e.g. with sodium cyanoborohydride;

by reaction with a hydrazine; or by reaction with a carbazide.

In this way compounds with linkages of —CH=$CR_1$—, —$CH_2$—$CHR_1$—, —CHOH—, —$CHR_1$—O—, —$CHR_1$—O—CO—, —$CHR_1$—O—CO—$NR_1$—, —CO—, —$CH_2$—$NR_1$—, —CH=N—$NR_1$— and —CH=N—$NR_1$—CO—$NR_1$— between the alpha carbon and the lipophilic group may be produced.

The transformation of alcohol to amine referred to above may be used to produce an amine reagent for lipophilic group introduction, e.g. a compound Bd-CONH—CH(Cy)-$CH_2$—$NR_1$H.

Such an amine reagent may be reacted to introduce the lipophilic group, e.g. by acylation with an acid halide or activated ester, by reaction with isocyanate, by reaction with an isothiocyanate, or by reaction with a sulphonyl chloride. In this way compounds with linkages of —$CH_2NR_1$—CO—, —$CH_2$—$NR_1$—CO—$NR_1$—, —$CH_2NR_1$—CS—$NR_1$— and —$CH_2NR_1$—$SO_2$— between the alpha carbon and the lipophilic groups may be produced.

The transformation of acid to amide referred to above may be used to produce an amide reagent for introduction of the lipophilic group, e.g. a compound Bd-CONH—CH(Cy)-$CON(R_1)_2$.

Such amides may be reacted to introduce lipophilic groups, e.g. by reaction with a haloketone (e.g. phenacyl bromide). This provides a linkage

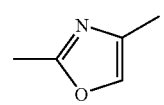

from alpha carbon to lipophilic group.

Analogously the amide may be transformed to a thioamide by reaction with Lawesson's reagent and then reacted with a haloketone to form a linkage

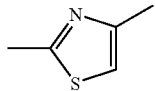

The amide reagent may likewise be transformed to a nitrile reagent by dehydration, e.g. with trifluoroacetic anhydride. The nitrile reagent may be reacted with hydrazine then with acyl halide and then cyclized, (e.g. with trifluoroacetic anhydride) to produce a linkage

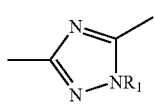

Alternatively it may be treated with hydroxylamine then reacted with acyl halide and cyclized (e.g. with trifluoroacetic anhydride) to produce a linkage

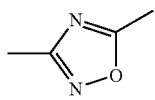

The hydrazide produced by reaction of a carboxylic acid reagent with hydrazine discussed above may likewise be used as a reagent for lipophilic group introduction, e.g. as a compound of formula Bd-CONH—CH(Cy)-CO—NR$_1$—N(R$_1$)$_2$.

Thus the hydrazide reagent can be reacted with an acyl halide and cyclized, e.g. with trifluoroacetic anhydride to yield a linkage

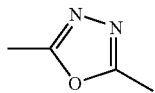

or reacted with an acyl halide or an isocyanate to yield linkages —CO—NR$_1$—NR$_1$—CO— and —CO—NR$_1$—NR$_1$—CO—NR$_1$— respectively.

Alternatively the hydrazide may be transformed by reaction with Lawesson's reagent and then reacted with an acyl halide and cyclized (e.g. with trifluoroacetic anhydride) to produce the linkage

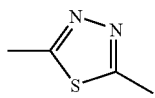

An alternative route to these compounds is to carry out any of the above chemical reactions to incorporate the lipophilic group (an optional H bond donor) into a protected intermediate such as a compound of formula (IV).

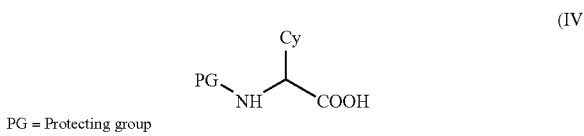

(IV)

PG = Protecting group

The protecting group may then be removed before coupling of the m-amidino benzoic acid (optionally protected).

A starting reagent for lipophilic group introduction where the alpha atom is nitrogen may be produced for example by reaction of a beta protected hydrazine (such protection to be chosen as to be compatible with the subsequent reagents to be employed) with phosgene, diphosgene, triphosgene or N,N'carbonyl diimidazole to give a reactive compound of the type:

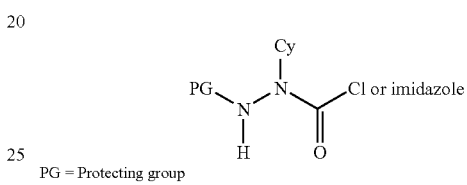

PG = Protecting group

This intermediate may be used as has been described above for the carboxylic starting reagents where the alpha atom is carbon.

Removal of the protecting group by standard methods and coupling with an activated m-carboxyl-benzamidine will give compounds of the type

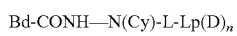

Bd-CONH—N(Cy)-L-Lp(D)$_n$ (where Bd, X, Y, Cy, L, Lp and D are as defined above)

Thus viewed from a further aspect the invention provides a process for the preparation of a compound according to the invention which process comprises coupling a lipophilic group to a compound of formula (V)

Bd-(X)$_2$—Y(Cy)-Z  (V)

(where Bd, X, Y and Cy are as defined above and Z is a reactive functional group), and optionally subsequently coupling a hydrogen bond donor group to said lipophilic group.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention. Viewed from this aspect the invention provides a pharmaceutical composition comprising a serine protease inhibitor according to the invention together with at least one pharmaceutically acceptable carrier or excipient.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor), said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

Experimantal

Abbreviations used follow IUPAC-IUB nomenclature. Additional abbreviations are Hplc, high-performance liquid chromatography; DMF, dimethylformamide; DCM, dichloromethane; HOAt, 1-hydroxy-7-azabenzotriazole; HATU, [O-(7-azabenzotriazol-1-yl)-1,1,3,3-tetramethyluronium hexafluorophosphate]; Fmoc, 9-Fluorenylmethoxycarbonyl; HOBt, 1-hydroxybenzotriazole; TBTU, 2-(1H-(benzotriazol-1-yl)-1,1,3,3-tetramethyluroniumtetrafluoroborate; DIPEA, diisopropylethylamine; Boc, tertiary butyloxycarbonyl; DIPCI, diisopropylcarbodiimide; DBU, 1,8-diazabicyclo[5.4.0]undec-7-ene; TEA, triethylamine; Rink linker, p-[(R,S)-α-[1-(9H-Fluoren-9-yl)methoxy-formamido]-2,4-dimethoxybenzyl]phenyl acetic acid; TFA, trifluoroacetic acid; MALDI-TOF, Matrix assisted laser desorption ionisation—time of flight mass spectrometry; and RT, retention time. Unless otherwise indicated, amino acid derivatives, resins and coupling reagents were obtained from Novabiochem (Nottingham, UK) and other solvents and reagents from Rathburn (Walkerburn, UK) or Aldrich (Gillingham, UK) and were used without further purification.

Purification: Purification was by gradient reverse phase Hplc on a Waters Deltaprep 4000 at a flow rate of 50 ml/min. using a Deltapak C18 radial compression column (40 mm×210 mm, 10-15 mm particle size). Eluant A consisted of aqTFA (0.1%) and eluant B 90% MeCN in aqTFA (0.1%) with gradient elution (Gradient 1, 0 min. 20% B then 20% to 100% over 36 min., Gradient 2, 0 min. 5% B for 1 min. then 5% B to 20% B over 4 min., then 20% to 60% over 32 min. or Gradient 3, 0 min. 20% B then 20% to 100% over 15 min.). Fractions were analysed by analytical Hplc and MALDI-TOF before pooling those with >95% purity for lyophilisation.

Analysis: Analytical Hplc was on a Shimadzu LC6 gradient system equipped with an autosampler, a variable wavelength detector at flow rates of 0.4 ml/min. Eluents A and B as for preparative Hplc. Columns used were Techogell5 C18 (2×150 mm)(Hplc Technology), Jupiter 5 C18 column (2.1×150 mm, 5 μm particle size) (Phenomenex) and Kromasil C4 (2.0×150 mm, 5 mm) HPLC Technology. Purified products were further analysed by MALDI-TOF and nmr.

All Fmoc-protected amino acids were purchased where available or prepared by known literature methods (1) with the exception of the following novel amino acid:

Preparation of (D,L)-N-Fluorenylmethyloxycarbonyl-4-phenylphenylglycine

A solution of 4-biphenylcarboxaldehyde (4.6 g 25 mmol), sodium cyanide (3.68 g 75 mmol) and ammonium carbonate (9.60 g 100 mmol) in 50% aqueous ethanol (175 ml) was heated at 50° C. for 20 hours. The reaction mixture was cooled, concentrated under reduced pressure and acidified to pH 2.0 with concentrated hydrochloric acid (fume hood). The intermediate 4-(4-phenylphenyl)-2,5-imidazolinedione was collected by filtration, washed with dilute (0.5%) HCl and dried before using as crude in the next stage. (Filtrates were retained and treated with sodium hypochlorite solution before disposal) The intermediate 4-(4-phenylphenyl)-2,5-imidazolinedione was refluxed in 16% aqueous sodium hydroxide (100 ml, 16% w/v) for 24 h. The reaction mixture was then filtered, cooled, diluted with water (100 ml) and then shaken with ethyl acetate and separated. The aqueous solution was adjusted to pH 5.1 with concentrated hydrochloric acid and the solid obtained collected by filtration, washed with a little water and dried to give 4-phenylphenylglycine (2.36 g, 42%). $^1$H nmr ($d_6$ DMSO) consistent with desired product.

To a vigorously stirred solution of 4-phenylphenylglycine (500 mg 2.2 mmol) in DCM (20 ml) was added DIPEA (614 μl 4.4 mmol) and then, carefully, chlorotrimethylsilane (558 μl 4.4 mmol) and the mixture refluxed for 1.5 h. The reaction mixture was cooled in an ice bath and fluorenylmethoxycarbonyl chloride (742 mg 2.2 mmol) was added in one portion. After stirring at 0° C. for 20 min the ice bath was removed and stirring was continued for 1.5 h. The reaction mixture was concentrated under reduced pressure and the residue stirred with a mixture of diethyl ether (20 ml) and saturated sodium carbonate solution (30 ml). A yellow solid which failed to dissolve in either layer was taken up in water (20 ml) and acidified to pH 1 with dilute hydrochloric acid. The mixture was then extracted with ethyl acetate and the organic layer washed with water (2×20 ml), dried with magnesium sulphate and evaporated to dryness. Recrystallisation from ethanol/water afforded (D,L)-N-fluorenylmethyloxycarbonyl-4-phenylphenylglycine (640 mg, 65%).

$^1$H nmr ($d_6$ DMSO) 8.25 (1H, d, aromatics); 7.89 (2H, d, aromatics); 7.76 (2H d, aromatics); 7.67 (3H, d, aromatics); 7.57-7.25 (6H, m, aromatics); 5.23 (1H, d, —NH); ~4.27 (3H, m, $H_\alpha$+$CH_2$).

Preparation of 3-Amidinobenzoic Acid TFA Salt

3 Cyanobenzoic acid (10 g, 68 mmol) was refluxed in ethanol (300 ml) on an isomantle fitted with reflux condenser and soxhlet extractor, the thimble being filled with A4 molecular sieve. Reflux was continued for 10 hours. The heating was then removed and the solution allowed to cool. The solution was then cooled in an ice bath and saturated with hydrogen chloride gas. The sealed flask was allowed to stand overnight then evaporated to dryness. To the dry product was added saturated ammonia/ethanol solution (400 ml) and the flask sealed and allowed to stand overnight. The solution was then evaporated to dryness and then treated with 2M sodium hydroxide solution (3 eq., 102 ml), the resulting solution was stirred for 2 hours then extracted with ethylacetate (100 ml). The aqueous layer was then acidified, with 10% aq hydrochloric acid (200 ml) in one lot and extracted with ethylacetate (100 ml). Concentrated ammonia solution was added to pH 14 and the solution cooled in the fridge overnight. The precipitate formed was filtered off and washed with water, dissolved in 10% TFA water and lyophilised to a white powder (12 g).

$^1$H nmr (D$_2$O) 8.40 (1H, s); 8.30 (1H, d, J=7.5 Hz); 8.00 (1H, d, J=7.5 Hz); 7.72 (1H, t).

Synthesis of Inhibitors

Method 1: Using a solid phase strategy on a Protein Technologies, Symphony Multiple Peptide Synthesiser by attachment of bis amino compounds to Peg-2-chlorotrityl chloride resin: 2-Chlorotrityl chloride resin was typically treated with greater than 2 fold excess of the di-amine in dry DCM The resin was further modified by the attachment of acids. Activation of Fmoc protected amino acid (2-5 eq) was by TBTU/DIPEA, all couplings minimum 120 min.) were carried out in DMF. Deprotection of the Fmoc group was achieved with 20% (v/v) piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% (v/v) triethylsilane in TFA, filtration, evaporation and trituration with diethylether.

Synthesis Using the Symphony Multiple Peptide Synthesiser.

The Symphony Multiple Peptide Synthesiser is charged with DMF, DCM, TBTU in DMF (450 mM), DIPEA in DMF (900 mM), 20% (v/v) piperidine in DMF. Resins are held in plastic reaction vessels that allow the introduction of reagents and solvents and nitrogen for agitation or air drying.

A typical synthesis cycle on the Symphony is as follows:

The reaction vessel containing the resin (0.1 mmol) is charged with the Fmoc protected amino acid (0.5 mmol) and then this is dissolved in DMF (2.5 ml), treated with TBTU (0.56 mmol, 1.25 ml) and DIPEA (1.1 mmol, 1.25 ml) and agitated with nitrogen for 2 hours (agitation times may vary). After coupling the resin is washed with DMF (6×5 ml) then deprotected with 20% (v/v) piperidine in DMF (2×5 ml for 1 min. each, then 1×5 ml for 8 min.) the resin is then washed with DMF (6×5 ml)

EXAMPLE 1

3-Amidino-benzoyl-D-phenylglycine 4-aminomethylcyclohexyl methylamide

Bis-1,4 aminomethylcyclohexane (2 ml) was added to 2 chlorotrityl chloride resin (1.2 mmol/g, 0.73 g) pre swollen in dry DCM (4 ml). After 2 h the resin was washed with DCM (6×5 ml), DMF (6×5 ml) and DCM (6×5 ml). The resin was then air dried to allow aliquots to be taken.

The bis-1,4-aminomethylcyclohexane 2-chlorotrityl chloride resin (0.1 mmol) was treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above.

HOBt (0.5 mmol, 68 mg) dissolved in DMF (4 ml) at 0° C. was treated with DIPCI (0.5 mmol, 80 µl), for 10 min. 3-amidinobenzoic acid TFA salt (0.5 mmol, 139 mg.) was added and stirring continued for 10 min. at room temperature. The mixture was transferred to the reaction vessel on the Symphony and agitated for 10 hours with nitrogen. The resin was washed with DMF (6×5 ml), DCM (6×5 ml) and air dried. The product was cleaved from the resin with 10% triethylsilane in TFA (10 ml) for 30 minutes, the resin filtered off and the TFA solution evaporated to dryness and triturated with diethyl ether to give the crude product. The crude product was dissolved in water (10 ml), filtered and purified by preparative reverse phase Hplc.

$^1$H nmr (D$_2$O) Mixture of cyclohexyl cis and trans isomers 8.09 (1H, s); 8.05 (1H, d, J=7.5 Hz); 7.90 (1H, d, J=7.5 Hz); 7.66 (1H, t, J=7.5 Hz); 7.43 (5H, m); 5.47 (1H, s); 3.05 (2H, m); 2.78 (2H, m); 1.48 (7H, m); 0.86 (3H, m) MS TOF 422 (M+1$^+$). Hplc (Jupiter5 C18, Gradient 1, water/acetonitrile/TFA) rt 13.45 min. (major) and 13.62 min. (minor).

Compounds made by the above method:

EXAMPLE 2

3-Amidino-benzoyl-DL-3-chloro-phenylglycine-4-aminomethylcyclohexyl methylamide $^1$H nmr (D$_2$O) Mixture of cyclohexyl cis and trans isomers 8.19 (1H, s); 8.15 (1H, d, J=7.5 Hz); 8.04 (1H, d, J=7.5 Hz); 7.90 (1H, t, J=7.5 Hz); 7.53 (4H, m); 5.63 (1H, s); 3.18 (2H, m); 2.90 (2H, m); 1.66 (7H, m); 1.00 (3H, m). (MS TOF 457 (M+1$^+$). Hplc (Jupiter5 C18, Gradient 2, water/acetonitrile/TFA) rt 16.53 min.

EXAMPLE 3

3-Amidino-benzoyl-DL-4-methoxyphenylglycine-4-aminomethylcyclohexyl methylamide $^1$H nmr (D$_2$O) Mixture of cyclohexyl cis and trans isomers 8.19 (1H, s); 8.12 (1H, d, J=7.5 Hz); 8.01 (1H, d, J-7.5 Hz); 7.80 (1H, t, J=7.5 Hz); 7.50, (2H, d); 7.10, (2H, d); 5.53 (1H, s); 3.86 (3H, s); 3.13 (2H, m); 2.90 (2H, m); 1.66 (7H, m); 0.95 (3H, m). (MS TOF 452 (M+1$^+$). Hplc (Jupiter5 C18, Gradient 2, water/acetonitrile/TFA) rt 13.87 min. (major) and 14.10 min. (minor).

EXAMPLE 4

3-Amidino-benzoyl-DL-4-hydroxyphenylglycine 4-aminomethylcyclohexyl methylamide $^1$H nmr (D$_2$O) Mixture of cyclohexyl cis and trans isomers 7.40 (1H, d); 7.25 (2H, dd); 7.08 (1H, d); 7.02 (1H, d); 6.88 (2H, m); 6.82 (1H, d); 5.28 (1H, d); 5.10 (1H, d); 3.03 (2H, m); 2.83 (2H, m); 1.50 (7H, m); 0.85 (3H, m). MS TOF 438 (M+1$^+$) Hplc (Jupiter5 C18, Gradient 2, water/acetonitrile/TFA) rt 9.69 min. (major) and 14.10 min. (minor).

EXAMPLE 5

3-Amidino-benzoyl-DL-1-naphthylglycine 4-aminomethylcyclohexyl methylamide $^1$H nmr (D$_2$O) Mixture of cyclohexyl cis and trans isomers 8.40, (1H, s); 8.25 (4H, 4); 8.132 (1H, d, J=7.5 Hz); 7.81 (4H, m); 6.53 (1H, s); 3.70-3.10 (2H, m); 2.99 (2H, m); 2.0-1.3 (7H, m); 1.07 (3H, m). (MS TOF 472 (M+1$^+$). Hplc (Jupiter5 C18, Gradient 2, water/acetonitrile/TFA) rt 17.62 min. (major) and 18.03 min. (minor).

EXAMPLE 6

3-Amidino-benzoyl-DL-4-phenyl Phenylglycine 4-aminomethylcyclohexyl methylamide $^1$H nmr (D$_2$O) Mixture of cyclohexyl cis and trans isomers 8.11 (2H, m); 7.94 (1H, d, J=7.5 Hz); 7.71 (5H, m);

7.51 (5H, m); 5.58 (1H, s); 3.3-2.90 (2H, m); 2.90-2.65 (2H, m); 1.8-1.2 (7H, m); 0.85 (3H, m). MS TOF 498 (M+1$^+$) Hplc (Jupiter5 C18, Gradient 2, water/acetonitrile/TFA) rt 19.37 min. (major), 21.69 min. (minor).

EXAMPLE 7

3-Amidino-benzoyl-DL-4-trifluoromethyl phenylglycine 4-aminomethylcyclohexyl methylamide $^1$H nmr (D$_2$O) Mixture of cyclohexyl cis and trans isomers 8.12 (1H, s); 8.07 (1H, d, J=7.5 Hz); 7.93 (1H, d, J=7.5 Hz); 7.8-7.6 (5H, m); 5.61 (1H, s); 3.30-2.70 (4H, m); 1.50 (7H, m); 0.85 (3H, m). MS TOF 490 (M+1$^+$) Hplc (Jupiter5 C18, Gradient 2, water/acetonitrile/TFA) rt 19.37 min.

EXAMPLE 8

3-Amidino-benzoyl-R,S-3-phenyl β-alanine 4-aminomethylcyclohexyl methylamide $^1$H nmr D$_2$O Mixture of cyclohexyl cis and trans isomers. 8.08 (2H, m); 7.96 (1H, d, J=7.5 Hz); 7.73 (1H, t, J=7.5 Hz); 7.44 (5H, m); 5.43 (1H, t, J=7.9 Hz); 3.50 (2H, m); 2.88 (4H, m); 1.6-1.0 (7H, m); 0.77 (2H, m). MS TOF 436 (M+1$^+$). Hplc (Jupiter5 C18, Gradient 2, water/acetonitrile/TFA) rt 13.22 min. (major), 13.61 (minor)

EXAMPLE 9

3-Amidino-benzoyl-DL-3-indolylglycine 4-aminomethylcyclohexyl methylamide $^1$H nmr (D$_2$O) Mixture of cyclohexyl cis and trans isomers 8.1-7.85 (3H, m); 7.65 (1H, m); 7.47 (4H, m); 7.33 (1H, m); 4.85 (m, partially obscured by solvent); 4.3.3.80 (4H, m); 3.05 (2H, m); 2.78 (3H, m); 1.8-1.0 (7H, m); 1.0-0.65 (3H, m). MS TOF 451 (M+1$^+$). Hplc (Jupiter5 C18, Gradient 2, water/acetonitrile/TFA) rt 10.12 min.

EXAMPLE 10

3-Amidino-benzoyl-DL-piperonylglycine 4-aminomethylcyclohexyl methylamide $^1$H nmr D$_2$O Mixture of cyclohexyl cis and trans isomers. 8.13 (2H, m); 8.00 (1H, d, J=7.5 Hz); 7.72 (1H, t, J=7.5 Hz); 6.96 (5H, m); 5.98 (2H, s); 5.44 (1H, s); 3.4-2.7 (4H, m); 1.9-1.25 (7H, m); 1.1-0.8 (3H, m). MS TOF 466 (M+1$^+$) Hplc (Kromasil C4, Gradient 2, water/acetonitrile/TFA) rt 12.62 min.

EXAMPLE 11

3-Amidino-benzoyl-DL-3-methyl phenylglycine 4-aminomethylcyclohexyl methylamide $^1$H nmr D$_2$O Mixture of cyclohexyl cis and trans isomers. 8.09 (2H, m); 7.96 (1H, d, J=7.5 Hz); 7.70 (1H, t, J=7.5 Hz); 7.25 (4H, m); 5.50 (1H, s); 3.4-2.7 (4H, m); 2.31 (3H, s); 1.9-1.1 (7H, m); 1.1-0.7 (3H, m). MS TOF 436 (M+1$^+$) Hplc (Kromasil C4, Gradient 2, water/acetonitrile/TFA) rt 14.41 min.

EXAMPLE 12

3-Amidino-benzoyl-DL-2-naphthylglycine 4-aminomethylcyclohexyl methylamide $^1$H nmr D$_2$O Mixture of cyclohexyl cis and trans isomers. 7.98 (2H, m); 7.83 (4H, m); 7.56 (1H, t, J=7.5 Hz); 7.45 (4H, m); 5.58 (1H, s); 3.25-2.55 (4H, m); 1.7-0.9 (7H, m); 0.9-0.5 (3H, m). MS TOF 472 (M+1$^+$) Hplc (Kromasil C4, Gradient 2, water/acetonitrile/TFA) rt 17.44 min. (major) 17.69 (minor).

EXAMPLE 13

3-Amidino-benzoyl-1-aminocyclopentane-N-4-aminomethylcyclohexyl methyl-1-carboxamide $^1$H nmr D$_2$O Mixture of cyclohexyl cis and trans isomers. 7.92 (2H, m); 7.81 (1H, d, J=7.5 Hz); 7.57 (1H, t, J=7.5 Hz); 3.6-3.1 (2H, m); 2.91 (2H, d, J=6.8 Hz); 2.68 (2H, d, J=6.8 Hz); 2.2-1.8 (4H, m); 1.8-1.2 (13H, m); 1.0-0.65 (3H, m). MS TOF 400 (M+1$^+$) Hplc (Kromasil C4, Gradient 2, water/acetonitrile/TFA) rt 10.87 min.

EXAMPLE 14

3-Amidino-benzoyl-DL-cyclohexylglycine 4-aminomethylcyclohexyl methylamide $^1$H nmr (D$_2$O) Mixture of cyclohexyl cis and trans isomers 8.10 (1H, s); 8.05 (1H, d, J=7.5 Hz); 7.85 (1H, d, J=7.5 Hz); 7.66 (1H, t, J=7.5 Hz); 4.25 (1H, d); 3.05 (2H, m); 2.78 (2H, m); 1.48-0.86 (19H, m) MS TOF 428 (M+1$^+$). Hplc (Jupiter5 C18, Gradient 2, water/acetonitrile/TFA) rt 14.76 min. (major) and 15.09 min. (minor).

EXAMPLE 15

3-Amidino-benzoyl-L-phenylglycine 4-aminomethylcyclohexyl methylamide

MS TOF 422 (M+1$^+$). Hplc (Jupiter5 C18, Gradient 2, water/acetonitrile/TFA) rt 10.06 min.

EXAMPLE 16

3-Amidino-benzoyl-D-phenylglycine 3-aminomethylcyclohexyl methylamide

MS TOF 422 (M+1$^+$). Hplc (Jupiter5 C18, Gradient 2, water/acetonitrile/TFA) rt 8.81 min.

EXAMPLE 17

3-Amidino-benzoyl-L-phenylglycine 3-aminomethylcyclohexyl methylamide

MS TOF 422 (M+1$^+$). Hplc (Jupiter5 C18, Gradient 2, water/acetonitrile/TFA) rt 8.79 min.

EXAMPLE 18

3-Amidino-benzoyl-DL-2-thienylglycine 4-aminomethylcyclohexyl methylamide

MS TOF 429 (M+1$^+$). Hplc (Jupiter5 C18, Gradient 2, water/acetonitrile/TFA) rt 12.73 min.

EXAMPLE 19

3-Amidino-benzoyl-DL-4-chloro-phenylglycine 4-aminomethylcyclohexyl methylamide

MS TOF 457 (M+1$^+$). Hplc (Jupiter5 C18, Gradient 2, water/acetonitrile/TFA) rt 15.89 min.

EXAMPLE 20

3-Amidino-benzoyl-D-phenylglycine 4-aminomethylbenzylamide

MS TOF 416 (M+1$^+$) Hplc (Techogel15 C18, Gradient 2, water/acetonitrile/TFA) rt 12.34 min.

EXAMPLE 21

3-Amidino-benzoyl-D-phenylglycine 3-aminomethylbenzylamide

MS TOF 416 (M+1$^+$) Hplc (Techogel15 C18, Gradient 2, water/acetonitrile/TFA) rt 9.65 min.

EXAMPLE 22

3-Amidino-benzoyl-L-phenylglycine 3-aminomethylbenzylamide

MS TOF 416 (M+1$^+$) Hplc (Techogel15 C18, Gradient 2, water/acetonitrile/TFA) rt 10.26 min.

EXAMPLE 23

3-Amidino-benzoyl-L-phenylglycine 4-aminomethylbenzylamide $^1$H nmr (D$_2$O) 8.10 (2H, m); 7.88 (1H, d, J=7.5 Hz); 7.65 (1H, t, J=7.5 Hz); 7.4-7.1 (9H, m); 5.57 (1H, s); 4.37 (2H, ABq); 4.06 (2H, s). MS TOF 416 (M+1$^+$) Hplc (Techogel15 C18, Gradient 1, water/acetonitrile/TFA) rt 12.34 min.

EXAMPLE 24

3-Amidino-benzoyl-D-phenylglycine-4-(4-aminocyclohexyl methyl) cyclohexylamide $^1$H nmr (D$_2$O) 8.3-7.95 (3H, m); 7.85-7.6 (2H, m); 7.47 (4H, m); 5.55 (1H, s); 3.59 (1H, m); 3.06 (1H, m); 2.1-1.5 (9H, m); 1.5-0.85 (11H, m). MS TOF 490 (M+1$^+$). Hplc (Kromasil C4, Gradient 2, water/acetonitrile/TFA) rt 18.30 min.

EXAMPLE 25

3-Amidino-benzoyl-L-phenylglycine-4-(4-aminocyclohexyl methyl) cyclohexylamide $^1$H nmr (D$_2$O) 8.3-7.95 (3H, m); 7.85-7.6 (2H, m); 7.47 (4H, m); 5.55 (1H, s); 3.59 (1H, m); 3.06 (1H, m); 2.1-1.5 (9H, m); 1.5-0.85 (11H, m). MS TOF 490 (M+1$^+$). Hplc (Kromasil C4, Gradient 2, water/acetonitrile/TFA) rt 18.39 min.

EXAMPLE 26

3-Amidino-benzoyl-D-phenylglycinyl-D-2-naphthylalanine-5-aminopentamide $^1$H nmr (d$_4$methanol) d 8.21 (1H, s); 8.14 (1H, d, J=7.5 Hz); 7.96 (1H, d, J=7.5 Hz); 7.80-7.65 (6H, m); 7.45-7.15 (7H, m); 5.66 (1H, s); 4.56 (1H, m); 3.16 (2H, m); 3.02 (2H, m); 2.68 (2H, m); 1.45 (2H, m); 1.32 (2H, m); 1.12 (2H, m). MS TOF 579 (M+1$^+$). Hplc (Jupiter5 C18, Gradient 1, water/acetonitrile/TFA) rt 13.56 min.

EXAMPLE 27

3-Amidino-benzoyl-D-phenylglycinyl D-lysine-5-aminopentamide $^1$H nmr (D$_2$O) d 8.10 (1H, s); 8.05 (1H, d, J=7.5 Hz); 7.94 (1H, d, J=7.5 Hz); 7.68 (1H, t, J=7.5 Hz); 7.45 (5H, m); 5.53 (1H, s); 4.22 (1H, t); 3.05 (2H, m); 2.90 (4H, dd); 1.8-1.0 (12H, m). MS TOF 510 (M+1$^+$). Hplc (Jupiter5 C18, Gradient 1, water/acetonitrile/TFA) rt 10.56 min.

EXAMPLE 28

3-Amidino-benzoyl-D-phenylglycine-5-aminopentamide $^1$H nmr (D$_2$O) d 7.85 (1H, s); 7.80 (1H, d, J=7.5 Hz); 7.70 (1H, d, J=7.5 Hz); 7.55 (1H, t, J=7.5 Hz); 7.20 (5H, m); 5.30 (1H, s); 3.05 (2H, m); 2.60 (2H, m); 1.25 (4H, m); 0.90, (2H, m); MS TOF 382 (M+1$^+$). Hplc (Jupiter5 C18, Gradient 2, water/acetonitrile/TFA) rt 11.26 min.

EXAMPLE 29

3-Amidino-benzoyl-D-phenylglycine-R,S-3-aminopyrrolidinamide $^1$H nmr (D$_2$O) 8.18 (1H, s); 8.10 (1H, d); 7.88 (1H, d); 7.70 (1H, t); 7.50 (5H, m); 5.55 (1H, s); 4.50 (1H, m); 3-4 (4H, m); 2.33 (1H, m); 2.00 (1H, m). MS TOF 366 (M+1$^+$). Hplc (Jupiter5 C18, Gradient 2, water/acetonitrile/TFA) rt 10.38+10.79 min.

EXAMPLE 30

3-Amidino-benzoyl-D-phenylglycine 4-aminomethyl piperidinamide

MS TOF 394 (M+1$^+$). Hplc (Jupiter5 C18, Gradient 2, water/acetonitrile/TFA) rt 11.40 min. (major) and 11.97 min. (minor).

Method 2: By solid phase strategy on a Protein Technologies, Symphony Multiple Peptide Synthesiser using Fmoc amino acids attached to Peg-2-chlorotrityl chloride resin: Typically the 2-chlorotrityl chloride resin was treated with a 2 fold excess of the Fmoc amino acid in a 1:1 mixture of DMF and dry DCM and DIPEA (2 eq.). The resin was washed with DMF/DCM and deprotected with 20% piperidine in DMF before further modification. The resin was further modified by the attachment of acids. Activation of Fmoc protected amino acids (2-5 eq) was by activation with TBTU/DIPEA, all couplings (minimum 120 min.) were carried out in DMF. Deprotection of the Fmoc group was achieved with 20% (v/v) piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% (v/v) triethylsilane in TFA, filtration, evaporation and trituration with ether.

EXAMPLE 31

3-Amidino-benzoyl-D-phenylglycinyl-D-2-naphthylalaninyl-glycine

Fmoc Glycine (0.2 mmol, 59 mg.) in DMF (2 ml) was added to 2 chlorotrityl chloride resin (1.0 mmol/g, 0.1 g) pre swollen in dry DCM (2 ml), then DIPEA (0.2 mmol). After 2 h the resin was washed with DCM (6×5 ml), DMF (6×5 ml) and DCM (6×5 ml). The resin was then air dried to allow aliquots to be taken for further modification.

On the Symphony Fmoc-Glycyl-2-chlorotrityl resin (0.1 mmol) was deprotected with 20% (v/v) piperidine in DMF and washed with DMF (6×5 ml) then treated with Fmoc-D-2-naphthylalanine (0.5 mmol 220 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above. The resin was then treated Fmoc-D-Phenylglycine (0.5 mmol 187 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above. HOBt (0.5 mmol, 68 mg) dissolved in DMF (4 ml) was stirred at 0° C. with DIPCI (0.5 mmol, 80 µl), for 10 min. 3-amidinobenzoic acid TFA salt (0.5 mmol, 139 mg.) was added and stirring continued for 10 min at room temperature. The mixture was transferred to the reaction vessel on the Symphony and agitated for 10 hours with nitrogen. The resin was then washed with DMF (6×5 ml), DCM (6×5 ml) and air dried. The product was cleaved from the resin with 10% (v/v) triethylsilane in TFA (10 ml) for 30 minutes, the resin filtered off, the TFA solution evaporated to dryness and triturated with diethyl ether to give the crude product. The crude product was then dissolved in water (10 ml), filtered and purified by preparative reverse phase Hplc.

$^1$H nmr (DMSO) d 8.15 (1H, s); 8.12 (1H, d, J=7.5 Hz); 7.85 (1H, d, J=7.5 Hz); 7.74 (5H, m); 7.65 (1H, t); 7.42-7.25 (7H, m); 5.73 (1H, s); 4.72 (1H, m); 3.75 (2H, d); signals at 3.3-3-0obscured by solvent. MS TOF 552 (M+1$^+$). Hplc (Jupiter5 C18, Gradient 1, water/acetonitrile/TFA) rt 14.88 min.

Compounds made by the above method:

EXAMPLE 32

3-Amidino-benzoyl-D-phenylglycinyl-D-2-naphthylalaninyl N-methylglycine $^1$H nmr (CD$_3$CN) mixture of rotomers, major product quoted. d 7.95 (2H, m); 7.87 (1H, d, J=7.5 Hz); 7.71 (4H, m); 7.62 (1H, t, J=7.5 Hz); 7.36 (3H, m); 7.22 (5H, m); 5.57 (1H, s); 5.19 (1H, dd); 3.95 (2H, ABq); 2.98 (3H, s) MS TOF 566 (M+1$^+$). Hplc (Jupiter5 C18, Gradient 1, water/acetonitrile/TFA) rt 14.86 min.

EXAMPLE 33

3-Amidino-benzoyl-D-phenylglycinyl-D-2-naphthylalaninyl-D-proline $^1$H nmr (CD$_3$CN) d 8.15 (1H, s); 8.08 (1H, d); 7.95 (1H, d); 7.82 (5H, m); 7.62, (1H, m); 7.22-7.5 (7H, m); 5.63 (1H, s); 5.05 (1H, m); 4.35 (1H, m); 3.60, (2H, m); signals at 3.3 obscured by solvent; 3.1-, (1H, m); 2.22, (1H, m); 2.0, (4H, m); MS TOF 592 (M+1$^+$). Hplc (Jupiter5 C18, Gradient 1, water/acetonitrile/TFA) rt 15.3.2 min.

Method 3: By solid phase strategy on a Protein Technologies, Symphony Multiple Peptide Synthesiser using Fmoc amino acids attached to TentaGel S-resin (Rapp Polymere) via the Rink amide linker: Typically the TentaGel resin was treated with a 5 fold excess of the Rink linker, TBTU (1 eq.), DIPEA (2 eq.). The resin was washed with DMF and deprotected with 20% piperidine in DMF before further modification. The resin was further modified by the attachment of acids. Activation of Fmoc protected amino acid (2-5 eq) was by TBTU/DIPEA, all couplings (minimum 120 min.) were carried out in DMF. Deprotection of the Fmoc group was achieved with 20% piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% triethylsilane in TFA, filtration, evaporation and trituration with ether.

EXAMPLE 34

3-Amidino-benzoyl-D-phenylglycinyl D-phenylalanine amide

On the Symphony TentaGel S—NH2 resin (0.1 mmol, 400 mg, 0.24 mmol./g) was treated with Rink linker (0.5 mmol, 270 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above.

On the Symphony Rink-TentaGel resin (0.1 mmol) was then treated with Fmoc-D-Phenylalanine-(0.5 mmol, 194 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above.

The resin (0.1 mmol) was then treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as above.

HOBt (0.5 mmol, 68 mg) dissolved in DMF (4 ml) was stirred at ice bath with DIPCI (0.5 mmol, 80 µl) for 10 min. 3-amidino-benzoic acid TFA salt (0.5 mmol, 139 mg.) was added and stirring continued for 10 min. at room temperature. The mixture was then transferred to the reaction vessel on the Symphony and agitated for 10 hours with nitrogen. The resin was then washed with DMF (6×5 ml), DCM (6×5 ml) and air dried. The product was cleaved from the resin with 10% triethylsilane in TFA (10 ml) for 30 minutes, the resin filtered off, the TFA solution evaporated to dryness and triturated with diethyl ether to give the crude product. The crude product was then dissolved in water (10 ml), filtered and purified by preparative reverse phase Hplc.

$^1$H nmr (d$_4$methanol) d 8.18 (1H, s); 8.10 (1H, d, J=7.5 Hz); 7.87 (1H, d, J=7.5 Hz); 7.72 (1H, t, J=7.5 Hz); 7.40 (5H, m); 7.10 (5H, m); 5.53 (1H, s); 4.55 (dd, partially obscured by solvent); 3.08 (1H, dd); 2.87 (1H, dd). MS TOF 444 (M+1$^+$). Hplc (Jupiter5 C18, Gradient 1, water/acetonitrile/TFA) rt 11.70 min.

Compounds made by the above method:

EXAMPLE 35

3-Amidino-benzoyl-D-phenylglycinyl-L-asparagine amide 1H nmr (D2O) d 8.10 (1H, s); 8.04 (1H, d, J=7.5 Hz); 7.91 (1H, d, J=7.5 Hz); 7.66 (1H, t, J=7.5 Hz); 7.42 (5H, m); 5.47 (1H, s); 4.73 (m, partially obscured by solvent); 2.71 (2H, m); 2.59 (2H, m). MS TOF 411 (M+1$^+$). Hplc (Jupiter5 C18, Gradient 2, water/acetonitrile/TFA) rt 10.49 min.

EXAMPLE 36

3-Amidino-benzoyl-D-phenylglycinyl-D-2-naphthylalanine amide $^1$H nmr (d$_4$methanol) d 8.18 (1H, s); 8.12 (1H, d, J=7.5 HZ); 7.95 (1H, d, J=7.5 Hz); 7.74 (5H, m); 7.42 (3H, m); 7.25 (5H, m); 5.63 (1H, s); 3.12 (1H, m); signals at ~4.8 and 3.3 obscured by solvent. MS TOF 494 (M+1$^+$). Hplc (Jupiter5 C18, Gradient 1, water/acetonitrile/TFA) rt 15.46 min.

EXAMPLE 37

3-Amidino-benzoyl-D-phenylglycinyl-D-valine amide $^1$H nmr (d$_4$methanol) d 8.44 (1H, s); 8.36 (1H, d, J=7.5 Hz); 8.10 (1H, d, J=7.5 Hz); 7.86 (1H, t, J=7.5 Hz) 7.70 (2H, m); 7.55 (3H, m); 5.96 (1H, s); 4.40 (1H d) 2.21 (1H, m); 1.13 (6H, t).). MS TOF 396 (M+1$^+$). Hplc (Jupiter5 C18, Gradient 1, water/acetonitrile/TFA) rt 5.71 min.

EXAMPLE 38

3-Amidino-benzoyl-D-phenylglycinyl-D-lysine amide $^1$H nmr (D$_2$O) d 8.10 (1H, s); 8.04) (1H, d, J=7.5 Hz); 7.95 (1H, d, J=7.5 Hz); 7.66 (1H, t, J=7.5 Hz); 7.43 (5H, m); 5.56 (1H, s); 4.26 (1H, m); 2.91 (2H, t); 1.77 (2H, m) 1.62 (2H, m); 1.42 (2H, m). MS TOF 425 (M+1$^+$). Hplc (Jupiter5 C18, Gradient 2, water/acetonitrile/TFA) rt 10.73 min.

EXAMPLE 39

3-Amidino-benzoyl-D-phenylglycinyl-L-lysine amide $^1$H nmr (D$_2$O) d 8.08 (1H, s); 8.00 (1H, d, J=7.5 Hz); 7.99 (1H, d, J=7.5 Hz); 7.61 (1H, t, J=7.5 Hz); 7.40 (5H, m); 5.52 (1H, s); 4.21 (1H, m); 2.68 (2H, m); 1.74 (1H, m); 1.60 (1H, m); 1.40 (2H, m); 1.08 (1H, m). MS TOF 425 (M+1$^+$). Hplc (Jupiter5 C18, Gradient 2, water/acetonitrile/TFA) rt 10.61 min.

EXAMPLE 40

3-Amidino-benzoyl-D-phenylglycinyl-D,L-phenylglycinyl-L-valine amide $^1$H nmr (CD$_3$CN) mixture of diastereomers d 8.39 (1H, m); 8.15 (1H, m); 7.93 (1H, m); 7.70 (1H, m); 7.41 (10H, m); 5.71 (1H, d); 5.46 (1H, m); 4.14 (1H, m); 2.77 (1H, m); 0.97 (3H, m); 0.65 (3H, m). MS TOF 529 (M+1$^+$). Hplc (Jupiter5 C18., Gradient 1, water/acetonitrile/TFA) rt 13.10 min.

EXAMPLE 41

3-Amidino-benzoyl-D-phenylglycinyl-D-asparagine-D-asparagine amide $^1$H nmr (D$_2$O) d 8.28 (1H, s); 8.20 (1H, d, J=7.5 Hz); 8.08 (1H, d, J=7.5 Hz); 7.82 (1H, t, J=7.5 Hz); 7.59 (5H, m); 5.72 (1H, s); 4.70 (1H, dd); 2.85 (4H, m). MS TOF 526 (M+1$^+$). Hplc (Jupiter5 C18, Gradient 2, water/acetonitrile/TFA) rt 11.14 min.

EXAMPLE 42

3-Amidino-benzoyl-D-phenylglycinyl-D-leucine amide $^1$H nmr (CD$_3$CN) d 8.23 (1H, s); 8.14 (1H, d, J=7.5 Hz); 7.93 (1H, d, J=7.5 Hz); 7.72 (1H, t, J=7.5 Hz); 7.48 (5H, m); 5.62 (1H, s); 4.32 (1H, m); 1.58 (2H, m); 0.87 (6H, dd). MS TOF 410 (M+1$^+$). Hplc (Jupiter5 C18, Gradient 2, water/acetonitrile/TFA) rt 14.98 min.

EXAMPLE 43

3-Amidino-benzoyl-D-phenylglycinyl-L-phenylalanine amide $^1$H nmr (CD$_3$CN) d 8.20 (1H, s); 8.14 (1H, d, J=7.5 Hz); 7.96 (1H, d, J=7.5 Hz); 7.72 (1H, t, J=7.5 Hz); 7.35 (5H, m); 7.14 (3H, m); 7.04 (2H, m); 5.60 (1H, s); 5.46 (1H, dd); 3.15 (1H, dd); 2.80 (1H, m). MS TOF 444 (M+1$^-$). Hplc (Jupiter5 C18, Gradient 1, water/acetonitrile/TFA) rt 12.78 min.

EXAMPLE 44

3-Amidino-benzoyl-D-phenylglycinyl-L-2-naphthylalanine amide $^1$H nmr (d$_4$methanol) d 8.26 (1H, s); 8.19 (1H, d, J=7.5 Hz); 7.95 (1H, d, J=7.5 Hz); 7.80 (1H, m); 7.67 (3H, m); 7.53 (1H, s); 7.45 (2H, m); 7.25 (1H, d); 7.08 (3H, m); 6.92 (2H, t); 5.61 (1H, s); 3.45 (1H, m); 3.0 (1H, m) signal at ~4.8 obscured by solvent. MS TOF 494 (M+1$^+$). Hplc (Jupiter5 C18, Gradient 1, water/acetonitrile/TFA) rt 16.17 min.

EXAMPLE 45

3-Amidino-benzoyl-D-phenylglycinyl-L-valine amide $^1$H nmr (CD$_3$CN) d 8.17 (1H, s); 8.08 (1H, d, J=7.5 Hz); 7.89 (1H, d, J=7.5 Hz); 7.65 (1H, t, J=7.5 Hz); 7.37 (5H, m); 5.64 (1H, s); 4.08 (1H d); 1.97 (m, partially obscured by solvent); 0.63 (6H, t). MS TOF 396 (M+1$^+$). Hplc (Jupiter5 C18, Gradient 2, water/acetonitrile/TFA) rt 9.34 min.

EXAMPLE 46

3-Amidino-benzoyl-D-phenylglycinyl-D-asparagine amide $^1$H nmr (D$_2$O) d 7.91 (1H, s); 7.86 (1H, d, J=7.5 Hz); 7.63 (1H, d, J=7.5 Hz); 7.48 (1H, t, J=7.5 Hz); 7.23 (5H, m); 5.30

(1H, s); 4.42 (m, partially obscured by solvent); 2.57 (2H, m). MS TOF 411 (M+1⁺). Hplc (Jupiter5 C18, Gradient 2, water/acetonitrile/TFA) rt 10.23 min.

EXAMPLE 47

3-Amidino-benzoyl-L-phenylglycinyl-D-2-naphthylalanine amide

¹H nmr (CD$_3$CN/D$_2$O) 8.17 (1H, s); 8.10 (1H, d); 7.92 (1H, d); 7.81 (1H, m); 7.67 (3H, m); 7.53 (1H, s); 7.48 (2H, m); 7.22 (1H, d); 7.12 (3H, m); 6.98 (2H, m); 5.56 (1H, s); 4.70 (1H, dd); 3.35 (1H, dd); 3.00 (1H, dd). MS TOF 494 (M+1⁺). Hplc (Jupiter5 C18, Gradient 1, water/acetonitrile/TFA) rt 15.46 min.

EXAMPLE 48

3-Amidino-benzoyl-L-phenylglycinyl-L-2-naphthylalanine amide

¹H nmr (CD$_3$CN) 8.07 (1H, s); 8.01 (1H, d); 7.92 (1H, d); 7.78 (1H, m); 7.66 (2H, s); 7.41 (4H, m); 7.14 (6H, d); 5.46 (1H, s); 4.73 (1H, dd); 3.38 (1H, dd); 3.08 (1H, dd). MS TOF 494 (M+1⁺). Hplc (Jupiter5 C18, Gradient 1, water/acetonitrile/TFA) rt 14.51 min.

EXAMPLE 49

3-Amidino-benzoyl-D-phenylglycinyl-D-4-chloro phenylalanine amide

¹H nmr (CD$_3$CN) d 8.39 (1H, s); 8.32 (1H, d, J=7.5 Hz) 8.13 (1H, d, J=7.5 Hz); 7.90 (1H, t, J=7.5 Hz); 7.51 (5H, m); 7.40 (4H, ABq); 5.70 (1H, s); 4.77 (1H, dd); 3.36 (1H, dd); 3.09 (1H, dd). MS TOF 479 (M+1⁺). Hplc (Jupiter5 C18, Gradient 2, water/acetonitrile/TFA) rt 13.63 min.

EXAMPLE 50

3-Amidino-benzoyl-D-phenylglycinyl-D-isoleucine amide

MS TOF 410 (M+1⁺). Hplc (Jupiter5 C18, Gradient 2, water/acetonitrile/TFA) rt 14.36 min.

EXAMPLE 51

3-Amidino-benzoyl-D-phenylglycinyl-D-tyrosine amide

MS TOF 460 (M+1⁺). Hplc (Jupiter5 C18, Gradient 2, water/acetonitrile/TFA) rt 12.56 min.

EXAMPLE 52

3-Amidino-benzoyl-D-phenylglycinyl-D-1-naphthylalanine amide

MS TOF 494 (M+1⁺). Hplc (Jupiter5 C18, Gradient 2, water/acetonitrile/TFA) rt 22.19 min.

EXAMPLE 53

3-Amidino-benzoyl-D-phenylglycinyl-D-threonine amide

MS TOF 398 (M+1⁺). Hplc (Jupiter5 C18, Gradient 2, water/acetonitrile/TFA) rt 10.63 min.

EXAMPLE 54

3-Amidino-benzoyl-D-phenylglycinyl-D-histidine amide

MS TOF 434 (M+1⁺). Hplc (Jupiter5 C18, Gradient 2, water/acetonitrile/TFA) rt 10.04 min.

EXAMPLE 55

3-Amidino-benzoyl-D-phenylglycinyl-D-phenylalanine amide

MS 444 TOF (M+1⁺). Hplc (Jupiter5 C18, Gradient 2, water/acetonitrile/TFA) rt 14.82 min.

EXAMPLE 56

3-Amidino-benzoyl-D-phenylglycinyl-D-phenylaninyl D-proline amide

MS TOF 541 (M+1⁺). Hplc (Jupiter5 C18, Gradient 2, water/acetonitrile/TFA) rt 11.54 min.

EXAMPLE 57

3-Amidino-benzoyl-D-phenylglycinyl-D-tryptophan amide

MS TOF 483 (M+1⁺). Hplc (Jupiter5 C18, Gradient 2, water/acetonitrile/TFA) rt 17.14 min.

Method 4: By solution phase strategy: Typically an activated Boc-amino acid was treated with an amine (primary or secondary) or alcohol (1 eq.). Activation of Boc protected amino acid was by HATU or TBTU/DIPEA (1:2), all couplings (minimum 120 min.) were carried out in DMF. After an aqueous work up the deprotection of the Boc group was achieved with TFA. Other acid substituents were added as the HOBt or HOAt esters either by activation with HBTU/HATU or DIPCI with or without Boc protection of amino groups. The final products were purified by preparative reverse phase Hplc.

EXAMPLE 58

3-Amidino-benzoyl-D-phenylglycine-1-adamantylamide

Boc D-phenylglycine (251 mg, 1 mmol.) was dissolved in DMF (3 ml) with HATU (380 mg., 1 mmol.) and DIPEA (350 μl., 2 mmol.). To this mixture was added 1-adamantylamine hydrochloride (187 mg., 1 mmol.) and DIPEA (170 μl., 1 mmol.). The mixture was stirred overnight. The mixture was then taken up into ethylacetate and washed with water, sodium carbonate solution, water, 10% hydrochloric acid solution and water. The ethylacetate was evaporated without drying and treated immediately with TFA for 30 min. The TFA was then evaporated to dryness and the product triturated with diethylether. TEA (1 ml) was added and evaporated to dryness. HOBt (1 mmol, 136 mg) dissolved in DMF (4 ml) was stirred at 0° C. and treated with DIPCI (1 mmol, 160 μl), for 10 min. 3 amidino benzoic acid TFA salt (1 mmol., 278 mg.) was added and stirring continued for 10 min. at room temperature. The mixture was then added to the D-phenylglycine adamantyl amide and stirred overnight. The crude product was dissolved in water/acetonitrile (20 ml), filtered and purified by preparative Hplc to yield pure product (150 mg.)

$^1$H nmr (D$_2$O/CD$_3$CN) 8.21 (1H, s); 8.13 (1H, d, J=7.5 Hz) 7.92 (1H, d, J=7.5 Hz); 7.70 (1H, t, J=7.5 Hz)); 7.46 (2H, m); 7.34 (3H, m); 5.52 (1H, s); 2.15-1.52 (15H, m). M.S. TOF 431 (M+1$^+$). Hplc (Jupiter5 C18, Gradient 1, water/acetonitrile/TFA) rt 19.54 min.

Compounds made by the above method:

EXAMPLE 59

3-Amidino-benzoyl-D-phenylglycine-1-adamantyl-methylamide $^1$H nmr (D$_2$O/CD$_3$CN) 8.23 (1H, s); 8.15 (1H, d, J=7.5 Hz) 7.85 (1H, d, J=7.5 Hz); 7.71 (1H, t, J=7.5 Hz); 7.46 (2H, m) 7.35 (3H, m); 5.59 (1H, d); 3.0 (2H, s obscured by solvent); 2.15-1.52 (15H, m). M.S. TOF 445 (M+1$^+$). Hplc (Jupiter5 C18, Gradient 1, water/acetonitrile/TFA) rt 21.35 min.

EXAMPLE 60

3-Amidino-benzoyl-D-phenylglycine-2-phenylethylamide $^1$H nmr (d$_4$ methanol) 8.18 (2H, m); 7.87 (1H, d, J=7.5 Hz) 7.60 (1H, t, J=7.5 Hz); 7.30 (5H, m); 7.02 (5H, m); 5.53 (1H, s); 3.32 (1H, m); 1H signal at ~3.25 obscured by solvent); 2.68 (2H, t). M.S. TOF 401 (M+1$^+$). Hplc (Kromasil C4, Gradient 1, water/acetonitrile/TFA) rt 15.56 min.

EXAMPLE 61

3-Amidino-benzoyl-D-phenylglycine-2-(1-adamantyl) ethyl ester $^1$H nmr (d$_4$ methanol) 8.27 (2H, m); 7.94 (1H, d J=7.5 Hz); 7.72 (1H, t, J=7.5 Hz); 7.42 (5H, m); 5.66 (1H, s); 4.25 (2H, m); 1.82 (3H, s); 1.61 (6H, m); 1.38 (8H, m). M.S. TOF 459 (M+1$^+$). Hplc (Kromasil C4, Gradient 1, water/acetonitrile/TFA) rt 23.17 min.

EXAMPLE 62

3-Amidino-benzoyl-D-phenylglycine-2-methylbenzylamide $^1$H nmr (CD$_3$CN) 8.14 (2H, m); 7.88 (1H, d, J=7.5 Hz); 7.65 (1H, t, J=7.5 Hz); 7.45 (2H., m); 7.35 (3H, m); 7.04 (4H, m); 5.59 (1H, s); 4.30 (2H, AB q); 2.13 (3H, s). MS. TOF 401 (M+1$^+$). Hplc (Jupiter5 C18, Gradient 1, water/acetonitrile/TFA) rt 14.81 min.

EXAMPLE 63

3-Amidino-benzoyl-D-phenylglycine-4-benzoyl piperidinamide $^1$H nmr (DMSO) 8.40 (2H, m); 8.10 (1H, d); 7.70, (1H, t); 7.50 (10H, m); 5.55 (1H, s); 3.60 (1H, m); 2.5 (2H, m); .1.00, (6H, m); .S. TOF 469 (M+1$^+$) .Hplc (Jupiter5 C18, Gradient 1, water/acetonitrile/TFA) rt 11.43 min.

EXAMPLE 64

3-Amidino-benzoyl-D-phenylglycine-4-methylbenzylamid $^1$H nmr (CD$_3$CN) 8.30 (1H, s); 8.22 (1H, d, J=7.5 Hz); 7.95 (1H, d, J=7.5 Hz); 7.71 (1H, t, J=7.5 Hz); 7.51 (2H., m); 7.34 (3H, m); 7.04 (4H, s); 5.76 (1H, s); 4.30 (2H, AB q); 2.30 (3H, s). M.S. TOF 401 (M+1$^+$). Hplc (Jupiter5 C18, Gradient 1, water/acetonitrile/TFA) rt 15.20 min.

EXAMPLE 65

3-Amidino-benzoyl-D-phenylglycine-1-naphthylmethylamide $^1$H nmr (CD$_3$CN/D$_2$O) 8.14 (1H, s); 8.02 (1H, d, J=7.5 Hz); 7.84 (3H, m); 7.60 (1H, d, J=7.5 Hz); 7.32 (5H, m, J=7.5 Hz); 7.12 (5H., m); 5.58 (1H, s); 4.50 (2H, AB q); 3.03 (2H, s). M.S. TOF 436 (M+1$^+$). Hplc (Jupiter5 C18, Gradient 1, water/acetonitrile/TFA) rt 16.77 min.

EXAMPLE 66

3-Amidino-benzoyl-D-phenylglycinyl-D-phenylalanine-N-pyrrolidinamide $^1$H nmr (CD$_3$CN/D$_2$O) 8.14 (1H, s); 8.03 (1H, d, J=7.5 Hz); 7.94 (1H, d, J=7.5 Hz); 7.70 (1H, t, J=7.5 Hz); 7.42 (5H, m); 7.42 (5H., m); 5.62 (1H, s); 4.80 (1H, t); 3.40 (1H, m); 3.20 (2H, m); 3.02, (2H, d); 2.80 (1H, m); 1.65, (4H, m); . M.S. TOF 499 (M+1$^+$). Hplc (Jupiter5 C18, Gradient 1, water/acetonitrile/TFA) rt 14.03 min.

EXAMPLE 67

3-Amidino-benzoyl-D-phenylglycine-3-methylbenzylamide $^1$H nmr (CD$_3$CN) 7.95 (1H, s); 7.81 (1H, d, J=7.5 Hz); 7.60 (1H, d, J=7.5 Hz); 7.45 (1H, t, J=7.5 Hz); 7.23 (2H., m); 7.12 (3H, m); 6.60-6.75 (4H, m); 5.40 (1H, s); 4.10 (2H, AB q); 1.95 (3H, s). M.S. TOF 401 (M+1$^+$). Hplc (Jupiter5 C18, Gradient 1, water/acetonitrile/TFA) rt 14.52 min.

EXAMPLE 68

3-Amidino-benzoyl-D-phenylglycine-2adamantylamide

MS TOF 431 (M+1$^+$). Hplc (Jupiter5 C18, Gradient 3, water/acetonitrile/TFA) rt 12.68 min.

Method 5: By solid phase strategy using Boc amino acids attached to Kaiser Oxime resin (Novabiochem): Typically the resin is treated with a 2 fold excess of the Boc phenylglycine symmetrical anhydride. The resin was washed with DCM/DMF then DCM and deprotected with 25% TFA in DCM before further modification. The resin was further modified by the attachment of acids. Activation of Boc protected amino acid (2-5 eq) was by TBTU/DIPEA, all couplings (minimum 120 min.) were carried out in DCM/DMF. Deprotection of the Boc group was achieved with 25% TFA in DCM. Other acid substituents were added as the HOBt or HOAt esters either by activation with HBTU/HATU or DIPCI with or without Boc protection of amino groups. Cleavage of the products from the resin was by treatment (1 day, ambient) with an amine or alcohol in chloroform, washing with chloroform and methanol/chloroform.

EXAMPLE 69

3-Amidino-benzoyl-D-phenylglycine cyclohexyl amide

Boc-D-Phenylglycine (0.5 mmol, 126 mg) was dissolved in DCM (5 ml) and treated with DIPCI (0.5 mmol., 80 µl) and stirred for 10 min. A white precipitate forms which was dissolved by adding DMF. This mixture was added to Oxime resin (0.11 mmol, 330 mg, 0.33 mmol./g) previously swelled with DCM. 4-Dimethyl amino pyridine (10 mg, cat.) was added and the mixture swirled for 2 hours. The resin was filtered and washed with DMF/DCM then DCM. The resin was then treated with 25% TFA/DCM (20 ml) for 20 min., filtered and washed with DCM. HOBt (0.5 mmol, 68 mg) dissolved in DMF (4 ml) was stirred at 0° C. with DIPCI (0.5 mmol, 80 µl) for 10 min. 3 amidino-benzoic acid TFA salt (0.5 mmol, 139 mg.) was added and stirring continued for 10 min. at room temperature. The mixture was then added to the phenylglycine-oxime resin and agitated for 2 hours. The resin was filtered washed with DMF, DCM and chloroform then treated with cyclohexylamine (0.3 mmol. 40 µl) in chloroform (2 ml) and agitated for 1 day. The resin was then filtered off and washed with chloroform (10 ml) and chloroform/methanol (1:1, 10 ml). The combined organic extracts were evaporated to dryness and washed with 10% aqueous acetic acid (5-10 ml). The aqueous insoluble residue was dissolved in acetonitrile/water and lyophilised.

MS TOF 379 (M+1$^+$). Hplc (Jupiter5 C18, Gradient 3, water/acetonitrile/TFA) rt 10.62 min.

EXAMPLE 70

3-Amidino-benzoyl-D-phenylglycine-3,3-dimethyl-butylamide

MS TOF 382 (M+1$^+$). Hplc (Jupiter5 C18, Gradient 3, water/acetonitrile/TFA) rt 13.90 min.

EXAMPLE 71

3-Amidino-benzoyl-D-phenylglycine-1,2,3,4-tetrahydro-1-naphthylamide

MS TOF 427 (M+1$^+$). Hplc (Jupiter5 C18, Gradient 3, water/acetonitrile/TFA) rt 11.74 min.

EXAMPLE 72

3-Amidino-benzoyl-D-phenylglycine-R,S 3-methyl-2-butylamide

MS TOF 367 (M+1$^+$). Hplc (Jupiter5 C18, Gradient 3, water/acetonitrile/TFA) rt 10.21+10.42 min.

EXAMPLE 73

3-Amidino-benzoyl-D-phenylglycine-3-phenylpropylamide

MS TOF 415 (M+1$^+$). Hplc (Jupiter5 C18, Gradient 3, water/acetonitrile/TFA) rt 14.00 min.

EXAMPLE 74

3-Amidino-benzoyl-D-phenylglycine-3-trifluoromethyl benzylamide

MS TOF 455 (M+1$^+$). Hplc (Jupiter5 C18, Gradient 3, water/acetonitrile/TFA) rt 14.32 min.

EXAMPLE 75

3-Amidino-benzoyl-D-phenylglycine-3-fluorobenzylamide

MS TOF 405 (M+1$^+$). Hplc (Jupiter5 C18, Gradient 3, water/acetonitrile/TFA) rt 12.56 min.

EXAMPLE 76

3-Amidino-benzoyl-D-phenylglycine-2-methyl propylamide

MS TOF 353 (M+1$^+$). Hplc (Jupiter5 C18, Gradient 3, water/acetonitrile/TFA) rt 11.10 min.

EXAMPLE 77

3-Amidino-benzoyl-D-phenylglycine-4-phenyl butylamide

MS TOF 429 (M+1$^+$). Hplc (Jupiter5 C18, Gradient 3, water/acetonitrile/TFA) rt 14.96 min.

EXAMPLE 78

3-Amidino-benzoyl-D-phenylglycine-cyclohexylmethylamide

MS TOF 493 (M+1$^+$). Hplc (Jupiter5 C18, Gradient 3, water/acetonitrile/TFA) rt 11.52 min.

EXAMPLE 79

3-Amidino-benzoyl-D-phenylglycine-2,2 diphenylethylamide

MS TOF 478 (M+1$^+$). Hplc (Jupiter5 C18, Gradient 3, water/acetonitrile/TFA) rt 12.65 min.

EXAMPLE 80

3-Amidino-benzoyl-D-phenylglycine-R-1-(1-naphthyl)ethylamide

MS TOF 450 (M+1$^+$). Hplc (Jupiter5 C18, Gradient 3, water/acetonitrile/TFA) rt 12.26 min.

EXAMPLE 81

3-Amidino-benzoyl-D-phenylglycine-S-1-(2-naphthyl)ethylamide

MS TOF 450 (M+1$^+$). Hplc (Jupiter5 C18, Gradient 3, water/acetonitrile/TFA) rt 11.19 min.

Method 6: By solution phase strategy: Typically an activated Fmoc amino acid was treated with an alcohol (1 eq.) which contains a Boc protected amino group. Activation of Fmoc protected amino acid was by HATU or TBTU/DIPEA (1:2), all couplings (minimum 120 min.) were carried out in DMF with DBU as catalyst After an aqueous work up the deprotection of the Fmoc group was achieved with 20% piperidine in DMF followed by evaporation and column chromatography. Other acid substituents were added as the HOBt or HOAt esters either by activation with HBTU/HATU or DIPCI with or without Boc protection of amino groups. The products were purified by preparative reverse phase Hplc, followed by deprotection of the amino groups with TFA. Further modification to acetamidine or amidine can be achieved by known literature methods. (2,3)

EXAMPLE 82

3-Amidino-benzoyl-D-phenylglycine-(4-piperidinyl) methyl ester

Fmoc D-Phenylglycine (1 mmol., 374 mg) was dissolved in DMF (5 ml) with HATU (1 mmol., 380 mg) and DIPEA (2 mmol., 350 µl). To this mixture was added N-Boc 4-hydroxymethyl piperidine (215 mg, 1 mmol.) and DBU (100 µl). The mixture was stirred overnight. The mixture was then taken up into ethylacetate (50 ml) and washed with water, sodium carbonate solution, water, 10% hydrochloric acid solution and water. The ethylacetate layer was dried over magnesium sulphate, filtered and evaporated. The product was then treated with 20% piperidine in DMF for 90 min. this was then evaporated to dryness and then dissolved in methanol and adsorbed onto silica gel 60. The material was then chromatographed on silica gel 60, eluting first with hexane/ethylacetate (2:1) then hexane/ethylacetate (1:2), the required product eluting in the second solvent. The combined fractions were evaporated to dryness. HOBt (1 mmol, 136 mg) dissolved in DMF (4 ml) was stirred at 0° C. with DIPCI (1 mmol, 160 µl) for 10 min. 3 amidino-benzoic acid TFA salt (1 mmol., 278 mg.) was added and stirring continued for 10 min. at room temperature. The mixture was then added to the D-phenylglycine N-Boc-4-piperidine methyl ester and stirred overnight. The mixture was evaporated to dryness on high vacuum, water and acetonitrile added to allow full dissolution and the whole lyophilised. The resulting crude product was treated with TFA/water (9:1) for 30 min. and evaporated to dryness. The crude product was dissolved in water/acetonitrile (20 ml), filtered and purified by preparative reverse phase Hplc. Producing pure product (200 mg).

$^1$H nmr (D$_2$O) 8.12, (1H,m); 8.05 (1H, d); 7.90 (1H, d) 7.65 (1H, t); 7.45 (5H, m); 5.65, (1H, s); 4.10, (2H,d); 3.30 (2H,m); 2.80 (2H, m); 1.90 (1H, m); 1.75 (2H, m); 1.30 (2H, m); MS TOF 395 (M+1$^+$). Hplc (Jupiter5 C18, Gradient 2, water/acetonitrile/TFA) rt 12.48 min.

Compounds made by the above method:

EXAMPLE 83

3-Amidino-benzoyl-D-phenylglycine-2-(4-piperidinyl) ethyl ester $^1$H nmr (D$_2$O) 8.12, (1H,m); 8.05 (1H, d); 7.90 (1H, d) 7.65 (1H, t); 7.45 (5H, m); 5.65, (1H,s); 4.25, (2H,m); 3.20 (2H,m); 2.60 (2H, m); 1.65 (2H, m); 1.50 (2H, m); 1.20 (3H, m); MS TOF 409 (M+1$^+$). Hplc (Jupiter5 C18, Gradient 2, water/acetonitrile/TFA) rt 13.14 min.

EXAMPLE 84

3-Amidino-benzoyl-D-phenylglycine-2-(N-acetimino-4-piperidinyl) ethyl ester $^1$H nmr (D$_2$O) 8.22, (1H,m); 8.20 (1H, d); 8.02 (1H, d) 7.80 (1H, t); 7.60 (5H, m); 5.75, (1H, s); 4.35, (2H,m) 3.85 (2H,m); 3.00 (3H, m); 2.30 (3H,s); 1.65 (3H, m); 1.50 (1H, m); 1.20 (2H, m); MS TOF 450 (M+1$^+$). Hplc (Jupiter5 C18, Gradient 2, water/acetonitrile/TFA) rt 14.92 min.

EXAMPLE 85

3-Amidino-benzoyl-D-phenylglycine-(N-acetimino-4-piperidinyl) methyl ester $^1$H nmr (D$_2$O) 8.12, (1H,m); 8.05 (1H, d); 7.90 (1H, d); 7.65 (1H, t); 7.40 (5H, m); 5.60, (1H, s); 4.05, (2H,m) 3.75 (2H, m); 3.10 (1H, m); 2.10 (3H, d); 1.90 (1H, m) 1.60 (2H, m); 1.20 (2H, m); 0.90 (1H,m); MS TOF 436 (M+1$^+$). Hplc (Jupiter5 C18, Gradient 2, water/acetonitrile/TFA) rt 13.34 min.

EXAMPLE 86

3-Amidino-benzoyl-D-phenylglycine-(N-amidino-4-piperidinyl) methyl ester $^1$H nmr (D$_2$O) 8.02, (1H,m); 7.97 (1H, d); 7.80 (1H, d) 7.55 (1H, t); 7.40 (5H, m); 5.55, (1H, s); 4.05, (2H,m) 3.65 (2H,m); 2.80 (2H, m); 1.80 (1H,m); 1.50 (2H, m); 1.10 (1H, m); 0.80 (1H,m); MS TOF 437 (M+1$^+$). Hplc (Jupiter5 C18, Gradient 2, water/acetonitrile/TFA) rt 13.61 min.

EXAMPLE 87

3-Amidino-benzoyl-D-phenylglycine-2-(N-amidino-4-piperidinyl) ethyl ester $^1$H nmr (D$_2$O) 8.17, (1H,m); 8.07 (1H, d); 7.93 (1H, d) 7.70 (1H, t); 7.45 (5H, m); 5.60, (1H, s); 4.25, (2H,m) 3.55 (2H,m); 2.75 (2H, m); 1.60 (4H,m); 1.25 (1H, m); 1.00 (2H, m); MS TOF 451 (M+1$^+$). Hplc (Jupiter5 C18, Gradient 2, water/acetonitrile/TFA) rt 14.97 min.

EXAMPLE 88

2-Hydroxy-5-amidino-benzoyl D-phenylglycine-4-aminomethylcyclohexyl methylamide

5-Bromosalicylic acid (9.31 mmol., 2.02 g) was dissolved in DMF (4.5 ml) and treated with copper (1) cyanide (11.33 mmol., 1.2 eq., 1.015 g) and heated under reflux for 4 hours. The solution was allowed to cool and poured into a solution of ferric chloride (2 g) and concentrated hydrochloric acid (0.7 ml) in water (3 ml). The mixture was heated for 10 min. at 60° C., then cooled and filtered, the solid was washed with water, then recrystallised ethanol/water. Product 0.73 g, 48%.

On the Symphony bis-1,4-aminomethylcyclohexane 2 chlorotrityl chloride resin (0.1 mmol) (See method 1) was treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution) and agitated with nitrogen for 2 hours. Deprotection and washing as above.

HOBt (0.5 mmol, 68 mg) dissolved in DMF (4 ml) was stirred at 0° C. with DIPCI (0.5 mmol, 80 µl) for 10 min. 2-hydroxy-5-cyanobenzoic acid (0.5 mmol, 84 mg.) was added and stirring continued for 10 min. at room temperature. The mixture was then transferred to the reaction vessel on the Symphony and agitated for 10 hours with nitrogen. The resin was washed with DMF (6×5 ml), DCM (6×5 ml) and air dried. The product was cleaved from the resin with 10% triethylsilane in TFA (10 ml) for 30 minutes, the resin filtered off, the TFA solution evaporated to dryness and triturated with diethyl ether to give the crude product. The crude product was dissolved in saturated hydrogen chloride in ethanol (10 ml), sealed and allowed to stand overnight. The solution was evaporated to dryness and treated with saturated ammonia in ethanol (10 ml) and allowed to stand overnight. The solution was then evaporated to dryness, dissolved in water and purified by reverse phase Hplc.

$^1$H nmr (D$_2$O), 8.35, (1H,s); 7.90, (1H,d); 7.55, (5H,m) 7.25, (1H,d); 5.65 (1H, s); 3.20 (2H, m); 2.90 (2H, m) 1.40-1.80 (7H, m); 0.95 (3H, m) MS TOF 438 (M+1$^+$). Hplc (Techogel5 C18, Gradient 2, water/acetonitrile/TFA) rt 14.11 min.

EXAMPLE 89

2-Amino-5-amidinobenzoyl-D-phenylglycine-4-aminomethylcyclohexyl methylamide

2-Amino-5-bromo benzoic acid (1.6 mmol., 345 mg) was dissolved in N-methylpyrrolidone (5 ml) and treated with copper (1) cyanide (2.39 mmol., 1.5 eq., 207 mg) under reflux for 4.5 hours. The solution was allowed to cool and poured into water (10 ml). The mixture was acidified to pH3 with hydrochloric acid and extracted with ethylacetate, the ethylacetate was washed with water, dried over magnesium sulphate and evaporated to a yellow solid (145 mg, 56%).

On the Symphony bis-1,4-aminomethylcyclohexane-2-chlorotrityl resin (0.1 mmol) (See method 1) was treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution) for 2 hours. Deprotection and washing as above.

HOBt (0.5 mmol, 68 mg) dissolved in DMF (4 ml) was stirred at 0° C. with DIPCI (0.5 mmol, 80 µl) for 10 min. 2-amino-5-cyanobenzoic acid (0.5 mmol, 84 mg.) was added and stirring continued for 10 min. at room temperature. The mixture was transferred to the reaction vessel on the Symphony and agitated for 10 hours with nitrogen. The resin was then washed with DMF (6×5 ml), DCM (6×5 ml) and air dried. The product was cleaved from the resin with 10% triethylsilane in TFA (10 ml) for 30 minutes, the resin filtered off, the TFA solution evaporated to dryness and triturated with diethyl ether to give the crude product. The crude product was then dissolved in saturated hydrogen chloride in ethanol (10 ml), sealed and allowed to stand overnight. The solution was then evaporated to dryness and treated with saturated ammonia in ethanol (10 ml) and allowed to stand overnight. The solution was then evaporated to dryness, dissolved in water and purified by reverse phase Hplc.

$^1$H nmr (D$_2$O) Mixture of cyclohexyl cis and trans isomers is 7.80 (1H, s); 7.50 (1H, d, J=7.5 Hz); 7.35 (5H, m); 6.75 (1H, d, J=7.5 Hz); .5.35 (1H, s); 2.87 (2H, m); 2.60 (2H, m); 1.00-1.60 (7H, m); 0.70 (3H, m) MS TOF 437 (M+1$^+$) Hplc (Jupiter5 C18, Gradient 2, water/acetonitrile/TFA) rt 13.11 min. (major), 13.31 (minor).

Prepared by Method 2

EXAMPLE 90

3-Amidino-benzoyl-D-phenylglycinyl-D-2-naphthylalanine $^1$H nmr (CD$_3$CN) 8.00 (1H, s); 7.95 (1H, d); 7.87 (1H, d) 7.72 (4H, m); 7.63 (2H, m); 7.38 (3H, m); 7.25 (4H, m); 5.60 (1H, s); 4.70 (1H, m); 3.25 (2H, m). MS TOF 495 (M+1$^+$). Hplc (Magellan C8, Gradient 3, water/acetonitrile/TFA) rt 10.19 min.

EXAMPLE 91

3-Amidino-benzoyl-D-phenylglycine-1,2,3,4, tetrahydoisoquinolin-2-yl-3-carboxylic acid $^1$H nmr (DMSO) mixture of isomers and rotamers (only one isomer cited in nmr) 8.28 (1H, s); 8.18 (1H, d); 7.90 (1H, d); 7.69 (1H, t); 7.35 (4H, m); 7.15 (5H, m); 6.30 (1H, s); 5.15, (1H,m); 5.70, (2H,m); 3.15, (2H,d). MS TOF 457 (M+1$^+$). Hplc (Jupiter5 C18, Gradient 1, water/acetonitrile/TFA) rt 13.84 and 14.33 min.

EXAMPLE 92

3-Amidino-benzoyl-D-phenylglycinyl-D-2-naphthylalaninyl-D-proline $^1$H nmr (CD$_3$CN) d 8.15 (1H, s); 8.08 (1H, d); 7.95 (1H, d); 7.82 (5H, m); 7.62, (1H, m); 7.22-7.5 (7H, m); 5.68 (1H, s); 5.01 (1H, m); 4.25(1H, m); 3.50, (1H,m); 3.1, (2H,m); 2.22, (1H,m); 2.0, (3H,m); . MS TOF 592 (M+1$^+$). Hplc (Jupiter5 C18, Gradient 1, water/acetonitrile/TFA) rt 16.04 min.

EXAMPLE 93

3-Amidino-benzoyl-D-phenylglycine-D-2-naphthylalaninyl-L-pipecolic acid $^1$H nmr (CD$_3$CN) 7.95 (1H, s); 7.90 (1H, d); 7.85 (1H, d); 7.62(5H, m); 7.25 (8H, m); 5.60 (1H, s); 5.15 (1H, t); 4.90 (1H, m); 3.60, (1H, m); 3.00 (4H, m); 2.05 (1H, m); 1.45, (2H,m); 1.15, (1H,m); 0.08, (1H,m). MS TOF 606 (M+1$^+$). Hplc (Magellan C8, Gradient 3, water/acetonitrile/TFA) rt 14.90 min.

EXAMPLE 94

3-Amidino-benzoyl-D-phenylglycine-D-2-naphthylalaninyl-D-pipecolic acid $^1$H nmr (CD$_3$CN) 7.95 (1H, s); 7.90 (1H, d); 7.85 (1H, d); 7.62(5H, m); 7.25 (8H, m); 5.45 (1H, s); 5.10 (1H, t); 5.00 (1H, m); obscured by solvent 3.60, (1H,m); 3.00 (4H, m); 2.05 (1H, m); 1.45, (2H,m); 1.25, (1H, m); 1.10, (1H,m). MS TOF 606 (M+1$^+$). Hplc (Magellan C8, Gradient 3, water/acetonitrile/TFA) rt 14.71 min.

EXAMPLE 95

3-Amidino-benzoyl-D-naphthylglycinyl-D-2-naphthylalaninyl-D-prolin $^1$H nmr (CD$_3$CN) d 8.13 (1H, s); 8.0 (2H, m); 7.85 (8H, m) 7.62, (1H,t); 7.45 (4H, m); 7.05 (2H,m); 6.35 (1H, s) 5.10 (1H, m); 4.34(1H, m); 3.67, (2H, m); 3.20, (2H,m); 2.22, (1H,m); 2.0 (obscured by solvent), (3H,m). MS TOF 642 (M+1⁺). Hplc (Jupiter5 C18, Gradient 1, water/acetonitrile/TFA) rt 18.14 min.

Prepared by Method 3

EXAMPLE 96

3-Amidino-benzoyl-D-naphthylglycinyl-D-2-naphthylalanine amide

¹H nmr (CD₃CN) d 8.25 (1H, d); 8.13 (1H, S); 7.95 (H, m) 7.85 (H, m); 7.74, (H,m); 7.65 (1H,t); 7.50 (H,m); 7.39 (2H,d); 6.83 (H,m); 6.22 (1H, s); 4.85 (1H, m) 3.25, (2H,m). MS TOF 545 (M+1⁺). Hplc (Jupiter5 C18, Gradient 1, water/acetonitrile/TFA) rt 17.32 min.

Prepared by Method 4

EXAMPLE 97

3-Amidino-benzoyl-D-phenylglycine-2-(4-methoxyphenyl)ethylamide

¹H nmr (D4 methanol) 8.20 (2H, m); 8.00 (1H, d); 7.73 (1H, t); 7.40(5H, m); 6.85 (4H, m); 5.60 (1H, m) 3.75 (2H, m); 2.70 (2H, m); 1.85 (3H, s). MS TOF 431 (M+1⁺). Hplc (Jupiter5 C18, Gradient 3, water/acetonitrile/TFA) rt 10.09 min.

EXAMPLE 98

3-Amidino-benzoyl-D-phenylglycine-2-(4-chlorophenyl)ethylamide

¹H nmr (D4 methanol) 8.28 (1H, s); 8.21, (1H,d); 7.97 (1H, d); 7.73(1H, t); 7.40(5H, m); 7.10 (4H, m); 5.61 (1H, m); 4.45 (2H, m); 2.78 (2H, m). MS TOF 436 (M+1⁺). Hplc (Jupiter5 C18, Gradient 3, water/acetonitrile/TFA) rt 11.26 min.

EXAMPLE 99

3-Amidino-benzoyl-D-phenylglycine-4-chloro benzylamide

¹H nmr (D4 methanol) 8.20 (1H, s); 8.11, (1H,d); 7.90 (1H, d); 7.65(1H, t); 7.50(5H, m); 7.17 (4H, m); 5.60 (1H, m); 4.31 (2H, m). MS TOF 422 (M+1⁺). Hplc (Jupiter5 C18, Gradient 3, water/acetonitrile/TFA) rt 10.81 min.

EXAMPLE 100

3-Amidino-benzoyl-D-phenylglycine-4-methoxy benzylamide

¹H nmr (D4 methanol) 8.22 (1H, s); 8.15, (1H,d); 7.93 (1H, d); 7.68 (1H, t); 7.40(5H, m); 6.95 (4H, m); 5.63 (1H, m); 4.30 (2H, m); 3.75, (3H,s). MS TOF 417 (M+1⁺) Hplc (Jupiter5 C18, Gradient 3, water/acetonitrile/TFA) rt 9.73 min.

EXAMPLE 101

3-Amidino-benzoyl-D-phenylglycine-3-chloro benzylamide

¹H nmr (D4 methanol) 8.32 (1H, s); 8.25 (1H, d); 7.95 (1H, d); 7.75(1H, t); 7.50(5H, m); 7.20 (4H, m); 5.72 (1H, m); 4.40 (2H, m). MS TOF 422 (M+1⁺). Hplc (Jupiter5 C18, Gradient 3, water/acetonitrile/TFA) rt 10.78 min.

EXAMPLE 102

3-Amidino-benzoyl-D-phenylglycine-4,4'-dimethyl dibenzylamide

¹H nmr (DMSO) 8.30 (1H, s); 8.21, (1H,d); 7.95 (1H, d); 7.70(1H, t); 7.45(5H, m); 7.10 (10H, m); 6.15 (1H, m); 4.41 (4H, m); 2.30, (6H, d). MS TOF 505 (M+1⁺). Hplc (Jupiter5 C18, Gradient 3, water/acetonitrile/TFA) rt 14.39 min.

EXAMPLE 103

3-Amidino-benzoyl-D-phenylglycine-N-methyl-2-phenethylamide

¹H nmr (DMSO) 8.25 (1H, s); 8.20, (1H,d); 7.95 (1H, d) 7.70(1H, t); 7.30 (10H, m); 6.02 (1H, m); 3.78 (1H, m) 3.54 (1H, m); 3.35, (1H, m); 2.85, (3H, d); 2.72, (1H,m). MS TOF 415 (M+1⁺). Hplc (Jupiter5 C18, Gradient 3, water/acetonitrile/TFA) rt 11.65 min.

EXAMPLE 104

3-Amidino-benzoyl-D-phenylglycine-N-methyl-1-naphthylmethylamide

¹H nmr (DMSO) 8.35 (1H, s); 8.30 (1H, d); 8.10 (1H, d) 7.85(5H, m); 7.60, (4H,m); 7.45 (4H, m); 6.20 (1H, s) 5.15 (2H, m); 2.91 (3H, s). MS TOF 451 (M+1⁺). Hplc (Jupiter5 C18, Gradient 3, water/acetonitrile/TFA) rt 12.53 min.

EXAMPLE 105

3-Amidino-benzoyl-D-phenylglycine-S-1-naphthylethylamide

¹H nmr (DMSO) 8.25 (1H, s); 8.19 (1H, d); 8.15, (2H,m); 7.95, (2H,m); 7.85 (1H, d); 7.70(1H, t); 7.55(5H, m); 7.45 (3H, m); 5.75 (1H, s); 5.70 (1H, m); 1.45 (3H, d). MS TOF 451 (M+1⁺). Hplc (Jupiter5 C18, Gradient 3, water/acetonitrile/TFA) rt 12.21 min.

EXAMPLE 106

3-Amidino-benzoyl-D-phenylglycine-1-S-cyclohexylethylamide

¹H nmr (DMSO) 8.32 (1H, s); 8.20 (1H, d); 7.95 (1H, d); 7.70(1H, t); 7.50 (2H, m); 7.30, (3H,m); 5.72 (1H, s) 3.55 (1H, m); 0.95-1.80 (11H, m); 0.9 (3H, d). MS TOF 407 (M+1⁺). Hplc (Jupiter5 C18, Gradient 3, water/acetonitrile/TFA) rt 12.11 min.

EXAMPLE 107

3-Amidino-benzoyl-D-phenylglycine-+/−(2-methyl)cyclohexylamide $^1$H nmr (DMSO) mixture of isomers (major isomer) 8.29 (1H, s); 8.18 (1H, d); 7.90 (1H, d); 7.70 (1H, t); 7.50 (2H, m); 7.30 (3H,m); 5.70 (1H, s); 0.9-1.8 (8H, m); 0.55 (3H, d). MS TOF 3.93 (M+1$^+$). Hplc (Jupiter5 C18, Gradient 3, water/acetonitrile/TFA) rt 11.45 min.

EXAMPLE 108

3-Amidino-benzoyl-D-phenylglycine-exo-2-norbornanamide $^1$H nmr (CD$_3$CN) 8.25 (1H, s); 8.17 (1H, d); 7.90 (1H, d) 7.68(1H, t); 7.50 (2H, m); 7.30, (3H,m); 5.55 (1H, s) 3.62 (1H, m); 1.05-1.80 (10H, m). MS TOF 391 (M+1$^+$). Hplc (Jupiter5 C18, Gradient 3, water/acetonitrile/TFA) rt 11.18 min.

EXAMPLE 109

3-Amidino-benzoyl-D-phenylglycine-4-chlorobenzhydrylamide $^1$H nmr (DMSO) 8.35 (1H, s); 8.29(1H, d); 8.03 (1H, d); 7.79(1H, t); 7.62 (2H, d); 7.41(10H, s); 7.18 (2H, d) 6.23, (1H,s); 6.00, (1H,s). MS TOF 498 (M+1$^+$). Hplc (Jupiter5 C18, Gradient 3, water/acetonitrile/TFA) rt 13.50 min.

EXAMPLE 110

3-Amidino-benzoyl-D-phenylglycine-1,1-diphenylmethylamide $^1$H nmr (DMSO) 8.23 (1H, s); 8.17(1H, d); 7.95 (1H, d); 7.70(1H, t); 7.52 (2H, m); 7.35(11H, s); 7.05 (2H, m); 6.10, (1H,s); 5.75, (1H,s). MS TOF 464 (M+1$^+$). Hplc (Jupiter5 C18, Gradient 3, water/acetonitrile/TFA) rt 12.04 min.

EXAMPLE 111

3-Amidino-benzoyl-D-phenylglycine-4-ethylbenzylamide $^1$H nmr (DMSO) 8.35 (1H, s); 8.25 (1H, d); 7.95 (1H, d); 7.70(1H, t); 7.62 (2H, d); 7.41(5H, m); 7.21, (1H,t); 6.90, (1H,d); 5.90, (1H,s); 2.60, (2H,q); 1.20, (3H,t). MS TOF 401 (M+1$^+$). Hplc (Jupiter5 C18, Gradient 3, water/acetonitrile/TFA) rt 12.03 min.

EXAMPLE 112

3-Amidino-benzoyl-D-phenylglycine-2-tertiary butyl anilide $^1$H nmr (DMSO) 8.21 (1H, s); 8.12 (1H, d); 7.85 (1H, d); 7.60(1H, t); 7.52 (2H, d); 7.25(4H, m); 7.10, (2H,m); 6.90, (1H,m); 5.90, (1H,s); 1.00, (9H,s). MS TOF 429 (M+1$^+$). Hplc (Jupiter5 C18, Gradient 3, water/acetonitrile/TFA) rt 12.05 min.

EXAMPLE 113

3-Amidino-benzoyl-D-phenylglycine-3-(1-hydroxyethyl) anilide $^1$H nmr (DMSO) 8.45 (1H, s); 8.35 (1H, d); 8.08 (1H, d); 7.88 (1H, t); 7.75 (3H, m); 7.55(4H, m); 7.38, (1H,t) 7.20, (1H,d); 6.02, (1H,s); 4.80, (1H,m); 1.45, (3H, d). MS TOF 417 (M+1$^+$). Hplc (Jupiter5 C18, Gradient 3, water/acetonitrile/TFA) rt 9.12 min.

EXAMPLE 114

3-Amidino-benzoyl-D-phenylglycine-4-(4'-acetylphenyl)piperazinamide $^1$H nmr (CD$_3$CN) 8.12 (1H, s); 8.05 (1H, d); 7.87 (1H, d); 7.80, (2H,d); 7.65(1H, t); 7.41 (5H, m); 6.80, (2H,d); 6.05 (1H, s); 3.80 (1H,m); 3.65 (2H,m); 3.45 (2H,m); 3.35 (1H,m); 3.20 (1H,m); 2.75 (1H,m); 2.45 (3H,s). MS TOF 485 (M+1$^+$) Hplc (Jupiter5 C18, Gradient 1, water/acetonitrile/TFA) rt 12.96 min.

EXAMPLE 115

3-Amidino-benzoyl-D-phenylglycine-4-(4'-methoxyphenyl)piperazinamide $^1$H nmr (CD$_3$CN) 8.15 (1H, s); 8.08 (1H, d); 7.91 (1H, d); 7.68, (2H,d); 7.45 (1H, t); 7.41 (5H, m); 6.99 (2H,d); 6.12 (1H, s); 3.95 (3H,m); 3.78 (3H,s); 3.75 (2H,m); 3.55 (2H,m); 3.45 (1H,m); 2.92 (1H,m). MS TOF 473 (M+1$^+$) Hplc (Jupiter5 C18, Gradient 1, water/acetonitrile/TFA) rt 10.34 min.

EXAMPLE 116

3-Amidino-benzoyl-D-phenylglycine-4-(4'-chlorophenyl)piperazinamide $^1$H nmr (CD$_3$CN) 8.05 (1H, s); 8.00 (1H, d); 7.87 (1H, d) 7.55(1H, t); 7.31 (5H, m); 7.08, (2H,d); 6.75, (2H,d) 5.95 (1H, s); 3.70 (1H,m); 3.55 (2H,m); 3.45 (1H,m); 3.12 (1H,m); 3.00 (1H,m); 2.85 (1H,m); 2.35 (1H,m). MS TOF 477 (M+1$^+$). Hplc (Jupiter5 C18, Gradient 1, water/acetonitrile/TFA) rt 17.80 min.

EXAMPLE 117

3-Amidino-benzoyl-D-phenylglycine-4-phenylpiperazinamide $^1$H nmr (DMSO) 8.28 (1H, s); 8.21 (1H, d); 7.94 (1H, d); 7.71 (1H, t); 7.52, (2H,d); 7.35 (3H, m); 7.21 (2H,m) 6.89, (2H,d); 6.80 (1H,t); 6.15 (1H, s); 3.75 (3H, m); 3.55 (1H,m); 3.15 (2H,m); 3.00 (1H, m); 2.78 (1H,m). MS TOF 442 (M+1$^+$). Hplc (Jupiter5 C18, Gradient 3, water/acetonitrile/TFA) rt 9.99 min.

EXAMPLE 118

3-Amidino-benzoyl-D-phenylglycine-4-toluenesulphonyl piperazinamide $^1$H nmr (DMSO) 8.21 (1H, s); 8.11 (1H, d); 7.91 (1H, d) 7.69 (1H, t); 7.5.0, (4H, m); 7.35 (2H, m); 7.31 (3H, m) 6.05 (1H, s); 3.60 (3H, m); 3.45 (2H, m); 2.90 (1H, m) 2.78 (1H,m); 2.70 (1H, m); 2.45 (3H, s); 2.25 (1H,m). MS TOF 521 (M+1$^+$). Hplc (Jupiter5 C18, Gradient 3, water/acetonitrile/TFA) rt 10.76 min.

EXAMPLE 119

3-Amidino-benzoyl-D-phenylglycine-4-benzoyl piperazinamide $^1$H nmr (CD$_3$CN) 7.95 (1H, s); 7.88 (1H, d); 7.70 (1H, d); 7.45 (1H, t); 7.20, (10H, m); 5.85 (1H, s, broad); 2.50-3.60 (8H, m, broad signals). MS TOF 470 (M+1$^+$). Hplc (Jupiter5 C18, Gradient 1, water/acetonitrile/TFA) rt 10.78 min.

EXAMPLE 120

3-Amidino-benzoyl-D-phenylglycine piperidinamide $^1$H nmr (DMSO) 8.20 (1H, s); 8.10 (1H, d); 7.86 (1H, d) 7.65(1H, t); 7.45 (5H, m); 6.02 (1H, s); 3.70 (1H, m) 3.40 (3H, m); 1.53 (3H, m); 1.41 (2H, m); 0.93 (1H, m) MS TOF 365 (M+1$^+$). Hplc (Jupiter5 C18, Gradient 3, water/acetonitrile/TFA) rt 9.29 min.

EXAMPLE 121

3-Amidino-benzoyl-D-phenylglycine-(1S, 2S, 3S, 5R)-isopinocamphyl amide $^1$H nmr (DMSO) 8.30 (1H, s); 8.21 (1H, d); 7.98 (1H, d); 7.71 (1H, t); 7.51 (2H, m); 7.35 (3H, m); 5.74 (1H, s); 4.05 (1H, m); 2.35 (2H, m); 1.90 (1H, m); 1.72 (2H, m); 1.60 (1H,m); 1.21 (3H,s); 1.01 (1H,d); 0.97 (3H,s); 0.83 (3H,d). MS TOF 433 (M+1$^+$). Hplc (Jupiter5 C18, Gradient 3, water/acetonitrile/TFA) rt 13.32 min.

EXAMPLE 122

3-Amidino-benzoyl-D-phenylglycine-3-phenylanilide $^1$H nmr (DMSO) 8.31 (1H, s); 8.24 (1H, d); 7.95 (2H, m) 7.53(1H, t); 7.60 (5H, m); 7.4 (8H, m); 5.85 (1H, s) MS TOF 449 (M+1$^+$). Hplc (Jupiter5 C18, Gradient 3, water/acetonitrile/TFA) rt 12.42 min.

EXAMPLE 123

3-Amidino-benzoyl-D-phenylglycine-3-(O-benzoyl hydroxymethyl)anilide $^1$H nmr (DMSO) 8.40 (1H, d); 8.33 (1H, s); 8.31 (1H, d); 7.97 (2H, d); 7.75(1H, t); 7.64 (1H,m); 7.56 (2H,d); 7.40 (8H, m); 7.21 (1H,t); 5.75 (1H, s); 5.20 (2H,s). MS TOF 507 (M+1$^+$). Hplc (Jupiter5 C18, Gradient 3, water/acetonitrile/TFA) rt 13.53 min.

EXAMPLE 124

3-Amidino-benzoyl-D-phenylglycine-4-(4-chlorobenzoyl) piperidinamide $^1$H nmr (DMSO) Mixture of rotomers 8.08 (2H, m); 7.80 (3H, m); 7.55(1H, t); 7.45 (2H, m); 7.25 (5H,m); 5.92 (1H, s); 4.25 (1H,m); 3.80 (1H, m); 3.55 (1H, m); 2.90 (1H,m); 2.68 (1H,m); 1.60 (1H,m); 1.55 (1H,m); 1.30 (1H, m); 0.83 (1H,m). MS TOF 504 (M+1$^+$). Hplc (Jupiter5 C18, Gradient 3, water/acetonitrile/TFA) rt 12.21 min.

EXAMPLE 125

3-Amidino-benzoyl-D-phenylglycine-4-(4-fluorobenzoyl) piperidinamide $^1$H nmr (DMSO) Mixture of rotomers 8.40 (2H, m); 8.22 (2H, m); 8.10 (1H,d); 7.88(1H, t); 7.64 (2H, m); 7.54 (5H,m); 6.30 (1H, s); 4.65 (1H,m); 4.20 (1H, m); 3.82 (1H, m) 3.10 (2H,m); 1.98 (1H,m); 1.70 (1H, m); 1.40 (1H,m); 0.83 (1H,m). MS TOF 487 (M+1$^+$). Hplc (Jupiter5 C18, Gradient 3, water/acetonitrile/TFA) rt 11.37 min.

EXAMPLE 126

3-Amidino-benzoyl-D-phenylglycine-4-benzyl piperidinamide $^1$H nmr (DMSO) Mixture of rotomers 7.98 (2H, m); 7.68 (1H, m); 7.45(1H, m); 6.60-7.25 (10H, m); 5.86 (1H, s); 4.15 (1H,m); 3.68 (1H, m); 2.63 (1H, m); 2.45 (1H,m); 2.21 (3H,m); 1.50 (1H, m); 1.33 (1H,m); 1.03 (1H, m); 0.45 (1H, m). MS TOF 455 (M+1$^+$). Hplc (Jupiter5 C18, Gradient 3, water/acetonitrile/TFA) rt 13.18 min.

EXAMPLE 127

3-Amidino-benzoyl-D-phenylglycinyl-D-2-naphthylalanine pyrrolidinamide $^1$H nmr (DMSO) 8.19 (1H, s); 8.11 (1H, d); 7.92 (1H, d) 7.75(5H, m); 7.41 (5H, m); 7.30 (3H,m); 5.81 (1H, s); 4.80 (1H, m); 3.20 (4H, m); 3.00 (2H, m); 1.55 (4H, m). MS TOF 548 (M+1$^+$). Hplc (Jupiter5 C18, Gradient 3, water/acetonitrile/TFA) rt 11.13 min.

EXAMPLE 128

3-Amidino-benzoyl-DL-1-naphthylglycinyl-D-2-S naphthylalanine pyrrolidinamide $^1$H nmr (DMSO) mixture of isomers 8.25 (1H, s); 8.20 (1H, d); 8.15 (2H, m); 8.05 (1H, d); 6.90-8.00 complex multiplet (13H,m); 6.50 (1H, m); 4.90 (1H, m); 2.90-3.50 broad, partially covered by solvent (H, m); 1.70 (4H, m). MS TOF 598 (M+1$^+$). Hplc (Jupiter5 C18, Gradient 3, water/acetonitrile/TFA) rt 12.18 and 12.37 min.

EXAMPLE 129

3-Amidino-benzoyl-DL-1-naphthylglycine-4-methylbenzylamine $^1$H nmr (DMSO) mixture of isomers 8.25 (1H, s); 8.20 (1H, d); 8.10 (1H,m); 7.90 (3H,m); 7.70 (1H, t); 7.55 (4H, m); 7.06 (4H,m); 6.45 (1H, s); 4.30 (2H, m); 2.25 (3H, s). MS TOF 451 (M+1$^+$). Hplc (Jupiter5 C18, Gradient 3, water/acetonitrile/TFA) rt 12.30 min.

EXAMPLE 130

3-Amidino-benzoyl-DL-1-naphthylglycine-4-benzoyl piperidinamide $^1$H nmr (DMSO) mixture of isomers 8.15 (2H, m); 8.00 (1H, d); 7.85 (5H,m); 7.45 (8H,m); 6.70 (1H, s); 4.50 (1H, m); 3.15 (1H,m); 2.80 (3H,m); 1.60 (2H, m); 1.42 (1H, m); 0.45 (1H, m). MS TOF 519 (M+1$^+$). Hplc (Jupiter5 C18, Gradient 3, water/acetonitrile/TFA) rt 12.67 min.

EXAMPLE 131

3-Amidino-benzoyl-DL-1-naphthylglycine-3-(1-hydroxyethyl)anilide $^1$H nmr ( ) mixture of isomers 8.10 (1H, s); 8.00 (1H, d); 7.80 (3H,m); 7.50 (7H,m); 7.30 (1H, m); 7.20 (1H,m); 7.00 (1H,m); 6.45 (1H, s); 4.65 (1H, m); 1.20 (3H,s). MS TOF 467 (M+1$^+$). Hplc (Jupiter5 C18, Gradient 3, water/acetonitrile/TFA) rt 10.67 min.

EXAMPLE 132

3-Amidino-benzoyl-D-phenylglycine morpholinamide $^1$H nmr (DMSO) 8.25 (1H, s); 8.18 (1H, d); 7.91 (1H, d) 7.68 (1H, t); 7.40 (5H, m); 6.09 (1H, s); 5.45 (4H, m) 3.63 (4H, m). MS TOF 367 (M+1$^+$). Hplc (Jupiter5 C18, Gradient 3, water/acetonitrile/TFA) rt 5.53 min.

EXAMPLE 133

3-Amidino-benzoyl-R,S-3-amino-3-phenylpropionic-1-adamantylamide $^1$H nmr (CD$_3$CN) 8.03 (1H, s); 7.97 (1H, d); 7.75 (1H, d); 7.55 (1H, t); 7.20 (5H, m); 5.25 (1H, t); 2.50-1.70 (15H, m). MS TOF 446 (M+1$^+$). Hplc (Jupiter5 C18, Gradient 3, water/acetonitrile/TFA) rt 11.56 min.

EXAMPLE 134

3-Amidino-benzoyl-DL-1-naphthylglycine-(Z,E)-(2-methyl)cyclohexylamide

Mixture of isomers. MS TOF 443 (M+1$^+$). Hplc (Jupiter5 C18, Gradient 3, water/acetonitrile/TFA) rt 12.57 and 12.75 min.

Prepared by Method 5

EXAMPLE 135

3-Amidino-benzoyl-D-phenylglycine cyclopropylmethylamid

MS TOF 351 (M+1$^+$). Hplc (Jupiter5 C18, Gradient 3, water/acetonitrile/TFA) rt 8.57 min.

EXAMPLE 136

3-Amidino-benzoyl-D-phenylglycine-2-indanylamide

MS TOF 413 (M+1$^+$). Hplc (Jupiter5 C18, Gradient 3, water/acetonitrile/TFA) rt 11.13 min.

EXAMPLE 137

3-Amidino-benzoyl-D-phenylglycine-3-methylbutylamid

MS TOF 367 (M+1$^+$) Hplc (Jupiter5 C18, Gradient 3, water/acetonitrile/TFA) rt 10.81 min.

EXAMPLE 138

3-Amidino-benzoyl-D-phenylglycine-4-fluorobenzylamide

MS TOF 405 (M+1$^+$). Hplc (Jupiter5 C18, Gradient 3, water/acetonitrile/TFA) rt 10.41 min.

EXAMPLE 139

3-Amidino-benzoyl-D-phenylglycine trans-2-phenylcyclopropylamide

MS TOF 413 (M+1$^+$). Hplc (Jupiter5 C18, Gradient 3, water/acetonitrile/TFA) rt 11.25 min.

Prepared by Method 6

EXAMPLE 140

3-Amidino-benzoyl-D-phenylglycine-2-(4-N-acetyl piperidinyl)ethyl ester $^1$H nmr (DMSO) 8.13 (1H, s); 8.07 (1H, d); 7.92 (1H, d) 7.69 (2H,d); 7.45 (5H, m); 5.63 (1H, s); 4.25 (2H,m); 3.65 (1H,m); 3.45 (3H,m); 2.80 (1H,m); 3.35 (1H,m); 2.00 (3H, s); 1.50 (3H,m); 1.30 (1H,m); 0.95 (1H,m). MS TOF 451 (M+1$^+$). Hplc (Jupiter5 C18, Gradient 2, water/acetonitrile/TFA) rt 19.00 min.

Method 7

By solution phase strategy: Typically a Boc-amino alcohol with TEA is treated with an acid chloride to give an ester. Removal of the Boc protecting group with TFA followed by further extension of the compounds as in Method 4.

EXAMPLE 141

{R}-{[N-(3-amidino)benzoyl]amino}-2-phenylethyl-4-(methoxy)benzoate

To Boc-(D)-phenylglycinol (237 mg, 1 mmol, 1 eq) and TEA (153 µl, 1.1 mmol, 1 eq) dry DCM (5 ml) was added p-anisoyl chloride (188 mg, 1.1 mmol, 1.1 eq). The reaction was stirred overnight. Ethylacetate (30 ml) was added and the organic layer was washed successively with 2×10 ml of 10% HCl, NaHCO$_3$ solution, finally brine. Dried over magnesium sulphate, filtered and evaporated to give the crude product (410 mg). After treatment with TFA to remove the Boc group the compound were extended as in Method 4.

$^1$H nmr (DMSO) 8.25 (1H, s); 8.21 (1H, d); 7.95 (1H, d); 7.85 (2H,d); 7.75 (1H, t); 7.45 (5H, m); 7.05 (2H, d); 5.55 (1H, q); 4.55 (2H, d); 3.85 (3H, s). MS TOF 418 (M+1$^+$). Hplc (Jupiter5 C18, Gradient 3, water/acetonitrile/TFA) rt 11.01 min.

By Analogous Methods the Following Were Prepared

EXAMPLE 142

R-2-{[N-(3-amidino)benzoyl]amino}-2-phenylethyl-4-(methyl)benzoate $^1$H nmr (DMSO) 8.25 (1H, s); 8.21 (1H, d); 7.95 (1H, d) 7.80 (2H, d); 7.75 (1H, t); 7.50 (2H, d); 7.34 (5H, m); 5.55 (1H, q); 4.55 (2H, d); 3.35 (3H, s). MS TOF 402 (M+1$^+$). Hplc (Jupiter5 C18, Gradient 3, water/acetonitrile/TFA) rt 11.87 min.

EXAMPLE 143

R-2-{[N-(3-amidino)benzoyl]amino}-2-phenylethyl-4-(trifluoromethoxy)benzoate $^1$H nmr (DMSO) 8.45 (1H, s); 8.40 (1H, d); 8.25 (2H, d) 8.15 (1H, d); 7.95 (1H, t); 7.65 (7H, m); 5.78 (1H, q) 4.84 (2H, d). MS TOF 472 (M+1$^+$). Hplc (Jupiter5 C18, Gradient 3, water/acetonitrile/TFA) rt 12.85 min.

Method 8

By solution phase strategy: Typically a Boc-amino alcohol and a carboxylic acid are treated with (4-dimethylamino) phenyldiphenyl phosphine and diethylazodicarboxylate to give an ester. Removal of the Boc protecting group with TFA followed by further extension of the compounds as in Method 4.

EXAMPLE 144

{R}-{[N-(3-amidino)benzoyl]amino}-2-phenylethyl-4-(acetimido)benzoate

A dry solution of diethylazodicarboxylate (158 μl, 1 mmol, 1 eq) in THF (5 ml), was added dropwise to an anhydrous solution of (4-dimethylamino)phenyldiphenyl phosphine (306 mg, 1 eq, 1 mmol), Boc-(D)-phenylglycinol (356 mg, 1,5 eq, 1 mmol) and 4-acetimidobenzoic acid (179 mg, 1 mmol, 1 eq) in THF (5 ml) at −78° C. The reaction allowed to warm to room temperature and stirred overnight. Reaction monitored by t. l. c, SiO$_2$/75% ethylacetate in hexane indicating formation of product. R$_f$=0.5. The solution was evaporated to remove THF and taken up into ethyl acetate (30 ml) washed with 10% HCl solution, then brine. The solution was dried, filtered and evaporated to dryness. Crude yield ~650 mg. Purifcation by column chromatography gave a yield of product of 200 mg, (50%). After treatment with TFA to remove the Boc group the compound were extended as in Method 4.

$^1$H nmr (DMSO) 8.48 (1H, s); 8.54 (1H, d); 8.15 (1H, d) 8.05 (2H, d); 7.95 (3H, m); 7.75 (2H, m); 7.55 (3H, m) 5.70 (1H, m); 4.70 (2H, m); 2.27 (3H, s). MS TOF 445 (M+1$^+$). Hplc (Jupiter5 C18, Gradient 3, water/acetonitrile/TFA) rt 9.38 min.

EXAMPLE 145

R-2-{[N-(3-amidino)benzoyl]amino}-2-phenylethyl-4-(methylsulphonyl)benzoate $^1$H nmr (DMSO) 8.25 (1H, s); 8.21 (1H, d); 8.10 (4H, q); 7.95 (1H, d); 7.75 (1H, t); 7.45 (5H, m); 5.60 (1H, q) 4.65 (2H, d); 2.08 (3H, s). MS TOF 466 (M+1$^+$). Hplc (Jupiter5 C18, Gradient 3, water/acetonitrile/TFA) rt 9.75 min.

EXAMPLE 146

R-2-{[N-(3-amidino)benzoyl]amino}-2-phenylethyl-4-acetylbenzoate $^1$H nmr (DMSO) 8.03 (1H, s); 8.00 (1H, d); 7.83 (4H, m); 7.73 (1H, d); 7.53 (1H, t); 7.25 (5H, m); 5.38 (1H, q); 4.41 (2H, d); 2.42 (3H, s). MS TOF 430 (M+1$^+$). Hplc (Jupiter5 C18, Gradient 3, water/acetonitrile/TFA) rt 10.46 min.

Method 9

By solution phase strategy: Typically an activated Boc-amino acid was converted to the amide with ammonia and then to the thioamide using Lawessons reagent. Reaction of the thioamide with an acyl bromide to give a Boc protected thiazole. Deprotection of the thiazole with TFA allows further extension of the compound as in Method 4.

EXAMPLE 147

2-[(N-3-amidinobenzamido)-1-phenyl]methyl-4-phenylthiazole

To a solution of Boc-D-phenylglycine (8.75 mg 3.5 mmole) in a 1:1 mixture of DMF and DCM (40 ml) was added 1-hydroxybenzotriazole (520 mg 1.1 equiv.) and DIPCI (602 ml 1.1 equiv.) and the mixture stirred for 30 min at rt. Ammonia gas was bubbled in and the mixture left overnight before diluting with ethyl acetate and washing with 10% hydrochloric acid and sat. sodium bicarbonate. The organic solution was dried (magnesium sulphate) and evaporated. Flash chromatography (silica gel DCM/ethylacetate 0-50%) gave the amide 770 mg 86%. To a solution of Boc-D-phenylglycine amide (740 mg 2.96 mmole) in THF 25 ml was added Lawesson's reagent (1.2 g) and the mixture stirred overnight. The solvent was evaporated off under reduced pressure and the residue purified by flash chromatography (silica gel-hexane/ethyl acetate 10 to 30%) to give the thioamide 671 mg.

The thioamide (650 mg) was dissolved in acetone (20 ml) and phenacyl bromide (486 mg 1 equiv) stirred for 30 min and then diluted with chloroform/aqueous sod. bicarbonate (20 ml each), separated, dried (magnesium sulphate) and evaporated. The residue was dissolved in DCM (20 ml) and treated with pyridine (350 ml) and trifluoroacetic anhydride (360 ml). After 150 min the solvent was removed under reduced pressure and the residues redissolved in DCM and washed with sat. sod. bicarbonate. Purification by flash chromatography (silica gel-hexane/ethyl acetate 10 to 30%) gave the thiazole intermediate 687 mg.

Deprotection of the amine was carried out using 50% TFA in DCM (30 min), evaporation of solvent under reduced pressure, dissolving in DCM, washing with sat sod. bicarbonate, drying (magnesium sulphate) and evaporation.

Coupling of the thiazole intermediate to 3-amidino benzoic acid was carried out using the standard method Method 4 to give 2-[(N-3-amidinobenzamido)-1-phenyl]methyl-4-phenylthiazole TFA salt.

$^1$HNMR (d$_6$DMSO) 9.9 (1H, d); 9.48 (1H, s); 9.09 (1H, s); 8.40 (1H, s); 8.37 (1H, d); 8.16 (1H, s); 7.98 (3H, m); 7.80 (1H, d); 7.63 (2H, d); 7.5 (6H, m); 6.80 (1H, d). MS TOF 413 (M+1$^+$). Hplc (Jupiter5 C18, Gradient 3, water/acetonitrile/TFA) rt 11.8 min.

Method 10

By solution phase: Typically a compound prepared as Method 4 is further reacted with ethyl chloroformate to give the 3-Ethoxycarbonyl amidino compound

EXAMPLE 148

3-(Ethoxycarbonyl)-amidinobenzoyl-D-phenylglycine-4-methylbenzyl amide

To a solution of 3-Amidinobenzoyl-(D)-phenylglycine-4-methylbenzyl amide (125 mg, 0.31 mmole) in DCM (20 ml) was added DIPEA (163 ml 0.94 mmole) and then over 2 min. ethyl chloroformate 33 ml 0.34 mmole). The reaction was stirred overnight and the solvent removed under reduced pressure. The residue was dissolved in ethylacetate and washed with water (×3), dried (magnesium sulphate) and evaporated to dryness. Flash chromatography (silica gel, DCM/Ethylacetate 0-100%) gave the title compound 98 mg $^1$HNMR (d$_6$DMSO) 9.1 (2H, bs); 8.93 (1H,d); 8.82 (1H, t) 8.46 (1H, s); 8.08 (2H, t); 7.53 (3H, m); 7.36 (3H, m) 7.08 (4H, s); 5.76 (1H, d); 4.23 (2H,d); 4.07 (2H, q) 2.25 (3H, s); 1.22 (3H,t). MS TOF 473 (M+1$^+$). Hplc (Jupiter5 C18, Gradient 3, water/acetonitrile/TFA) rt 11.06 min.

By an Analogous Method

EXAMPLE 149

3-(Ethoxycarbonylamidino)-D-phenylglycine-4-(4-chlorophenyl)-piperazinamide $^1$HNMR (d$_6$DMSO) 9.01 (3H, bs+s); 8.40 (1H, s); 8.08 (2H, m); 7.52 (3H, m); 7.40 (3H, m); 7.25 (2H, d); 6.88 (2H, d); 6.15 (1H, d); 4.05 (2H, d); 3.70 (4H, m); 3.01 (4H, m); 1.20 (3H, t). MS TOF 549 (M+1$^+$). Hplc (Jupiter5 C18, Gradient 3, water/acetonitrile/TFA) rt 12.48 min.

Method 11

By solution phase srategy: Typically 3-cyanobenzoic acid is activated with carbonyl-diimidazole and reacted with R-phenylglycinol to give 3-cyanobenzoylphenylglycinol. Reaction with a trichloroacetimidate and BF$_3$ etherate, (4), gives an ether. Reaction of the cyano group with HCl in ethanol followed by ammonia in ethanol gives the amidino compound.

EXAMPLE 150

3-Amidinobenzoyl-2-(4-methylbenzyloxy)-1-phenylethylamide

3-Cyanobenzoic acid was condensed with (R)-phenylglycinol using N,N'-carbonyl-diimidazole as activator to give 3-cyanobenzoylphenylglycinol.

$^1$HNMR (CDCl$_3$) 8.05 (2H, d); 7.55 (1H, t); 7.4 (8H, m); 5.17 (2H, bs); 4.50 (2H, bs).

3-Cyanobenzoylphenylglycinol in 1:1 DCM: cyclohexanol (50 ml) was treated with 4-methylbenzyl trichloroacetimidate and BF$_3$ etherate and the crude product purified by flash chromatography to give 3-cyanobenzoyl-2-(4-methylbenzyloxy)-1-phenylethylamide which was then taken up in ethanol and saturated with HCl gas and left overnight at room temperature. The solvent and excess HCl gas were removed under reduced pressure and the residue redissolved in ethanol and the solution saturated with ammonia gas and left overnight. The solvent and excess ammonia were removed under reduced pressure and the residue treated with aqueous acetonitrile and trifluoroacetic acid. Preparative hplc gave the title compound approx 80% pure by hplc.

$^1$HNMR (d$_6$DMSO) 9.1 (5H, bs+d); 8.22 (2H, s+d); 7.90 (1H, d); 7.74 (1H, t); 7.35. (5H, m); 7.10 (4H, Abq); 5.35 (1H, q); 4.50 (2H, s); 3.70 (2H, m); 2.25 (3H, s). MS TOF 389 (M+1$^+$). Hplc (Jupiter5 C18, Gradient 3, water/acetonitrile/TFA) rt 11.79 min.

Miscellaneous Examples

EXAMPLE 151

N-(3-Amidinobenzoyl)-2-amino-2 (R)-phenylethoxycarbonyl-4-methylaniline

To a solution of Boc-(R)-phenylglycinol (500 mg 3.65 mmole) in DMF (20 ml) was added 4-methylphenylisocyanate (500 ml 4.0 mmole) and the mixture warmed to 50° C. before standing at room temperature overnight. Dilution with ethyl acetate and washing with sat. sodium bicarbonate gave after drying (magnesium sulphate) and evaporation of solvent the crude intermediate which was purified by flash chromatography (silica gel, EtOAC 0-20% in DCM)

Deprotection of the amine was carried out using 50% TFA in DCM (30 min), evaporation of solvent under reduced pressure, dissolving in DCM, washing with sat sod. bicarbonate, drying (magnesium sulphate) and evaporation.

Coupling of the thiazole intermediate to m-benzamidine was carried out using the standard method 4 to give N-(3-Amidinobenzoyl)-2-amino-2 (R)-phenylethoxycarbonyl-4-methylaniline.

$^1$HNMR (d$_6$DMSO) 8.2 (2H, m); 7.90 (1H, d); 7.72 (1H, t); 7.44 (2H, d); 7.35 (5H, m); 7.08 (2H, d); 5.3.5 (1H, m); 4.33 (2H, m); 2.25 (3H, s). MS TOF 417 (M+1$^+$). Hplc (Jupiter5 C18, Gradient 3, water/acetonitrile/TFA) rt 11.54 min.

EXAMPLE 152

3-Amidinobenzyl-D-phenylglycine-cis/trans-4-aminomethyl cyclohexylmethylamide

Bis-1,4-aminomethylcyclohexane 2-chlorotrityl resin (0.2 mmol) (as prepared by method 1) was treated with Fmoc-D-Phenylglycine (0.5 mmol, 187 mg), DMF (2.5 ml), TBTU in DMF (1.25 ml of a 450 mM solution) and DIPEA in DMF (1.25 ml of a 900 mM solution). The mixture was agitated with nitrogen for 2 hours. Deprotection and washing as in method 1. The resin was then treated with 3-cyanobenzaldehyde (0.5 mmol. 66 mg) in DMF agitated over night. The resin was washed with DMF then with Dry THF to remove all DMF. Sodium cyanoborohydride (1 mmol. 63 mg) in THP and acetic acid (100 µl) was then added to the resin and agitated for 4 hours. The resin was then washed with THF, the DMF and finally DCM. The resin was the treated with TFA containing 5% TES for 30 mins. The resin was then filtered off and the TFA evaporated then held under high vacuum to dry the product. The product was then taken up into saturated hydrogen chloride gas in ethanol (20 ml.) overnight. The ethanol was then evaporated and the product treated with saturated ammonia gas in ethanol (20 ml.) overnight. The ethanol was then evaporated and the product purified by preparative hplc.

$^1$H nmr (CD$_3$CN) Mixture of cyclohexyl cis and trans isomers 7.85 (2H, m); 7.79 (1H, d); 7.66 (1H, t); 7.50 (5H, m); 4.97 (1H, s); 4.22 (2H, s); 3.00 (2H, m); 2.78 (2H, m); 1.48 (7H, m); 0.86 (3H, m) MS TOF 407 (M+1$^+$). Hplc (Jupiter5 C18, Gradient 2, water/acetonitrile/TFA) rt 9.78 min.

EXAMPLE 153

4-methylphenylacetyl-L-phenylglycine-3-amidino anilide

Boc-L-phenylglycine (0.6 mmol, 150 mg), HATU (0.6 mmol, 230 mg) and DIPEA (1.2 mmol., 220 µl) were dissolved in DMF (5 ml) and stirred for 15 mins. 3-Aminobenzonitrile (0.6 mmol., 70 mg) was added and the mixture stirred overnight. The DMF was then evaporated and the mixture taken into ethylacetate (50 ml) and washed with water, sodium carbonate solution, water 10% hydrochloric acid and water. The ethylacetate was evaporated to give the product Boc-L-phenylglycine-3-cyano anilide. The product was treated with TFA (50 ml) for 30 mins. The TFA was evaporated to dryness. m-Tolylacetic acid (0.7 mmol., 100 mg), HATU (0.7 mmol., 250 mg) and DIPEA (1.4 mmol., 250 µl) were dissolved in DMF (5 ml) and stirred for 15 mins. This was then added to the above product with DIPEA (0.6 mmol., 110 µl) and stirred overnight. The DMF was evaporated and the mixture taken into ethylacetate (50 ml) and washed as above. The ethyl acetate was then evaporated and the product treated with hydrogen chloride gas in ethanol and ammonia gas in ethanol as above. The product was purified by preparative hplc.

$^1$HNMR (d$_4$ MeOH) 8.23 (1H,s); 7.90 (1H, d); 7.72 (7H, m); 7.44 (1H, t); 7.29 (3H, m); 5.75 (1H, m); 3.80 (2H, s); 2.50 (3H, s). MS TOF 401 (M+1$^+$). Hplc (Jupiter5 C18, Gradient 1, water/acetonitrile/TFA) rt 14.59 min.

Compounds Synthesised by Method 4

EXAMPLE 154

3-Amidino-benzoyl-D-phenylglycine-4-(4'-nitrophenyl) piperazinamide $^1$H nmr (CD$_3$CN) 8.20(1H, s); 8.05 (3H, m); 7.85 (1H, d) 7.70 (1H, t); 7.40 (5H, m); 6.82, (2H,d); 6.05 (1H, s) 3.75 (1H,m); 3.65(2H,m); 3.45(3H,m); 3.30 (1H,m); 2.85 (1H, m). MS TOF 486 (M+1$^+$). Hplc (Jupiter5 C18, Gradient 1, water/acetonitrile/TFA) rt 11.65 min.

EXAMPLE 155

3-Amidino-benzoyl-D-phenylglycine-4-(4'-aminophenyl) piperazinamide $^1$H nmr (CD$_3$CN) 8.00 (1H, s); 7.85 (1H, d); 7.65 (1H, d) 7.45(1H, t); 7.20 (5H, m); 6.95, (2H,d); 6.70, (2H,d) 5.85 (1H, s); 3.55 (1H,m); 3.30 (1H,m); 2.95 (3H,m); 2.80(1H, m); 2.40 (1H,m). MS TOF 458 (M+1$^+$). Hplc (Jupiter5 C18, Gradient 2, water/acetonitrile/TFA) rt 12.57 min.

EXAMPLE 156

3-Amidino-benzoyl-D-phenylglycine-4-(4'-fluorophenyl) piperazinamide $^1$H nmr (CD$_3$OD) 8.25 (1H, s); 8.20 (1H, d); 7.95 (1H, d) 7.75(1H, t); 7.45(5H, m); 7.10, (4H,m); 6.20 (1H, s); 3.90 (3H,m); 3.70 (1H, m); 3.35 (2H,m); 3.15 (1H,m); 2.65 (1H, m). MS TOF 460 (M+1$^+$). Hplc (Jupiter5 C18, Gradient 1, water/acetonitrile/TFA) rt 14.88 min.

EXAMPLE 157

3-Amidino-benzoyl-D-phenylglycine-4-(4'-pyridyl) piperazinamide $^1$H nmr (CD$_3$CN) 8.05(1H, s); 7.95 (1H, d); 7.90(2H,d) 7.80 (1H, d); 7.55(1H, t); 7.30 (5H, m); 6.80, (2H, d) 6.00 (1H, s); 3.70 (3H,m); 3.50 (3H,m); 3.40 (1H,m) 3.15 (1H, m). MS TOF 444 (M+1$^+$). Hplc (Jupiter5 C18, Gradient 2, water/acetonitrile/TFA) rt 11.54 min.

EXAMPLE 158

3-Amidino-benzoyl-D-phenylglycine-4-(2'-pyridyl) piperazinamide $^1$H nmr (CD$_3$OD) 8.30 (1H, s); 8.20 (1H, d); 8.10 (1H, m); 7.95, (2H,m); 7.75(1H, t); 7.50 (5H, m); 7.30, (2H,d) 7.15(1H, t); 6.20 (1H, s); 3.95 (3H,m); 3.75 (4H,m) 3.40 (1H,m). MS TOF 444 (M+1$^+$). Hplc (Jupiter5 C18, Gradient 2, water/acetonitrile/TFA) rt 11.67 min.

EXAMPLE 159

3-Amidino-benzoyl-D-phenylglycine-4-benzylpiperazinamide $^1$H nmr (CD$_3$CN) 8.15 (1H, s); 8.05 (1H, d); 7.90 (1H, d); 7.65(1H, t); 7.40 (10H, m); 6.05 (1H, s); 4.20 (2H,s); 3.20(8H, v. broad m). MS TOF 457 (M+1$^+$). Hplc (Jupiter5 C18, Gradient 1, water/acetonitrile/TFA) rt 9.52 min.

EXAMPLE 160

3-Amidino-benzoyl-D-phenylglycine-4-(3-chlorophenyl) piperazinamide $^1$H nmr (CD$_3$CN) 8.17 (1H, s); 8.07 (1H, d); 7.90 (1H, d); 7.65(1H, t); 7.42 (5H, m); 7.15 (1H, m); 6.80 (3H,m); 6.08 (1H, s); 3.85 (1H,m); 3.55 (3H, m); 3.25 (1H, m); 3.10 (1H,m); 2.95 (1H,m); 2.40 (1H,m). MS TOF 477 (M+1$^+$). Hplc (Jupiter5 C18, Gradient 1, water/acetonitrile/TFA) rt 15.39 min.

EXAMPLE 161

3-Amidino-benzoyl-D-phenylglycine-4-(2-chlorophenyl) piperazinamide $^1$H nmr (CD$_3$CN) 8.15 (1H, s); 8.07 (1H, d); 7.90 (1H, d) 7.65(1H, t); 7.42 (5H, m); 7.20 (1H, m); 6.95 (3H,m); 6.05 (1H, s); 3.80 (1H,m); 3.65 (2H,m); 3.45 (1H,m); 3.00(1H, m); 2.85 (2H,m); 2.40 (1H,m). MS TOF 477 (M+1$^+$). Hplc (Jupiter5. C18, Gradient 1, water/acetonitrile/TFA) rt 15.02 min.

EXAMPLE 162

3-Amidino-benzoyl-D-phenylglycine-tetrahydroisoquinolin-2-amide $^1$H nmr (CD$_3$CN). 8.05 (1H, s); 8.00 (1H, d); 7.70 (1H, d); 7.45(1H, t); 7.25(2H,m); 7.15 (3H, m); 6.90, (4H,m); 6.00 (1H, s); 4.45 (2H,m); 3.45 (2H,m); 2.55 (2H,m). MS TOF 413 (M+1$^+$). Hplc (Jupiter5 C18, Gradient 3, water/acetonitrile/TFA) rt 10.00 min.

EXAMPLE 163

3-Amidino-benzoyl-D-phenylglycinyl-N-benzyl glycine ethyl ester $^1$H nmr (CD$_3$CN) 8.15 (1H, s); 8.10 (1H, d); 7.90 (1H, d); 7.70(1H, t); 7.35 (10H, m); 6.10 (1H, s); 4.65 (2H, m); 4.45 (2H,m); 4.05 (2H,m); 1.15 (3H,m). MS TOF 473 (M+1$^+$). Hplc (Jupiter5 C18, Gradient 3, water/acetonitrile/TFA) rt 11.32 min.

EXAMPLE 164

3-Amidino-benzoyl-D-phenylglycinyl-1,2,3,4-DL-tetrahydroisoquinolin-3-dimethylamide $^1$H nmr (CD$_3$OD) mixture of isomers, major reported. 8.25 (1H, s); 8.20 (1H, d); 7.95 (1H, d); 7.75 (1H, t); 7.70-7.00 (9H, m); 635 (1H, s); 5.20 (1H,m); 4.65 (2H,m); 3.15 (2H, m, obscured by solvent); 3.00 (6H, d). MS TOF 484 (M+1$^+$). Hplc (Jupiter5 C18, Gradient 1, water/acetonitrile/TFA) rt 13.81 min.

Compounds Synthesised by Method 7

EXAMPLE 165

R-2-{[N-(3-amidino)benzoyl]amino}-2-phenylethyl-4-(methyl)benzoate $^1$H nmr (DMSO) 8.25 (1H, s); 8.21 (1H, d); 7.95 (1H, d) 7.80 (2H,d); 7.75 (1H, t); 7.50 (2H,d); 7.34 (5H, m); 5.55 (1H, q); 4.55 (2H, d); 3.35 (3H, s). MS TOF 402 (M+1$^+$). Hplc (Jupiter5 C18, Gradient 3, water/acetonitrile/TFA) rt 11.87 min.

EXAMPLE 166

R-2-{[N-(3-Amidino)benzoyl]amino}-2-phenyl-ethyl-4-dimethylaminobenzoate $^1$H nmr (CD$_3$CN) 8.20 (1H, s); 8.05 (1H,d); 7.90 (1H, d); 7.75 (2H,d); 7.65 (1H, t); 7.45 (2H, d); 7.35 (3H, m); 6.70, (2H,d); 5.50 (1H, m); 4.55 (2H,m); 1.95 (6H,s). MS TOF 431 (M+1$^+$). Hplc (Jupiter5 C18, Gradient 3, water/acetonitrile/TFA) rt 11.11 min.

EXAMPLE 167

R-2-{[N-(3-Amidino)benzoyl]amino}-2-phenyl-ethyl-4-aminosulphonylbenzoate $^1$H nmr (CD$_3$CN) 8.15 (1H, s); 8.05 (3H,m); 7.90 (3H, m); 7.65 (1H, t); 7.55 (2H,d); 7.35 (3H, m); 5.50 (1H, m); 4.65 (2H,d). MS TOF 467 (M+1$^+$). Hplc (Jupiter5 C18, Gradient 3, water/acetonitrile/TFA) rt 9.80 min.

EXAMPLE 168

R-2-{[N-(3-Amidino)benzoyl]amino}-2-phenylethyl benzoate $^1$H nmr (CD$_3$CN) 8.05 (1H, s); 8.00 (1H,d); 7.80 (2H,m); 7.70 (1H, d); 7.55-7.00 (9H, m); 5.45 (1H, m); 4.55 (2H,m). MS TOF 387 (M+1$^+$). Hplc (Jupiter5 C18, Gradient 3, water/acetonitrile/TFA) rt 10.85 min.

EXAMPLE 169

R-2-{[N-(3-Amidino)benzoyl]amino}-2-phenyl-ethyl-4-acetoxybenzoate $^1$H nmr (CD$_3$CN) 8.00(1H, s); 7.95 (1H,d); 7.85 (2H,d); 7.75 (1H, d); 7.55 (1H, t); 7.35 (2H,d); 7.20 (3H, m); 7.00, (2H,d); 5.35 (1H, m); 4.55 (2H,m); 2.10 (3H,s). MS TOF 446 (M+1$^+$). Hplc (Jupiter5 C18, Gradient 3, water/acetonitrile/TFA) rt 10.54 min.

EXAMPLE 170

R-2-{[N-(3-Amidino)benzoyl]amino}-2-phenyl-ethyl-4-isopropylbenzoate $^1$H nmr (CD$_3$CN) 8.05 (1H, s); 8.00 (1H,d); 7.90 (1H, d); 7.75 (2H,d); 7.55 (1H, t); 7.40 (2H, d); 7.25 (5H, m) 5.45 (1H, m); 4.55 (2H,m); 2.85 (1H,m); 1.10 (6H, d). MS TOF 430 (M+1$^+$). Hplc (Jupiter5 C18, Gradient 3, water/acetonitrile/TFA) rt 12.43 min.

EXAMPLE 171

R-2-{[N-(3-Amidino)benzoyl]amino}-2-phenyl-ethyl-4-hydroxybenzoate $^1$H nmr (CD$_3$CN) 8.15 (1H, s); 8.05 (3H,m); 7.85 (1H,d); 8.80 (2H,d); 7.65 (1H, t); 7.40 (5H, m); 6.80 (2H, d); 5.50 (1H, m); 4.55 (2H, d). MS TOF 404 (M+1$^+$). Hplc (Jupiter5 C18, Gradient 3, water/acetonitrile/TFA) rt 10.05 min.

The Following Compounds Were Synthesised by Method 4 and Elaborated as Example 89

EXAMPLE 172

2-Amino-5-amidino-benzoyl-D-phenylglycine benzyamide $^1$H nmr (DMSO) 8.30 (1H, s); 7.80 (1H, d); 7.75 (2H, d) 7.45 (8H, m); 7.05 (1H,d); 5.95 (1H, s); 4.55 (2H,s) MS TOF 402 (M+1$^+$). Hplc (Jupiter5 C18, Gradient 1, water/acetonitrile/TFA) rt 10.55 min.

EXAMPLE 173

2-Amino-5-amidino-benzoyl-D-phenylglycine-2-methylbenzylamide $^1$H nmr (DMSO) 8.15 (1H, s); 7.70 (1H, d); 7.60 (2H, d); 7.30 (7H, m); 6.90 (1H, d); 5.80 (1H, s); 4.30 (2H, s); 2.25 (3H,s). MS TOF 416 (M+1$^+$). Hplc (Jupiter5 C18, Gradient 1, water/acetonitrile/TFA) rt 10.07 min.

EXAMPLE 174

2-Amino-5-amidino-benzoyl-D-phenylglycine-3-methylbenzylamide $^1$H nmr (DMSO) 8.15 (1H, s); 7.60 (1H, d); 7.50 (2H, d) 7.35 (4H, m); 7.15 (1H, m); 6.95 (2H, m); 6.80 (1H, d); 5.70 (1H, s); 4.30 (2H, s); 2.25 (3H, s). MS TOF 416 (M+1$^+$). Hplc (Jupiter5 C18, Gradient 1, water/acetonitrile/TFA) rt 10.94 min.

EXAMPLE 175

2-Amino-5-amidino-benzoyl-D-phenylglycine-R-α-methylbenzylamide $^1$H nmr (DMSO) 8.15 (1H, s); 7.60 (1H, d); 7.50 (2H, d) 7.35 (5H, m); 7.15 (1H, m); 6.95 (2H, m); 6.80 (1H, d); 5.70 (1H, s); 5.00 (1H, m); 1.45 (3H, d). MS TOF 416 (M+1$^+$). Hplc (Jupiter5 C18, Gradient 1, water/acetonitrile/TFA) rt 10.58 min.

EXAMPLE 176

2-Amino-5-amidino-benzoyl-D-phenylglycine-1-naphthylamide $^1$H nmr (DMSO) 8.00 (1H, s); 7.85 (2H, m); 7.75 (1H, d); 7.50 (1H, d); 7.40 (4H, m); 7.25 (5H, m); 6.70 (1H, d); 5.60 (1H, s); 4.65 (2H, s). MS TOF 452 (M+1$^+$). Hplc (Jupiter5 C18, Gradient 1, water/acetonitrile/TFA) rt 11.17 min.

EXAMPLE 177

2-Amino-5-amidino-benzoyl-D-phenylglycine-2-methylcyclohexylamide $^1$H nmr (DMSO) 8.00 (1H, s); 7.50 (1H, d); 7.40 (2H, m); 7.25 (4H, m); 6.70 (1H, d); 5.55 (1H, s); 3.20 (1H, m); 1.7-0.7 (9H, broad m) 0.70 (3H, d). MS TOF 408 (M+1$^+$). Hplc (Jupiter5 C18, Gradient 1, water/acetonitrile/TFA) rt 10.95 min.

Compounds Synthesised by Method 12

EXAMPLE 178

R-2-{[N-(3-Amidino)benzoyl]amino}-2-phenyl-ethyl-4-methoxybenzamide

Typically Boc-(R)-1,2-diamino-1-phenylethane was prepared by the Method of O'Brien, P. et al. *J. Med. Chem.* 37 (1994) 12, 1810-1822. The free amino group was reacted with an acid chloride or an activated acid, all couplings (minimum 120 min.) were carried out in DMF. After an aqueous work up the deprotection of the Boc group was achieved with TFA. Other acid substituents were added as the HOBt or HOAt esters either by activation with HBTU/HATU, EDC or DIPCI with or without Boc protection of amino groups. The final products were purified by preparative reverse phase Hplc.

Boc-(R)-1,2 diamino-1-phenylethane (2 g) was dissolved in DCM (80 ml) and toluoylchloride (1.2 ml.) and TEA (1.1 ml.) added. The mixture was stirred at room temperature under argon overnight. The mixture was then washed with 2M sodium hydroxide solution, water, 5% hydrochloric acid and brine, dried over magnesium sulphate, filtered and evaporated. The product was recrystallised from hexane dissolved in DCM (50 ml.) and treated with TFA for 2 hrs. The solvent was evaporated and the solid triturated with diethylether. Coupling to m-benzamidine as Method 4.

$^1$H nmr (DMSO) 8.25 (1H, s); 8.20 (1H, d); 7.95 (1H, d); 7.75 (3H, m); 7.35 (5H, m); 6.90 (2H, d); 5.35 (1H, m) 3.80 (3H, s); 3.70 (2H, m). MS TOF 417 (M+1$^+$). Hplc (Jupiter5 C18, Gradient 3, water/acetonitrile/TFA) rt 10.31 min.

EXAMPLE 179

R-2-{[N-(3-Amidino)benzoyl]amino}-2-phenyl-ethyl-4-methylbenzamide $^1$H nmr (CD$_3$CN) 8.05 (1H, s); 8.00 (1H, d); 7.85 (1H, d) 7.65 (1H, t); 7.55 (2H, d); 7.35 (5H, m); 7.20 (2H, d); 5.30 (1H, m); 3.75 (2H, m); 2.30 (3H, s); MS TOF 401 (M+1$^+$). Hplc (Jupiter5 C18, Gradient 3, water/acetonitrile/TFA) rt 10.58 min.

Compounds Synthesised by Miscellaneous Methods

EXAMPLE 180

3-Amidino-benzoyl-DL-(4-methoxycarbonyl)phe-nylglycine-4-methylbenzylamine

D,L-4-Carboxyphenylglycine was prepared from 4-cy-anobenzaldehyde by a method described by Clark, B. P. et al *Biorganic & Medicinal Chemistry Letters*, 1997, 7, 2777-2780.

D,L-4-Carboxyphenylglycine (600 mg.) was suspended in methanol (30 ml) at 0° C., saturated with hydrogen chloride gas and left at room temperature overnight. The reaction mixture was then evaporated to dryness under reduced pressure, resuspended in methanol and evaporated twice more and the solid triturated with ether, filtered and dried to give D,L-4-methoxycarbonylphenylglycine methyl ester HCl salt 620 mg.

D,L-4-methoxycarbonylphenylglycine methyl ester HCl salt (600 mg) was reacted with di-t-butyl dicarbonate in dioxane/aqueous sodium bicarbonate to give after extraction with ethyl acetate and flash chromatography (SiO$_2$ hexane/ethyl acetate)-D,L-Boc-4-methoxycarbonylphenylglycine methyl ester 590 mg.-$^1$H nmr (CDCl$_3$) 7.78 (2H, d); 7.20 (2H, d); 5.61 (1H, broad d) 5.13 (1H, broad d); 3.63 (3H, s); 3.44 (3H, s); 1.16 (9H, s).

D,L-Boc-4-methoxycarbonylphenylglycine methyl ester (400 mg) was dissolved in THF 10 ml and treated with a solution of lithium hydroxide monohydrate 64 mg. in water 1 ml and the mixture stirred at room temperature for 30 min. The reaction mixture was acidified with 2M hydrochloric acid, extracted with ethyl acetate and the organic solution was washed twice with water and dried (MgSO$_4$). Evaporation of the solvent and purification by flash chromatography gave D, L-Boc-4-methoxycarbonyl-phenylglycine 282 mg. $^1$H nmr (CDCl$_3$) 8.0 (1H, broad d); 7.78 (2H, d); 7.20 (2H, d); 5.13 (1H, broad d); 3.80 (3H, s); 1.13 (9H, s)

D, L-Boc-4-methoxycarbonylphenylglycine was coupled to 4-methylphenyl-benzylamine using TBTU/DIPEA/DMF in the usual manner to give D,L-(4-methoxycarbonyl)phe-nylglycine-4-methylphenylbenzylamide.

$^1$H nmr (CDCl$_3$) 7.93 (2H, d); 7.35 (2H, d); 7.02 (2H, d) 6.93 (2H, d); 5.78 (2H, m); 5.08 (1H, broad s); 4.30 (2H, m); 3.86 (3H, s); 2.22 (3H, s); 1.30 (9H, s).

D,L-(4-methoxycarbonyl)phenylglycine-4-methylphe-nylbenzyl amide was deprotected using TFA/DCM and coupled to m-benzamidine carboxylic acid TFA salt as Method 4

$^1$H nmr (DMSO) 8.40 (1H, s); 8.30 (1H, d); 8.10 (3H, m) 7.80 (3H, m); 7.20 (4H, s); 6.00 (1H, s); 4.35 (2H, s); 4.00 (3H, s); 2.40 (3H, s);. MS TOF 459 (M+1$^+$). Hplc (Jupiter5 C18, Gradient 1, water/acetonitrile/TFA) rt 10.88 min.

EXAMPLE 181

3-(Trimethylacetyloxomethylcarbonylamidino)-ben-zoyl-D-phenylglycine-4-(4-chlorophenyl)piperazina-mide Trimethylacetyloxymethyl carbonochloridate was prepared by the Method described by Folkmann and Lund, *Synthesis*, 1990, 1159., and reacted with 3-amidino-benzoyl-D-phenylglycine-4-(4'-chlorophenyl)piperazinamide (Example 116) in acetonitrile/aqueous sodium bicarbonate to give, after flash chromatography (SiO$_2$-DCM/ethylacetate)

trimethylacetyloxymethylcarbonyl-3-amidino-benzoyl-D-phenylglycine-4-(4'-chlorophenyl)piperazinamide.

$^1$H nmr (DMSO) 8.35 (1H, s); 8.10 (1H, d); 8.00 (1H, d); 7.60 (1H, t); 7.55 (2H, m); 7.40 (3H, m); 7.20 (2H, d) 6.80, (2H, d); 6.05 (1H, s); 5.75 (2H, s); 3.75 (1H, m) 3.65 (2H, m); 3.45 (3H, m); 3.30 (1H, m); 2.85 (1H, m) 1.20 (9H, s). MS TOF no (M+1$^+$). Hplc (Jupiter5 C18, Gradient 3, water/acetonitrile/TFA) rt 13.30 min.

EXAMPLE 182

R-3-Amidino-{2-(4-benzylpiperidin-1-yl)}-1-phenylethyl benzamide

Boc-D-Phenylglycine-OH was coupled to 4-benzylpiperidine as Method 4 and the Boc group removed with TFA. The product was dissolved in dry THF and added dropwise to LiAlH$_4$ (1.2 eq) suspended in dry THF (15 ml) under nitrogen and refluxed under nitrogen for 20 hours. On cooling the reaction was carefully diluted with water, acidifed to pH 1 (HCl), and washed with EtOAc. The aqueous solution was basified to pH 10 (solid Na$_2$CO$_3$), then extracted with EtOAc to obtain product which was further elaborated as Method 4.

$^1$H nmr (CD$_3$CN) 8.25 (1H, s); 8.15 (1H, d); 7.95 (1H, d); 7.70 (1H, t) 7.55-7.10 (10H, m); 5.60 (1H, m); 3.70 (2H, m); 3.30 (2H, m); 2.95 (2H, m); 2.55 (2H, m); 1.80 (3H, m); 1.50 (2H, m). MS TOF 441 (M+1$^+$). Hplc (Jupiter5 C18, Gradient 1, water/acetonitrile/TFA) rt 13.34 min.

EXAMPLE 183

3-(benzyoxycarbonylamidino)-benzoyl-D-phenylglycine-4-(4-chlorophenyl)piperazinamide Example 116 was dissolved in DCM and DIPEA (2.2 eq) then benzyl chloroformate (1.1 eq) was added and stirred at room temperature for 45 mins. The reaction mixture was washed with water then chromatographed on silica gel 60 eluting with 65% EtOAc/Hexane to give the pure product.

$^1$H nmr (CD$_3$OD) 8.25 (1H, s); 8.05 (1H, d); 7.95 (1H, d); 7.60 (1H, t); 7.45 (5H, m); 7.20 (2H, d); 6.80 (2H, d); 6.10 (1H, s); 5.20 (2H, s); 3.80 (1H, m); 3.60 (3H, m); 3.20 (2H, m); 2.95 (1H, m); 2.50 (1H, m). MS TOF 611 (M+1$^+$). Hplc (Jupiter5 C18, Gradient 3, water/acetonitrile/TFA) rt 13.15 min.

EXAMPLE 184

3-(tert-butyloxycarbonylamidino)-benzoyl-D-phenylglycine-4-(4-chlorophenyl)piperazinamide Example 116 was dissolved in dioxane and NaHCO$_3$ (2.2 eq.), di tertbutyl dicarbonate (1.1 eq) was added and stirred at room temperature for 1 week. The reaction mixture was extracted with ethyl acetate and evaporated to dryness. The product was chromatographed on silica gel 60 eluting with 75% EtOAc/Hexane to give the pure product.

$^1$H nmr (CD$_3$OD) 8.25 (1H, s); 7.95 (2H, m); 7.55 (1H, t); 7.45 (5H, m); 7.15 (2H, d); 6.80 (2H, d); 6.10 (1H, s); 3.85 (3H, m); 3.60 (1H, m); 3.10 (2H, m); 2.90 (1H, m); 2.50 (1H, m); 1.45 (9H, s). MS TOF 577 (M+1$^+$). Hplc (Jupiter5 C18, Gradient 1, water/acetonitrile/TFA) rt 12.72 min.

EXAMPLE 185

3-(Acetylamidino)-benzoyl-D-phenylglycine-4-(4-chlorophenyl)piperazinamide

Example 116 was dissolved in dichloromethane and DIPEA (2.2 eq) added. Acetyl chloride (1.1 eq) was added and stirred at room temp for 45 mins. The reaction mixture was then washed with water and chromatographed on silica gel 60 eluting with EtOAc. The product was further purified by preparative hplc.

$^1$H nmr (CD$_3$OD) 8.25 (1H, s); 8.05 (2H, m); 7.65 (1H, t) 7.45 (5H, m); 7.25 (2H, d); 6.85 (2H, d); 6.15 (1H, s); 3.65 (3H, m); 3.60 (1H, m); 3.20 (2H, m); 3.00 (1H, m); 2.55 (1H, m); 2.40 (3H, s). MS TOF 519 (M+1$^+$). Hplc (Jupiter5 C18, Gradient 3, water/acetonitrile/TFA) rt 14.53 min.

EXAMPLE 186

(R)—O-(3-Amidinobenzyl)-N-(4-methylbenzyl) mandelamide (R)—O-(3-Cyanobenzyl) mandelic acid (R)-Mandelic acid 91 g, 6.57 mmol.) was dissolved in THF (15 ml.) and treated portionwise with sodium hydride (60% w/w, 0.798 g, 19.7 mmol.). The white suspension was heated at reflux and treated dropwise with 3-cyanobenzylbromide (1.93 g, 9.86 mmol.) in THF (20 ml.) over 5 mins. The mixture was refluxed for 2 days. The reaction mixture was cooled and treated with water (100 ml.). The aqueous phase was washed with diethyl ether then acidified to pH 1 with 10% HCl solution. The product was extracted with ethyl acetate. The extracts were washed with brine and dried over magnesium sulphate, filtered and evaporated to give the product (1.5 g) as a gum.

$^1$H nmr (CD$_3$OD) 7.70 (3H, m); 7.40 (6H, m); 5.00 (1H, s); 4.65 (2H, m).

(R)—O-(3-Cyanobenzyl)-N-(4-methylbenzyl)mandelamide

HOAt (0.27 g, 1.96 mmol.) and DBU (0.3 g, 1.96 mmol.) was dissolved in DMF (8 ml.) and cooled in ice. EDC (0.38 g, 1.96 mmol.) was added in 3 portions and stirred for 10 mins. To this mixture was added (R)—O—-(3-Cyanobenzyl) mandelic acid (0.5 g, 1.87 mmol.) in DMF (2 ml.) and the mixture allowed to warm to room temperature for 5 mins. 4-Methylbenzylamine (0.23 g, 1.96 mmol.) was then added in one portion. The mixture was stirred for 1 hr. The reaction was quenched with water (100 ml.) and basified with 0.2M sodium hydroxide solution. The product was extracted with ethylacetate. The combined extracts were washed with dilute (5%) lithium bromide solution, water and brine, dried over magnesium sulphate, filtered and evaporated to give a gum (0.58 g). The crude product was chromatographed on silica gel eluting with 35% ethylacetate in hexane.

$^1$H nmr (CDCl$_3$) 7.50 (2H, m); 7.30 (6H, m); 7.05 (4H, s); 6.90 (1H, m); 4.80 (1H, s); 4.55 (2H, m) 4.35 (2H, s); 2.25 (3H, s).

(R)—O-(3-Amidinobenzyl)-N-(4-methylbenzyl) mandelamide (R)—O-(3-Cyanobenzyl)-N-(4-methylbenzyl)mandelamide (0.16 g) was dissolved in ethanol (10 ml) and treated with hydrogen chloride gas for 30 mins. The mixture was then stirred overnight at room temperature, evaporated to dryness and dissolved again in ethanol (10 ml.). The mixture was treated with ammonia gas for 5 mins. and allowed to stand overnight. The mixture was evaporated and the product purified by preparative hplc.

$^1$H nmr (CDCl$_3$) 7.65 (1H, s); 7.50 (1H, d); 7.30 (7H, m); 7.00 (4H, s); 4.80 (1H, s); 4.55 (2H, m) 4.35 (2H, s); 2.25 (3H, s). MS TOF 387 (M+1$^+$). Hplc (Jupiter5 C18, Gradient 3, water/acetonitrile/TFA) rt 11.24 min.

EXAMPLE 187

2-(3-Amidinobenzoyl)-1-(3-phenylpropanoyl)-1-phenylhydrazine 1-(3-phenylpropanoyl)-1-phenylhydrazine 2-tert Butoxycarbonyl-1-phenylhydrazine (1.3 g) was dissolved in pyridine (6 ml.) and treated with 3-phenylpropanoyl chloride (0.75 ml.). The mixture was stirred overnight at room temperature under argon. The pyridine was then removed by evaporation and the residue taken up in ethyl acetate and washed with 10% hydrochloric acid, saturated sodium carbonate solution and brine. The ethyl acetate fraction was dried over magnesium sulphate, filtered and evaporated. The crude product was chromatographed on silica eluting 5-25% ethyl acetate in hexane. The purified product was dissolved in DCM and treated with TFA before coupling to m-benzamidine by Method 4.

$^1$H nmr (CD$_3$OD) 8.20 (1H, s); 8.05 (1H, d); 7.90 (1H, d); 7.65 (1H, t); 7.35 (5H, m); 7.10 (5H, m); 6.15 (1H, s) 2.60 (4H, m). MS TOF 388 (M+1$^+$). Hplc (Jupiter5 C18, Gradient 3, water/acetonitrile/TFA) rt 10.75 min.

EXAMPLE 188

3-{[R]-N-(3-Amidinobenzamido)-1-phenyl}methyl-5-benzyl-1,2,4-triazole.

EDC (1.6 g) was dissolved in DMF (20 ml.) and treated with HOAt (1.16 g) in DMF (10 ml.) and stirred for 10 mins. DIPEA (1.46 ml.) was then added and the stirring continued for a further 15 mins. Boc-D-phenylglycine (2 g) in DMF (10 ml.) was then added dropwise and stirring continued for a further 25 mins. 1M Hydrazine in THF (84 ml.) was then added and the mixture stirred over night. The solvents were then evaporated and the residue treated with water (100 ml), basified with 2M sodium hydroxide solution and extracted with ethyl acetate. The combined extracts were washed with water and brine, dried with magnesium sulphate, filtered and evaporated to give a yellow solid (1.38 g).

$^1$H nmr (CDCl$_3$) 7.20 (5H, s); 5.55 (1H, s); 1.25 (9H, s)

The above product (0.3 g, 1.13 mmol.) was dissolved in ethanol (6 ml.) and added dropwise to a solution of benzyl ethyl imidate hydrochloride in ethanol (3 ml.) at room temperature. The mixture was stirred for 30 mins. The solvent was then evaporated and the residue treated with dilute sodium bicarbonate solution and extracted with ethylacetate. The combined extracts were washed with brine, dried over magnesium sulphate, filtered and evaporated to give a yellow gum. (0.43 g).

$^1$H nmr (CDCl$_3$) 7.30 (10H, m); 5.80 (1H, s); 3.50 (2H, m) 1.45 (9H, s).

The above crude product (0.43 g, 1.12 mmol.) was dissolved in xylene (60 ml.) with para toluenesulphonic acid (cat.) and heated to 160° C. for 1 day. The xylene was removed under vacuo and the triazole (0.35 g) used without further purification.

$^1$H nmr (CDCl$_3$) 7.20 (10H, m); 5.70 (1H, s); 4.00 (2H, m); 1.30 (9H, s).

The above product was treated with TFA and coupled to m-benzamidine by Method 4

$^1$H nmr (CD$_3$OD) 8.20 (1H, s); 8.05 (1H, d); 7.80 (1H, d); 7.60 (1H, t); 7.20 (10H, m); 6.50 (1H, s); 4.10 (2H, s). MS TOF 411 (M+1$^+$). Hplc (Jupiter5 C18, Gradient 3, water/acetonitrile/TFA) rt 14.38 min.

REFERENCES (1) (a) Bucherer, H. T.; Steiner W. *J. Prakt. Chem* 1934, 140, 291-316.
(b) Greene T. W.; Wuts P. G. M. *Protective Groups in Organic Synthesis*, (John Wiley and Sons, Inc. 1991) 318-319 and references therein.
(c) Bolin D. R.; Sytwu I.; Humiec F.; Meienhofer J. *Int. J. Peptide Protein Res.* 1989, 33, 353-359.
(2) Shearer, B. G., Oplinger, J. A., Lee, S. *Tet. Letts.* 38(2), 179-182 (1997)
(3) Chandrakumar, N. S. *Synthetic Comms.*, 26(14), 2613-2616 (1996)
(4) Bundle et al *J. Chem, Soc. Perkin Trans I* 1985 2247)

Assay Protocols

Enzyme Inhibition Assays:

Enzyme assays were carried out at room temperature in 0.1M phosphate buffer, pH7.4 according to the method of Tapparelli et al (J. Biol. Chem. 1993,268,4734-4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, N.C., USA, Release 6.11) K$_m$ values were determined as 100.9 μM for factor Xa/pefachrome-FXA and 81.6 μM for trypsin/pefachrome-TRY. Inhibitor stock solutions were prepared at 40 mM in Me2SO and tested at 500 μM, 50 μM and 51M. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 μM, 21 μM, 330 nM, 200 nM and 100 nM respectively. NAPAP inhibited thrombin with a Ki value of 3 nM. Compounds of the invention were found to have activity in these assays.

Antithrombotic Activity

The test material (Factor Xa inhibitor) was administered either intravenously, intraperitoneally or orally to a group of rats for experiment. A second group received vehicle (saline) only as a control, and a third group of animals received a standard antithrombotic (subcutaneous 1 mw heparin) as a positive control.

To perform the experiment male Sprague-Dawley rats (250-400 g in weight) were anaesthetised by the inhalation of isoflurane with the addition of oxygen and nitrous oxide. The left or right femoral vein was carefully exposed and isolated from the femoral artery and saphenous nerve. Following removal of connective tissue a cannula containing physiological saline was inserted into the femoral vein.

A segment of each of the left and right jugular vein was exposed and separated from the surrounding connective tissue. Each segment consisted of the section of vein between the exit point from the thorax to the vessel's first major junction.

At the desired interval following the administration of the test material or vehicle a bolus injection of 'deactivated' human serum (1.32 ml.kg$^{-1}$) was administered over less than 30 seconds, via the femoral vein cannula. Two minutes following the thrombus challenge both the jugular vein segments were ligatured at both ends and left in situ for thrombi to form.

After 10 min both jugular segments were carefully excised, and placed in a petri dish containing 0.9% saline. A blood sample (1.8 ml blood+0.2 ml 3.8% sodium citrate) was obtained by cardiac puncture and the animal sacrificed by an overdose of Expiral (sodium pentobarbitone) administered intravenously via the femoral vein cannula or by cardiac puncture. The 2 segments of jugular vein were carefully dissected longitudinally along one surface to expose the lumen and dispel the vessel contents into the saline. The tissues were examined for the presence of any developed thrombi and scored accordingly.

Thrombus score:
0=No thrombus
1=One or several small thrombi
2=Several larger thrombi
3=Large thrombus occluding the vessel Compounds of the invention were found to have significant antithrombotic activity in these assays.

Partial Thromboplastin Time Test Protocol

Venous blood was collected into 3.2% (0.109 m) trisodium citrate vacutainer tubes at 1 volume of anticoagulant to nine volumes of blood.

The blood cells were separated by centrifugation at 700 g for ten minutes to yield plasma, which was frozen at 70° C. until required.

To perform the test, 100 μl of plasma was pipetted into in a glass test tube, 1 μl of test compound in DMSO was added, and allowed to warm to 37° over two minutes.

100 μl of warm (37°) Manchester (tissue thromboplasin) reagent (Helena Biosciences, UK) was added, allowed to equilibrate for sixty seconds.

100 μl of warm (37°) 25 mM calcium chloride solution was added to initiate clotting.

The test tube was tilted three times through a 90° angle every five seconds to mix the reagents and the time to clot formation recorded.

Data from a series of observations and test compound concentrations are analysed by a SAS statistical analysis program and a CT2 (Concentration required to double clotting time) for each compound is generated.

Compounds of the invention were found to significantly elongate the partial thromboplastin time.

Kaolin Activated Partial Thromboplastin Time Test Protocol

Venous blood was collected into 3.2% (0.109 m) trisodium citrate vacutainer tubes at 1 volume of anticoagulant to nine volumes of blood.

The blood cells were separated by centrifugation at 700 g for ten minutes to yield plasma, which was frozen at 70° C. until required.

To perform the test, 100 μl of plasma was pipetted into in a glass test tube, 1 μl of test compound in DMSO was added, and allowed to warm to 37° over two minutes.

10 μl of APTT reagent resuspended in Owren's buffer (Thrombosis Reference Centre University of Manchester, Withington Hospital, Manchester) was added, mixed thoroughly, and 100 μl of prewarmed kaolin suspension in Owren's buffer added.

This mixture was incubated for ten minutes at 37°, with regular gentle mixing by tilting through a 90° angle, three times sequentially at one minute intervals to maintain the kaolin in suspension.

After ten minutes 100 μl of 25 mM calcium chloride solution was added, the suspension redispersed by mixing as above and the time to clot formation recorded.

Data from a series of observations and test compound concentrations are analysed by a SAS statistical analysis program and a CT2 (Concentration required to double clotting time) for each compound is generated.

TABLE 1

Biological data for selected examples

| EX No | FXa pKi | thrombin pKi | trypsin pKi | APTT CT2 uM | PT CT2 uM |
|---|---|---|---|---|---|
| 84 | 7.98 | 5.04 | 5.61 | 5.8 | 1.9 |
| 89 | 7.85 | 5.99 | 6.61 | NT | NT |
| 63 | 7.80 | 5.96 | 6.54 | NT | 3.7 |
| 87 | 7.62 | 5.10 | 5.89 | 14 | 4.2 |
| 33 | 7.50 | 6.14 | 6.39 | NT | 7.1 |
| 32 | 7.39 | 6.09 | 5.65 | 7.4 | 5.6 |
| 65 | 7.19 | 5.93 | 5.79 | 9.7 | 13 |
| 36 | 7.12 | 6.24 | 6.16 | 9.4 | 9 |
| 64 | 7.06 | 5.72 | 5.91 | 7.6 | 8.3 |
| 68 | 7.01 | 5.32 | 5.59 | NT | 17 |
| 66 | 6.94 | 6.66 | 6.55 | 4.5 | 4.6 |
| 31 | 6.80 | 6.98 | 5.56 | 3.7 | 3.2 |
| 37 | 6.79 | 4.77 | 5.84 | 36 | 15 |
| 80 | 6.57 | 5.16 | 5.73 | NT | 13 |
| 12 | 6.39 | 5.27 | 6.10 | 6.5 | 3.4 |

EXAMPLES 189 AND 190

The compounds of Examples 189 and 190 were prepared by the method described below, but using the appropriate starting materials.

Boc D-phenylglycine (251 mg, 1 mmol.) was dissolved in dimethylformamide (3 ml) with HATU [O-(7-azabenzotriazol-1-yl)-1,1,3,3-tetramethyluronium hexafluorophosphate] (380 mg., 1 mmol.) and diisopropylethylamine (350 μl., 2 mmol.). To this mixture was added 4-methylbenzylamine (121 mg., 1 mmol.) and diisopropylethylamine (170 μl., 1 mmol.). The mixture was stirred overnight. The mixture was then taken up into ethylacetate and washed with water, sodium carbonate solution, water, 10% hydrochloric acid solution and water. The ethylacetate was evaporated without drying and treated immediately with trifluoroacetic acid (TFA) for 30 min. The TFA was then evaporated to dryness and the product triturated with diethylether. Triethylamine (1 ml) was added and evaporated to dryness. A solution of 3-hydroxymethylbenzoic acid (76 mg, 0.5 mmole) in dry dimethylformamide (DMF) was treated with TBTU [2-(1H-(benzotriazol-1-yl)-1,1,3,3-tetramethyluroniumtetrafluoroborate] (161 mg., 0.5 mmol.) and diisopropylethylamine (1.5 mmol.). The mixture was then added to the D-phenylglycine-4-methylbenzylamide (0.5 mmol.) and stirred overnight. The crude product was dissolved in water/acetonitrile (20 ml), filtered and purified by preparative Hplc to yield pure product.

$^1$H nmr (CD$_3$CN) 7.75 (1H, m); 7.65 (2H, m); 7.30 (7H, broad m); 6.80 (3H, m); 5.40 (1H, s); 4.45 (2H, s); 4.10 (2H, m); 2.10 (3H, s). MS TOF 389 (M+1$^+$). Hplc (Magellan C8, Gradient 3, water/acetonitrile/TFA) rt 13.51 min.

Compounds Made by the Above Method

EXAMPLE 189

3-Aminomethylbenzoyl-D-phenylglycine-4-aminomethylcyclohexyl methylamide $^1$H nmr (CD$_3$CN) 7.95 (2H, m); 7.80 (2H, m); 7.50 (5H, m); 5.65 (1H, s); 4.45 (2H, s); 3.30 (2H, m); 3.00 (2H, m); 2.00-1.00 (10H, m). MS TOF 409 (M+1$^+$). Hplc (Magellan C8, Gradient 3, water/acetonitrile/TFA) rt 12.68 min.

EXAMPLE 190

3-Aminomethylbenzoyl-D-phenylglycine-1-adamantylamide $^1$H nmr (CD$_3$CN) 7.95 (1H, s); 7.85 (2H, d); 7.60 (1H, m); 7.50 (2H, m); 7.40 (3H, m); 5.65 (1H., s); 4.20 (2H, s); 2.50-1.50 (15H, m). MS TOF 418 (M+1$^+$). Hplc (Magellan C8, Gradient 1, water/acetonitrile/TFA) rt 18.36 min.

What is claimed is:

1. A serine protease inhibitor compound of formula (I)

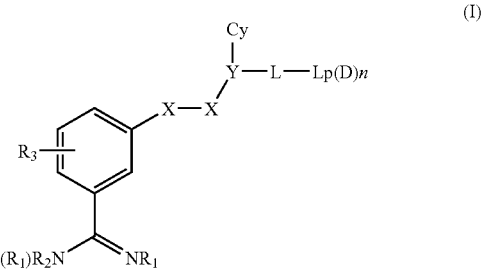

where $R_1$ and $R_2$ each independently is hydrogen or hydroxyl, alkoxy, alkyl, aminoalkyl, hydroxyalkyl, alkoxyalkyl, alkoxycarbonyl, acyloxymethoxycarbonyl or alkylamino optionally substitituted by hydroxy, alkylamino, alkoxy, oxo, aryl or cycloalkyl;

each $R_3$ independently is $R_1$, $R_2$, amino, halo, cyano, nitro, thiol, alkylthio, alkylsulphonyl, alkylsulphenyl, alkylsulphonamido, alkylaminosulphonyl, aminosulfonyl, haloalkoxy and haloalkyl;

X-X is —CH=CH—, —CONH—, —CONR$_1$—, —NH—CO—, —NH—CH$_2$—, —CH$_2$—NH—, —CH$_2$O—, —OCH$_2$—, —COO—, —OC=O—;

L is an organic linker group containing 1 to 5 backbone atoms selected from C, N, O and S, or a branched alkyl or cyclic group;

Y is a nitrogen atom or a CR$_1$ group;

Cy represents a phenyl or naphthyl group optionally substituted by groups $R_3$ or phenyl optionally substituted by $R_3$;

Lp(D)$_n$ is a lipophilic organic group, selected from an alkyl, heterocyclic, alkenyl, alkaryl, cycloalkyl, polycycloalkyl, cycloalkenyl, aryl, aralkyl or haloalkyl group or a combination of two or more such groups optionally substituted by one or more of oxa, oxo, aza, thio, halo, amino, hydroxy or $R_3$ groups;

or a physiologically tolerable salt thereof.

2. A compound as claimed in claim 1 wherein $R_1$ represents hydrogen.

3. A compound as claimed in claim 1, wherein $R_2$ is hydrogen, alkoxycarbonyl or hydroxy.

4. A compound as claimed in claim 1 wherein $R_3$ is hydrogen, amino, aminoalkyl, alkylamino, hydroxy, hydroxyalkyl, thiol, alkylthio or alkoxy.

5. A compound as claimed in claim 4 wherein $R_3$ is para to the amidino group.

6. A compound as claimed in claim 5 wherein $R_3$ is amino.

7. A compound as claimed in claim 1 wherein the X moiety nearest Y is NH.

8. A compound as claimed in claim 1 wherein the X moiety nearest the phenyl ring is CH$_2$ or CO.

9. A compound as claimed in claim 1 wherein X-X is —CONH—.

10. A compound as claimed in claim 1 wherein Y is CH.

11. A compound as claimed in claim 1 wherein Cy represents phenyl optionally substituted by $R_3$ or naphthyl optionally substituted by $R_3$.

12. A compound as claimed in claim 11 wherein Cy represents phenyl.

13. A compound as claimed in claim 1 wherein the linker L represents CO, CH$_2$NH, CONR$_1$(CH$_2$)$_m$, (CH$_2$)$_m$N(R$_1$)CO (CH$_2$)$_m$, (CH$_2$)$_{m+2}$, (CH$_2$)$_m$CO(CH$_2$)$_m$, (CH$_2$)$_m$OC=O, (CH$_2$)$_m$O or CH=CH(CH$_2$)$_m$ (where each m is independently 0 or 1).

14. A compound as claimed in claim 13 wherein the linker L represents CONR$_1$(CH$_2$)$_m$, CO or CH$_2$NR$_1$CO where m is 0 or 1.

15. A compound as claimed in claim 1 wherein said lipophilic group comprises cycloalkyl, azacycloalkyl, diazacycloalkyl, phenyl, naphthyl, adamantyl, decalinyl, tetrahydrodecalinyl, bicycloalkyl, mono- or diazabicycloalkyl, mono-, bicyclo heteroaromatic or a linear or branched alkyl, alkylene, alkenyl or alkenylene group all optionally substituted by one or more groups $R_3$, or a combination of at least two such groups linked by a spiro linkage or a single or double bond or by C=O, O, S, SO, SO$_2$, CONR$_1$, NR$_1$—CO—, NR$_1$ linkage.

16. A compound as claimed in claim 15 wherein the lipophilic group is a methylcyclohexyl, methylcyclohexylmethyl, methylphenylmethyl, phenylethyl, benzylpiperidinyl, benzoylpiperidinyl, bispiperidinyl or phenylpiperazinyl.

17. A compound as claimed in claim 1 wherein Y is carbon and has the conformation that would result from construction from a D-α-aminoacid NH$_2$—CR$_1$(Cy)—COOH.

18. A compound as claimed in claim 1 being 3-amidinobenzoyl-D-phenylglycine-4-benzoyl piperidinamide.

19. A pharmaceutical composition comprising an anticoagulant effective amount of a serine protease inhibitor as claimed in claim 1 together with at least one pharmaceutically acceptable carrier or excipient.

20. A method of treatment of the human or non-human animal body to combat a thrombotic disorder responsive to a Factor Xa inhibitor, said method comprising administering to said body an anticoagulant effective amount of a serine protease inhibitor as claimed in claim 1.

21. A serine protease inhibitor compound of formula (I)

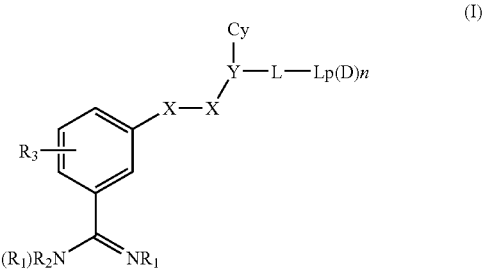

where $R_1$ represents hydrogen;
$R_2$ represents hydrogen, alkoxycarbonyl or hydroxy;
$R_3$ is hydrogen, amino, aminoalkyl, alkylamino, hydroxy, hydroxyalkyl, thiol, alkylthio or alkoxy;
X-X is CONH;
L is CO, $CH_2NH$, $CONR_1(CH_2)_m$, $(CH_2)_mN(R_1)CO$ $(CH_2)_m$, $(CH_2)_{m+2}$, $(CH_2)_mCO(CH_2)_m$, $(CH_2)_mOC=O$, $(CH_2)_mO$ or $CH=CH(CH_2)_m$ (where each m is independently 0 or 1).

Y is CH;
Cy represents phenyl optionally substituted by $R_3$ or naphthyl optionally substituted by $R_3$; and
Lp $(D)_n$ is a lipophilic organic group, selected from an alkyl, heterocyclic, alkenyl, alkaryl, cycloalkyl, polycycloalkyl, cycloalkenyl, aryl, aralkyl or haloalkyl group or a combination of two or more such groups optionally substituted by one or more of oxa, oxo, aza, thio, halo, amino, hydroxy or $R_3$ groups;
or a physiologically tolerable salt thereof.

22. A pharmaceutical composition comprising an anticoagulant effective amount of a serine protease inhibitor as claimed in claim 21 together with at least one pharmaceutically acceptable carrier or excipient.

23. A method of treatment of the human or non-human animal body to combat a thrombotic disorder responsive to a Factor Xa inhibitor, said method comprising administering to said body an anticoagulant effective amount of a serine procease inhibitor as claimed in claim 21.

* * * * *